(12) United States Patent
Nakahara et al.

(10) Patent No.: US 11,822,247 B2
(45) Date of Patent: Nov. 21, 2023

(54) MATERIAL FOR FORMING ORGANIC FILM, METHOD FOR FORMING ORGANIC FILM, PATTERNING PROCESS, AND COMPOUND

(71) Applicant: SHIN-ETSU CHEMICAL CO., LTD., Tokyo (JP)

(72) Inventors: Takayoshi Nakahara, Joetsu (JP); Daisuke Kori, Joetsu (JP); Yusuke Biyajima, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 458 days.

(21) Appl. No.: 17/183,946

(22) Filed: Feb. 24, 2021

(65) Prior Publication Data

US 2021/0286266 A1 Sep. 16, 2021

(30) Foreign Application Priority Data

Mar. 2, 2020 (JP) .................................. 2020-34704

(51) Int. Cl.
*G03F 7/11* (2006.01)
*C07C 69/40* (2006.01)
(Continued)

(52) U.S. Cl.
CPC ................ *G03F 7/11* (2013.01); *C07C 69/40* (2013.01); *C07C 233/11* (2013.01);
(Continued)

(58) Field of Classification Search
CPC . G03F 7/11; G03F 7/094; G03F 7/004; G03F 7/091; G03F 1/80; G03F 7/075;
(Continued)

(56) References Cited

U.S. PATENT DOCUMENTS

2004/0197709 A1 10/2004 Arase et al.
2005/0255712 A1 11/2005 Kato et al.
(Continued)

FOREIGN PATENT DOCUMENTS

EP 3 584 240 A1 12/2019
JP S62-257936 A 11/1987
(Continued)

OTHER PUBLICATIONS

Aug. 17, 2021 Extended Search Report issued in European Patent Application No. 21159432.0.
(Continued)

*Primary Examiner* — Caleen O Sullivan
(74) *Attorney, Agent, or Firm* — Oliff PLC

(57) ABSTRACT

The present invention is a material for forming an organic film, including: a compound shown by the following general formula (1); and an organic solvent, where in the general formula (1), X represents an organic group with a valency of "n" having 2 to 50 carbon atoms or an oxygen atom, "n" represents an integer of 1 to 10, and $R_1$ independently represents any of the following general formulae (2), where in the general formula (2), broken lines represent attachment points to X, and $Q_1$ represents a monovalent organic group containing a carbonyl group, at least a part of which is a group shown by the following general formulae (3), where in the general formulae (3), broken lines represent attachment points, $X_1$ represents a single bond or a divalent organic group having 1 to 20 carbon atoms optionally having a substituent when the organic group has an aromatic ring, $R_2$ represents a hydrogen atom, a methyl group, an ethyl group, or a phenyl group, and ** represents an attachment point. An object of the present invention is to provide a material for forming an organic film for forming an organic
(Continued)

film having dry etching resistance, and also having high filling and planarizing properties and adhesion to a substrate.

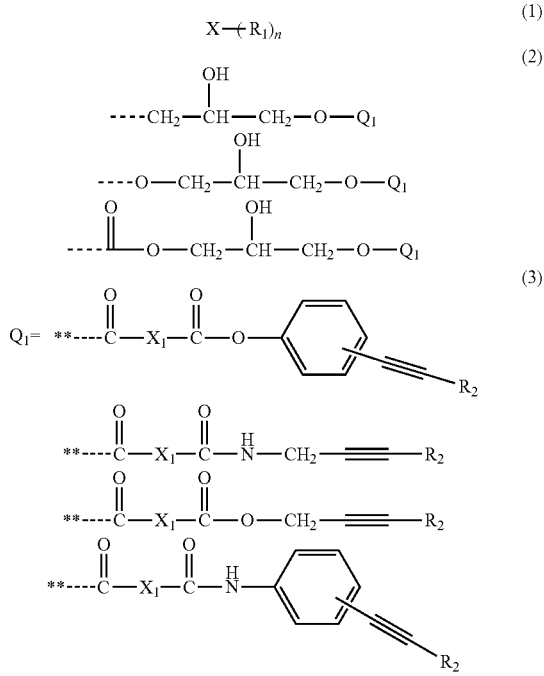

21 Claims, 4 Drawing Sheets

(51) Int. Cl.
| | |
|---|---|
| C07C 233/11 | (2006.01) |
| C07C 233/65 | (2006.01) |
| C07D 233/74 | (2006.01) |
| C07D 239/10 | (2006.01) |
| C07D 251/30 | (2006.01) |
| C09D 4/00 | (2006.01) |
| G03F 7/09 | (2006.01) |
| H01L 21/027 | (2006.01) |
| H01L 21/033 | (2006.01) |

(52) U.S. Cl.
CPC .......... *C07C 233/65* (2013.01); *C07D 233/74* (2013.01); *C07D 239/10* (2013.01); *C07D 251/30* (2013.01); *C09D 4/00* (2013.01); *G03F 7/094* (2013.01); *H01L 21/0276* (2013.01); *H01L 21/0337* (2013.01); *C07C 2603/18* (2017.05); *H01L 21/0279* (2013.01); *H01L 21/0332* (2013.01)

(58) Field of Classification Search
CPC . G03F 7/162; G03F 7/168; G03F 7/20; G03F 7/26; C07C 69/40; C07C 233/11; C07C 233/65; C07C 2603/18; C07C 233/80; C07C 235/84; C07D 233/74; C07D 239/10; C07D 251/30; C07D 487/04; C09D 4/00; H01L 21/0276; H01L 21/0337; H01L 21/0279; H01L 21/0332; H01L 21/32; C08G 59/42; C08L 63/00
USPC ......... 438/703; 430/311, 270.1, 272.1, 271.1
See application file for complete search history.

(56) References Cited

U.S. PATENT DOCUMENTS

| | | | |
|---|---|---|---|
| 2009/0311624 | A1 | 12/2009 | Horiguchi et al. |
| 2013/0302990 | A1 | 11/2013 | Watanabe et al. |
| 2016/0340469 | A1 | 11/2016 | Endo et al. |
| 2017/0183531 | A1 | 6/2017 | Kori et al. |
| 2017/0184968 | A1 | 6/2017 | Kori et al. |
| 2018/0011405 | A1 | 1/2018 | Watanabe et al. |
| 2019/0062491 | A1 | 2/2019 | Endo et al. |
| 2019/0064659 | A1 | 2/2019 | Kori et al. |
| 2019/0391493 | A1 | 12/2019 | Tachibana et al. |
| 2020/0124966 | A1 | 4/2020 | Endo et al. |
| 2021/0181637 | A1* | 6/2021 | Kori ........................ G03F 7/094 |

FOREIGN PATENT DOCUMENTS

| | | |
|---|---|---|
| JP | 2002-334869 A | 11/2002 |
| JP | 2004-205685 A | 7/2004 |
| JP | 2007-199653 A | 8/2007 |
| JP | 3985165 B2 | 10/2007 |
| JP | 4784784 B2 | 10/2011 |
| JP | 2013-253227 A | 12/2013 |
| JP | 2017-119670 A | 7/2017 |
| TW | 201536828 A | 10/2015 |
| TW | 201809889 A | 3/2018 |
| TW | 201920446 A | 6/2019 |
| WO | 2004/066377 A1 | 8/2004 |
| WO | 2018/190380 A1 | 10/2018 |

OTHER PUBLICATIONS

Feb. 7, 2023 Office Action issued in Japanese Patent Application No. 2020-034704.
Jan. 13, 2022 Office Action and Search Report issued in Taiwanese Application No. 110106834.

* cited by examiner

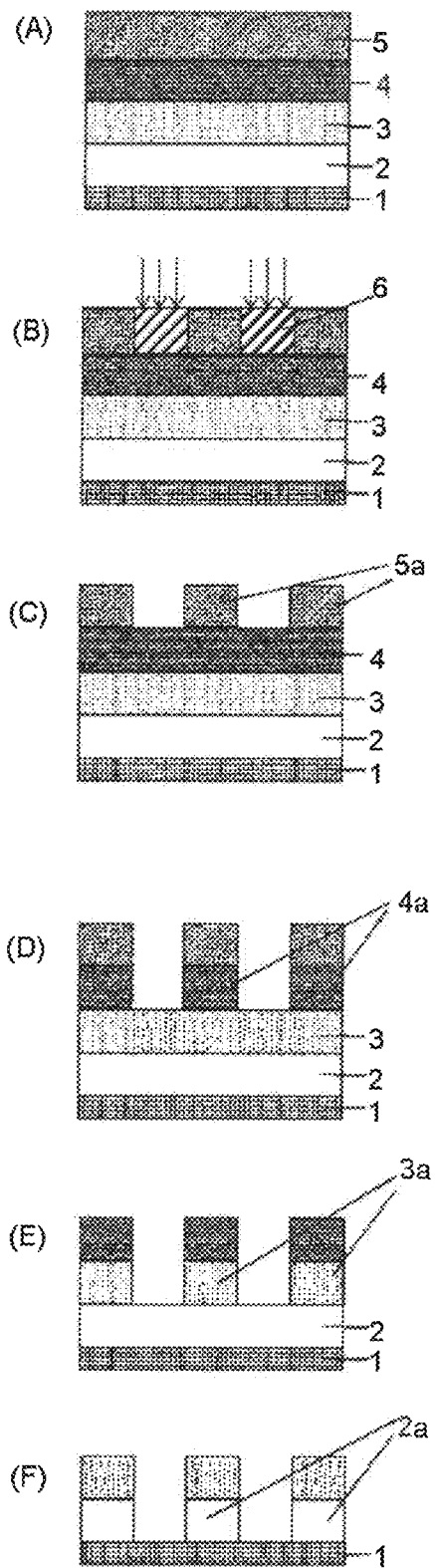
[FIG. 1]

[FIG. 2]
(G)
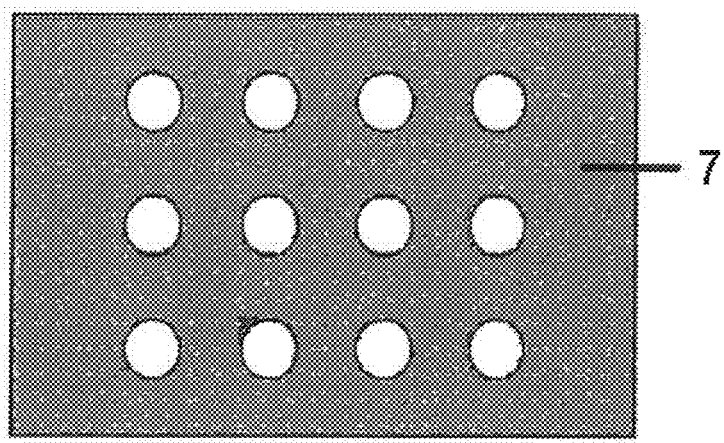
(H)
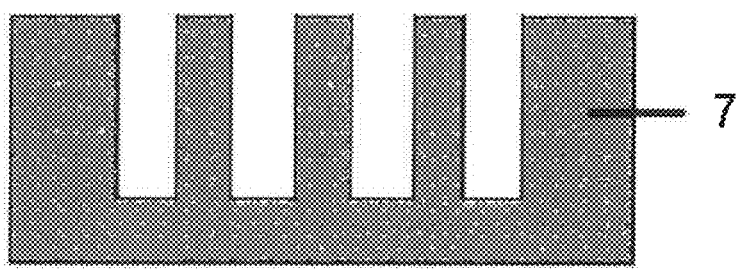
(I)
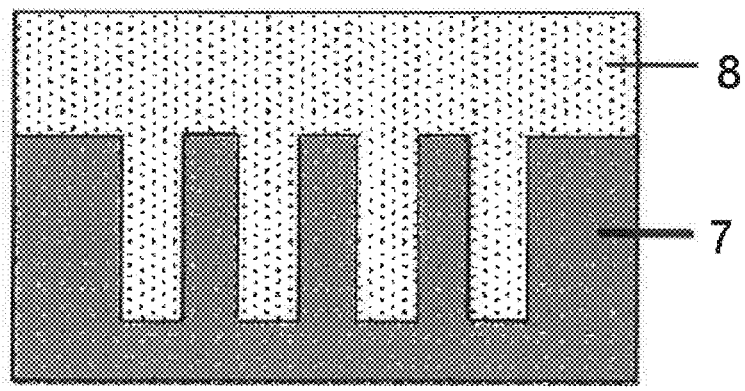

[FIG. 3]
(J)
(K)
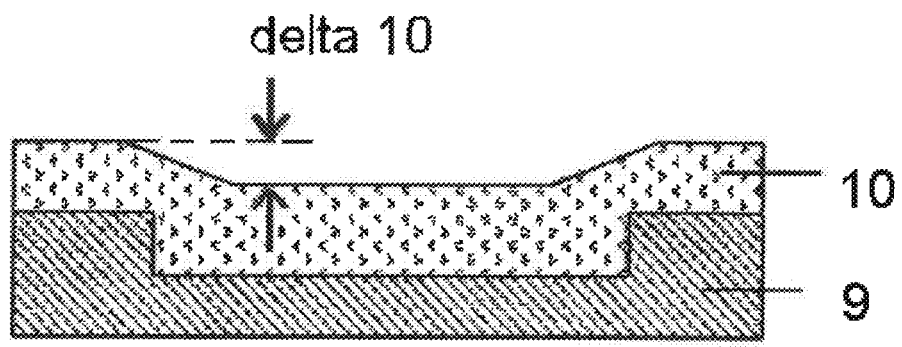

[FIG. 4]
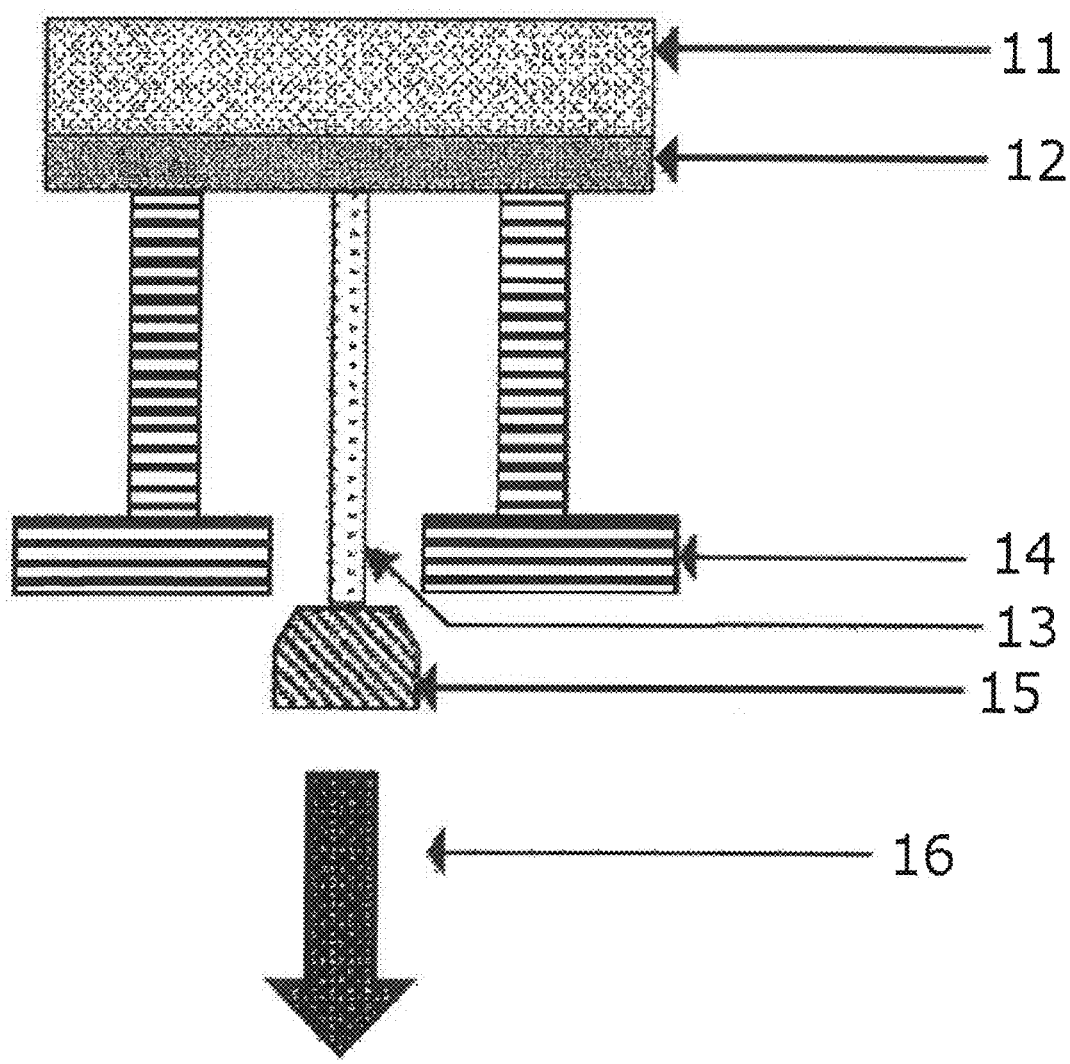

MATERIAL FOR FORMING ORGANIC FILM, METHOD FOR FORMING ORGANIC FILM, PATTERNING PROCESS, AND COMPOUND

TECHNICAL FIELD

The present invention relates to: a material for forming an organic film for forming a resist underlayer film used in a multilayer resist process or the like employed for fine processing in a manufacturing process of a semiconductor device, etc. and for forming an organic film effective as a planarizing material for manufacturing a semiconductor device, and the like; a method for forming a film using this material; a patterning process suitable for exposure to deep ultraviolet ray, KrF excimer laser beam (248 nm), ArF excimer laser beam (193 nm), $F_2$ laser beam (157 nm), Kr laser beam (146 nm), Ar laser beam (126 nm), soft X-ray (EUV), electron beam (EB), ion beam, X-ray, and the like using the material for forming an organic film; and a compound useful as a component of the material for forming an organic film.

BACKGROUND ART

As LSI advances toward high integration and high processing speed, miniaturization of pattern size is progressing rapidly. Along with the miniaturization, lithography technology has achieved a fine patterning by shortening the wavelength of a light source and selecting an appropriate resist composition accordingly. The composition mainly used is a positive photoresist composition for monolayer. The monolayer positive photoresist composition not only allows a resist resin to have a skeleton having etching resistance against dry etching with chlorine- or fluorine-based gas plasma, but also provides a resist mechanism that makes an exposed part soluble, thereby dissolving the exposed part to form a pattern and processing a substrate to be processed, on which the resist composition has been applied, by dry etching using the remaining resist pattern as an etching mask.

However, when the pattern becomes finer, that is, the pattern width is reduced without changing the thickness of the photoresist film to be used, resolution performance of the photoresist film is lowered. In addition, pattern development of the photoresist film with a developer excessively increases a so-called aspect ratio of the pattern, resulting in pattern collapse. Therefore, the photoresist film has been thinned along with the miniaturization of the pattern.

On the other hand, a substrate to be processed has been generally processed by dry etching while using a pattern-formed photoresist film as an etching mask. In practice, however, there is no dry etching method capable of providing an absolute etching selectivity between the photoresist film and the substrate to be processed. The resist film is thus damaged and collapses during processing of the substrate, and the resist pattern cannot be precisely transferred to the substrate to be processed. Accordingly, higher dry etching resistance has been required in a resist composition along with the miniaturization of the pattern. In addition, the use of shorter wavelength exposure radiations has required resins used for photoresist compositions to have low absorbance at the wavelength to be used for the exposure. Accordingly, as the radiation shifts from i-beam to KrF and to ArF, the resin shifts to novolak resins, polyhydroxystyrene, and resins having an aliphatic polycyclic skeleton. This shift actually accelerates an etching rate under the above-described dry etching conditions, and recent photoresist compositions having high resolution tend to have low etching resistance.

As a result, a substrate to be processed has to be dry etched with a thinner photoresist film having lower etching resistance. The need to provide a material for this process and the process itself has become urgent.

A multilayer resist method is one solution for these problems. This method is as follows: a middle layer film having a different etching selectivity from a photoresist film (i.e., a resist upper layer film) is placed between the resist upper layer film and a substrate to be processed; a pattern is formed in the resist upper layer film; then, the pattern is transferred to the middle layer film by dry etching while using the resist upper layer film pattern as a dry etching mask; and the pattern is further transferred to the substrate to be processed by dry etching while using the middle layer film as a dry etching mask.

One of the multilayer resist methods is a 3-layer resist method, which can be performed with a typical resist composition used in the monolayer resist method. For example, this 3-layer resist method includes the following steps: an organic film containing a novolak or the like is formed as a resist underlayer film on a substrate to be processed; a silicon-containing film is formed thereon as a resist middle layer film; a usual organic photoresist film is formed thereon as a resist upper layer film. Since the organic resist upper layer film exhibits a favorable etching selectivity ratio relative to the silicon-containing resist middle layer film when dry etching is performed with fluorine-based gas plasma, the resist upper layer film pattern can be transferred to the silicon-containing resist middle layer film by employing dry etching with fluorine-based gas plasma. Furthermore, since the silicon-containing resist middle layer film exhibits a favorable etching selectivity ratio relative to an organic underlayer film in the etching using an oxygen gas or a hydrogen gas, a silicon-containing middle layer film pattern is transferred to the underlayer film by means of etching using an oxygen gas or a hydrogen gas. According to this process, even when a resist composition which is difficult to form a pattern in so that the pattern has a sufficient film thickness for directly processing the substrate to be processed or a resist composition which has insufficient dry etching resistance for processing the substrate is used, a pattern of an organic film (resist underlayer film) containing a novolak or the like having a sufficient dry etching resistance for the processing can be obtained when the pattern can be transferred to the silicon-containing film (resist middle layer film).

While numerous processes have been known (for example, Patent Document 1) for the organic underlayer film as described above, in recent years, there has now been growing necessity to have excellent filling property, planarizing property and adhesiveness to a substrate in addition to dry etching resistance. For example, when an underlying substrate to be processed has a fine pattern structure such as a hole or a trench, it is necessary to have filling property for filling in the pattern with a film without any voids. In addition, when the underlying substrate to be processed has a step(s), or when a pattern-dense region and a pattern-free region exist on the same substrate, it is necessary to planarize the film surface by the underlayer film. By planarizing the surface of the underlayer film, fluctuation in the film thickness of a middle layer or a photoresist formed thereon is controlled, whereby a focus margin in lithography or a margin in the processing step of the substrate to be processed thereafter can be enlarged. Furthermore, when an inorganic hard mask is formed on the organic underlayer film, adhesion to a substrate is necessary. When adhesion is enhanced, film delamination on forming an inorganic hard mask directly on an organic film by a CVD method or an ALD method can be prevented, and an organic film excellent in process margin can be formed.

To improve the filling and planarizing properties of an underlayer film material, addition of a liquid additive such as polyether polyol has been proposed (Patent Document 2). However, an organic film formed by this method contains many polyether polyol units, which are inferior in etching resistance. Thus, this film has a markedly lowered etching resistance and is unsuitable for the 3-layer resist underlayer film. In addition, a resist underlayer film material having a lactone ring structure as a component has been suggested as a means for enhancing the adhesion of the underlayer film material to a substrate (Patent Document 3). However, the resist underlayer film material has a problem that the adhesiveness to a substrate is not sufficient for the requirements in a cutting-edge device. Accordingly, a resist underlayer film material having excellent filling and planarizing properties and adhesion to a substrate as well as sufficient etching resistance, and a patterning process using this material are desired.

Moreover, the organic film material excellent in filling property, planarizing property, and adhesion to a substrate is not limited to use for the underlayer film for 3-layer resist, and is widely usable also as a planarizing material for manufacturing a semiconductor device, e.g., for planarizing a substrate prior to patterning by nanoimprinting. For global planarizing in the semiconductor device manufacturing process, a CMP process is now generally used. However, the CMP process is costly, so that this material is also expected to be used for the global planarizing method, instead of CMP.

CITATION LIST

Patent Literature

Patent Document 1: JP 2004-205685 A
Patent Document 2: JP 4784784 B
Patent Document 3: JP 3985165 B

SUMMARY OF INVENTION

Technical Problem

The present invention has been accomplished in view of the above circumstances, and an object thereof is to provide a material for forming an organic film for forming an organic film having dry etching resistance, and also having high filling and planarizing properties and adhesion to a substrate.

Solution to Problem

To achieve the object, the present invention provides a material for forming an organic film, comprising: a compound shown by the following general formula (1); and an organic solvent, $$X\text{---}(R_1)_n \tag{1}$$

wherein in the general formula (1), X represents an organic group with a valency of "n" having 2 to 50 carbon atoms or an oxygen atom, "n" represents an integer of 1 to 10, and $R_1$ independently represents any of the following general formulae (2),

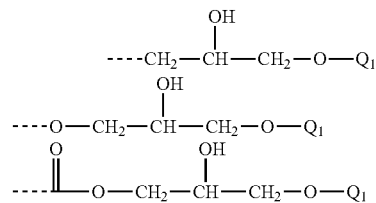

wherein in the general formulae (2), broken lines represent attachment points to X, and $Q_1$ represents a monovalent organic group containing a carbonyl group, at least a part of which is a group shown by the following general formulae (3),

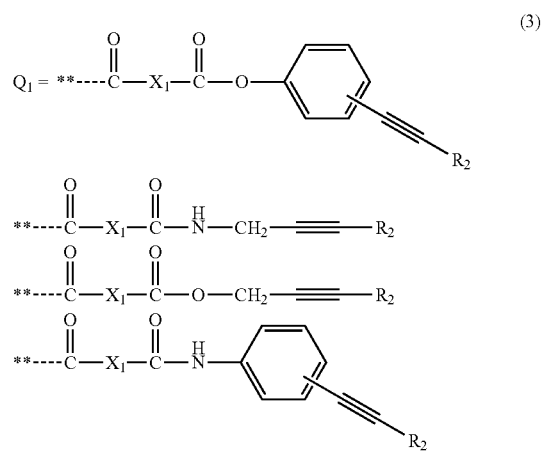

wherein in the general formulae (3), broken lines represent attachment points, $X_1$ represents a single bond or a divalent organic group having 1 to 20 carbon atoms optionally having a substituent when the organic group has an aromatic ring, $R_2$ represents a hydrogen atom, a methyl group, an ethyl group, or a phenyl group, and ** represents an attachment point.

An organic film having high dry etching resistance as well as high filling and planarizing properties can be formed with such a material for forming an organic film. Furthermore, adhesiveness to a substrate is high since the compound has two carbonyl groups, and when the compound also has an amide group, an organic film having higher adhesiveness can be formed.

In this event, the compound shown by the general formula (1) in the material for forming an organic film is preferably shown by the following general formulae (4), (6), (7), (8), (9), (10), (11), (12), (13), and (14),

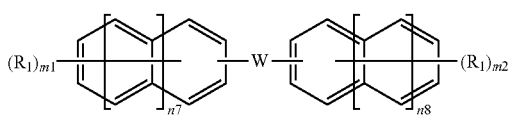

wherein in the general formula (4), n7 and n8 each independently represent 0 or 1, W represents a single bond or any structure shown by the following general formulae (5), $R_1$ has the same meaning as defined above, m1 and m2 each independently represent an integer of 0 to 4, and m1+m2 is 1 or more to 8 or less,

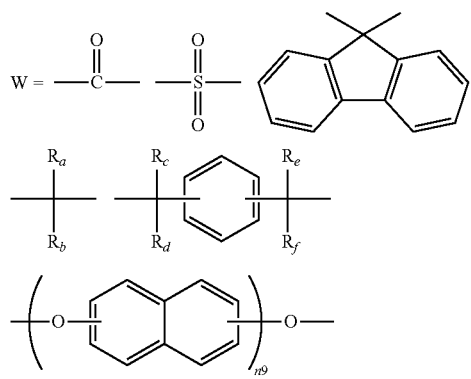

(5)

wherein in the general formulae (5), n9 represents an integer of 0 to 3, $R_a$ to $R_f$ each independently represent a hydrogen atom or an optionally fluorine-substituted alkyl group having 1 to 10 carbon atoms or phenyl group, and $R_a$ and $R_b$ are optionally bonded with each other to form a ring,

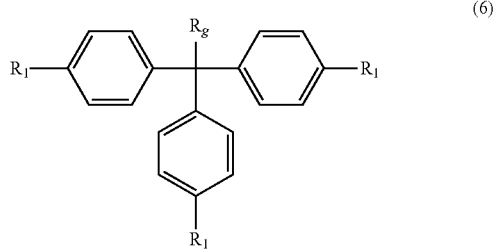

(6)

wherein in the general formula (6), $R_g$ represents a hydrogen atom, a methyl group, or a phenyl group.

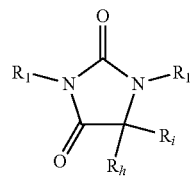

(7)

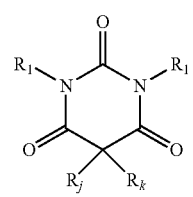

(8)

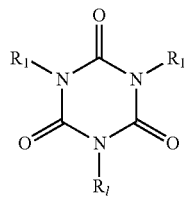

(9)

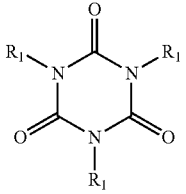

(10)

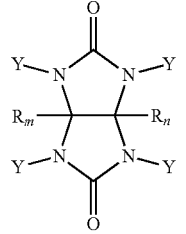

(11)

In the general formulae (7) to (11), $R_1$ has the same meaning as defined above, $R_h$, $R_i$, $R_j$, $R_k$, $R_l$, $R_m$, and $R_n$ each represent a hydrogen atom, an alkyl group having 1 to 10 carbon atoms, an alkynyl group having 2 to 10 carbon atoms, an alkenyl group having 2 to 10 carbon atoms, or a benzyl group or a phenyl group optionally having a substituent on an aromatic ring, Y represents $R_1$, a hydrogen atom, an alkyl group having 1 to 10 carbon atoms, an alkynyl group having 2 to 10 carbon atoms, or an alkenyl group having 2 to 10 carbon atoms, and at least two of the four Ys in the general formula (11) represent $R_1$.

$$R_1 \text{—} R_o \text{—} R_1 \quad (12)$$

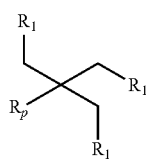

(13)

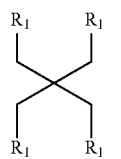

(14)

In the general formulae (12) to (14), $R_1$ has the same meaning as defined above, $R_o$ in the general formula (12) represents a linear saturated or unsaturated divalent hydrocarbon group having 1 to 20 carbon atoms or a branched or cyclic saturated or unsaturated divalent hydrocarbon group having 3 to 20 carbon atoms, and $R_p$ in the general formula (13) represents a hydrogen atom or an alkyl group having 1 to 10 carbon atoms.

Such a material for forming an organic film can provide an organic film having favorable dry etching resistance as well as high filling property, planarizing property, and adhesiveness to a substrate.

Furthermore, the present invention provides a material for forming an organic film, wherein $Q_1$ in the general formula (2) comprises any one or more shown by the general formulae (3) and any one or more shown by the following general formulae (15) and (16),

(15)

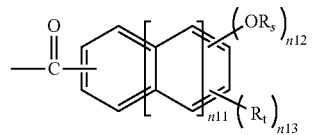
(16)

wherein $R_q$ in the general formula (15) represents a linear saturated or unsaturated hydrocarbon group having 1 to 30 carbon atoms or a branched or cyclic saturated or unsaturated hydrocarbon group having 3 to 30 carbon atoms, a methylene group comprised in $R_q$ is optionally substituted with an oxygen atom or a carbonyl group, and in the general formula (16), $R_s$ represents a hydrogen atom, a linear hydrocarbon group having 1 to 10 carbon atoms, or a branched hydrocarbon group having 3 to 10 carbon atoms, $R_t$ represents a linear hydrocarbon group having 1 to 10 carbon atoms, a branched hydrocarbon group having 3 to 10 carbon atoms, a halogen atom, a nitro group, an amino group, a nitrile group, an alkoxycarbonyl group having 1 to 10 carbon atoms, or an alkanoyloxy group having 1 to 10 carbon atoms, n11 represents 0 to 2, n12 and n13 represent a number of substituents on the aromatic ring, n12 and n13 represent an integer of 0 to 7, and n12+n13 is 0 or more to 7 or less.

When the material for forming an organic film contains such a compound, various physical properties such as heat resistance, etching resistance, high filling and planarizing properties, adhesiveness to a substrate, and control of an optical constant can be appropriately adjusted and improved according to the required performance by combining an aromatic ring structure and a structure of a hydrocarbon terminal group.

Furthermore, the organic solvent is preferably a mixture of one or more organic solvents each having a boiling point of lower than 180° C. and one or more organic solvents each having a boiling point of 180° C. or higher.

With such a material for forming an organic film, the above-described polymer is provided with thermal flowability of films by adding a high-boiling-point solvent, so that a material for forming an organic film having both high filling and planarizing properties is achieved.

In this manner, when the inventive material for forming an organic film is used, for example, for forming a multilayer resist film applied in fine processing in a manufacturing process of a semiconductor device, etc., an organic film (resist underlayer film) having high dry etching resistance as well as high filling and planarizing properties and adhesion to a substrate can be provided. In addition, a planarizing material for manufacturing a semiconductor device that can be applied for planarizing in a semiconductor device manufacturing process other than a multilayer resist process and that has high filling and planarizing properties and adhesion to a substrate can also be provided.

Furthermore, the present invention provides a method for forming an organic film that functions as an organic flat film employed in a semiconductor device manufacturing process, the method comprising:
  spin-coating a substrate to be processed with the material for forming an organic film; and
  heating the substrate to be processed at a temperature of 100° C. or higher to 600° C. or lower for 10 to 600 seconds to form a cured film.

In this manner, by coating with the material for forming an organic film and heating the material for forming an organic film at a temperature of 100° C. or higher to 600° C. or lower for 10 to 600 seconds, crosslinking reaction is promoted, and mixing with the upper layer film can be prevented.

Furthermore, the present invention provides a method for forming an organic film that functions as an organic flat film employed in a semiconductor device manufacturing process, the method comprising:
  spin-coating a substrate to be processed with the material for forming an organic film; and
  heating the substrate to be processed in an atmosphere having an oxygen concentration of 0.1% or more to 21% or less to form a cured film.

When the inventive material for forming an organic film is heated (baked) in such an oxygen atmosphere, a sufficiently cured organic film can be obtained.

In the above, the substrate to be processed preferably has a structure or a step with a height of 30 nm or more.

The inventive material for forming an organic film is excellent in high filling and planarizing properties and adhesion to a substrate, and is therefore, particularly useful when forming a flat organic film on a substrate having a structure or a step with a height of 30 nm or more.

Furthermore, the present invention provides a patterning process comprising:
  forming a resist underlayer film by using the material for forming an organic film on a body to be processed;
  forming a resist middle layer film by using a resist middle layer film material containing a silicon atom on the resist underlayer film;
  forming a resist upper layer film by using a resist upper layer film material being a photoresist composition on the resist middle layer film;
  forming a circuit pattern in the resist upper layer film;
  transferring the pattern to the resist middle layer film by etching while using the resist upper layer film having the formed circuit pattern as an etching mask;
  transferring the pattern to the resist underlayer film by etching while using the resist middle layer film having the transferred circuit pattern as an etching mask; and
  further forming the circuit pattern on the body to be processed by etching while using the resist underlayer film having the transferred circuit pattern as an etching mask.

In such a multilayer resist process, a fine pattern can be formed with high precision on a substrate to be processed according to the patterning process using the inventive material for forming an organic film.

Furthermore, the present invention provides a patterning process comprising:
  forming a resist underlayer film by using the material for forming an organic film on a body to be processed;

forming a resist middle layer film by using a resist middle layer film material containing a silicon atom on the resist underlayer film;

forming a BARC (organic antireflective coating) on the resist middle layer film;

forming a resist upper layer film by using a resist upper layer film material being a photoresist composition on the BARC so that a 4-layered film structure is constructed;

forming a circuit pattern in the resist upper layer film;

transferring the pattern to the BARC and the resist middle layer film by etching while using the resist upper layer film having the formed circuit pattern as an etching mask;

transferring the pattern to the resist underlayer film by etching while using the resist middle layer film having the transferred circuit pattern as an etching mask; and further forming the circuit pattern on the body to be processed by etching while using the resist underlayer film having the transferred circuit pattern as an etching mask.

As described, instead of forming a photoresist film directly on the resist middle layer film as a resist upper layer film, a BARC (organic antireflective coating) can be formed on the resist middle layer film by spin-coating or the like, and the resist upper layer film can be formed thereon.

Furthermore, the present invention provides a patterning process comprising:

forming a resist underlayer film by using the material for forming an organic film on a body to be processed;

forming an inorganic hard mask middle layer film selected from a silicon oxide film, a silicon nitride film, and a silicon oxynitride film on the resist underlayer film;

forming a resist upper layer film by using a resist upper layer film material being a photoresist composition on the inorganic hard mask middle layer film;

forming a circuit pattern in the resist upper layer film;

transferring the pattern to the inorganic hard mask middle layer film by etching while using the resist upper layer film having the formed circuit pattern as an etching mask;

transferring the pattern to the resist underlayer film by etching while using the inorganic hard mask middle layer film having the transferred circuit pattern as an etching mask; and further forming the circuit pattern on the body to be processed by etching while using the resist underlayer film having the transferred circuit pattern as an etching mask.

Furthermore, the present invention provides a patterning process comprising:

forming a resist underlayer film by using the material for forming an organic film on a body to be processed;

forming an inorganic hard mask middle layer film selected from a silicon oxide film, a silicon nitride film, and a silicon oxynitride film on the resist underlayer film;

forming a BARC (organic antireflective coating) on the inorganic hard mask middle layer film;

forming a resist upper layer film by using a resist upper layer film material being a photoresist composition on the BARC, so that a 4-layered film structure is constructed;

forming a circuit pattern in the resist upper layer film;

transferring the pattern to the BARC and the inorganic hard mask middle layer film by etching while using the resist upper layer film having the formed circuit pattern as an etching mask;

transferring the pattern to the resist underlayer film by etching while using the inorganic hard mask middle layer film having the transferred circuit pattern as an etching mask; and further forming the circuit pattern on the body to be processed by etching while using the resist underlayer film having the transferred circuit pattern as an etching mask.

As described, the resist middle layer film may be formed on the resist underlayer film, but instead, any inorganic hard mask middle layer film selected from a silicon oxide film, a silicon nitride film, and a silicon oxynitride film can also be formed on the resist underlayer film. Furthermore, a photoresist film may be formed directly on the inorganic hard mask middle layer film as a resist upper layer film, but alternatively, a BARC (organic antireflective coating) can be formed on the inorganic hard mask middle layer film by spin-coating or the like, and the resist upper layer film can be formed thereon. When a SiON film (silicon oxynitride film) is used as the inorganic hard mask middle layer film, the two layers of antireflective coating including the SiON film and the BARC make it possible to suppress the reflection even in liquid immersion exposure at a high NA exceeding 1.0. Another advantage in forming the BARC is having an effect of reducing footing of the photoresist pattern immediately above the SiON film.

In addition, in the inventive patterning process, the inorganic hard mask middle layer film can be formed by a CVD method or an ALD method.

As described, in the inventive patterning process, an inorganic hard mask middle layer film formed by a CVD method or an ALD method and a resist underlayer film formed by a spin-coating method or the like can be combined.

Furthermore, in the pattern formation on the resist upper layer film, the pattern is preferably formed by a photolithography with a wavelength of 10 nm or more to 300 nm or less, a direct drawing by electron beam, a nanoimprinting, or a combination thereof.

In addition, development in the patterning process is preferably alkaline development or development with an organic solvent.

Such a patterning process and development method can be suitably used in the present invention.

Furthermore, the body to be processed is preferably a semiconductor device substrate or the semiconductor device substrate coated with any of a metal film, a metal carbide film, a metal oxide film, a metal nitride film, a metal oxycarbide film, or a metal oxynitride film.

Furthermore, as the body to be processed, a body to be processed including metallic silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof is preferably used.

According to the inventive patterning process, the above-described body to be processed can be used to process and to form a pattern.

Moreover, the present invention provides a compound shown by the following general formula (1),

wherein in the general formula (1), X represents an organic group with a valency of "n" having 2 to 50 carbon atoms or an oxygen atom, "n" represents an integer of 1 to 10, and $R_1$ independently represents any of the following general formulae (2),

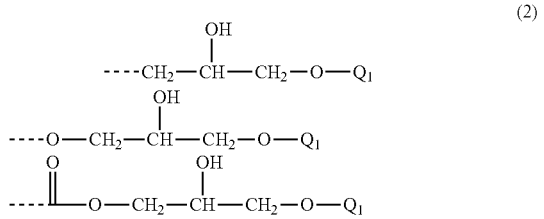

wherein in the general formulae (2), broken lines represent attachment points to X, and $Q_1$ represents a monovalent organic group containing a carbonyl group, at least a part of which is a group shown by the following general formulae (3),

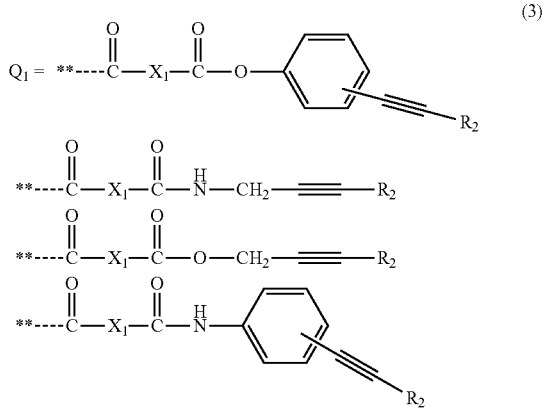

wherein in the general formulae (3), broken lines represent attachment points, $X_1$ represents a single bond or a divalent organic group having 1 to 20 carbon atoms optionally having a substituent when the organic group has an aromatic ring, $R_2$ represents a hydrogen atom, a methyl group, an ethyl group, or a phenyl group, and ** represents an attachment point.

When the inventive compound is used as a component in a material for forming an organic film, an organic film having high dry etching resistance as well as high filling and planarizing properties can be formed with the obtained material for forming an organic film. High thermosetting property can be provided by appropriately selecting a terminal substituent containing a triple bond, and film shrinking during baking can be reduced. When film shrinking is reduced, an organic film excellent in planarizing property can be formed, and in addition, the internal stress of the coating film is reduced, so that adhesiveness to a substrate is also enhanced. Furthermore, the adhesiveness to a substrate is high since the terminal substituent has two carbonyl groups, and when an amide group is also contained, an organic film having higher adhesiveness can be formed. In addition, since the compound has a terminal substituent containing a triple bond, sufficient thermosetting property is exhibited without generating a sublimation product even under an inert gas atmosphere. Therefore, a film can be formed without damage to a carbonyl group or an amide group, and high adhesiveness to a substrate is exhibited not only in the atmosphere, but also under inert gas. Consequently, the inventive compound is extremely useful for a material for forming an organic film for forming an organic film excellent in high filling property, high planarizing property, and adhesiveness to a substrate.

In this event, the compound shown by the general formula (1) is preferably any of the compounds shown by the following general formulae (4), (6), (7), (8), (9), (10), (11), (12), (13), and (14),

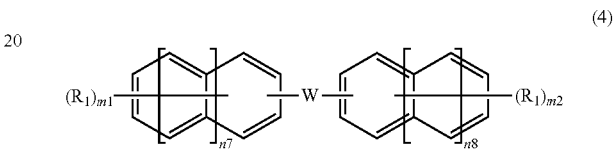

wherein in the general formula (4), n7 and n8 each independently represent 0 or 1, W represents a single bond or any structure shown by the following general formulae (5), $R_1$ has the same meaning as defined above, m1 and m2 each independently represent an integer of 0 to 4, and m1+m2 is 1 or more to 8 or less,

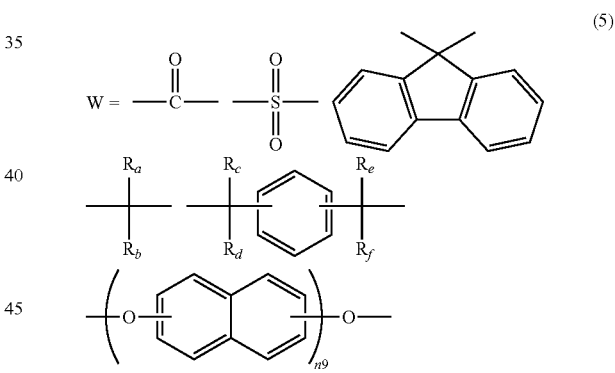

wherein in the general formulae (5), n9 represents an integer of 0 to 3, $R_a$ to $R_f$ each independently represent a hydrogen atom or an optionally fluorine-substituted alkyl group having 1 to 10 carbon atoms or phenyl group, and $R_a$ and $R_b$ are optionally bonded with each other to form a ring,

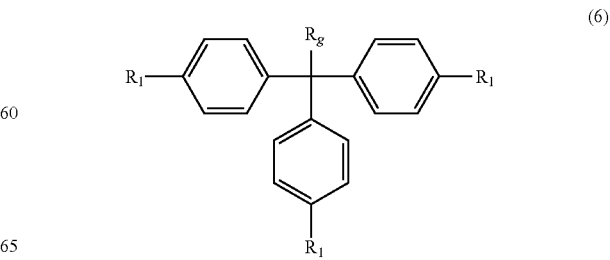

wherein in the general formula (6), $R_g$ represents a hydrogen atom, a methyl group, or a phenyl group.

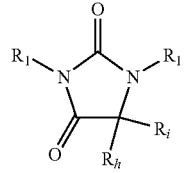
(7)

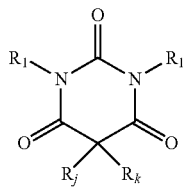
(8)

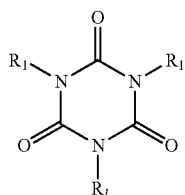
(9)

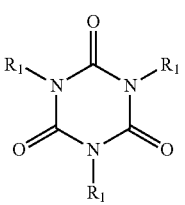
(10)

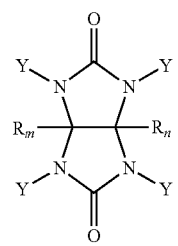
(11)

In the general formulae (7) to (11), $R_1$ has the same meaning as defined above, $R_h$, $R_i$, $R_j$, $R_k$, $R_l$, $R_m$, and $R_n$ each represent a hydrogen atom, an alkyl group having 1 to 10 carbon atoms, an alkynyl group having 2 to 10 carbon atoms, an alkenyl group having 2 to 10 carbon atoms, or a benzyl group or a phenyl group optionally having a substituent on an aromatic ring, Y represents $R_1$, a hydrogen atom, an alkyl group having 1 to 10 carbon atoms, an alkynyl group having 2 to 10 carbon atoms, or an alkenyl group having 2 to 10 carbon atoms, and at least two of the four Ys in the general formula (11) represent $R_1$.

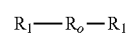
(12)

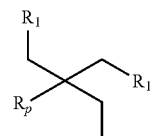
(13)

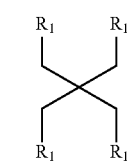
(14)

In the general formulae (12) to (14), $R_1$ has the same meaning as defined above, $R_o$ in the general formula (12) represents a linear saturated or unsaturated divalent hydrocarbon group having 1 to 20 carbon atoms or a branched or cyclic saturated or unsaturated divalent hydrocarbon group having 3 to 20 carbon atoms, and $R_p$ in the general formula (13) represents a hydrogen atom or an alkyl group having 1 to 10 carbon atoms.

Such a compound is excellent in high filling property, planarizing property, and adhesiveness, and etching resistance and optical characteristics can be appropriately adjusted according to the required performance. When the compound is used as a component of a material for forming an organic film, the material for forming an organic film can form an organic film having both dry etching resistance and adhesiveness to a substrate according to the required performance.

In this event, the compound can be such that $Q_1$ in the general formula (2) comprises any one or more shown by the general formulae (3) and any one or more shown by the following general formulae (15) and (16),

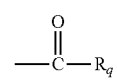
(15)

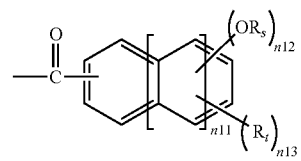
(16)

wherein $R_q$ in the general formula (15) represents a linear saturated or unsaturated hydrocarbon group having 1 to 30 carbon atoms or a branched or cyclic saturated or unsaturated hydrocarbon group having 3 to 30 carbon atoms, a methylene group comprised in $R_q$ is optionally substituted with an oxygen atom or a carbonyl group, and in the general formula (16), $R_s$ represents a hydrogen atom, a linear hydrocarbon group having 1 to 10 carbon atoms, or a branched hydrocarbon group having 3 to 10 carbon atoms, $R_t$ represents a linear hydrocarbon group having 1 to 10 carbon atoms, a branched hydrocarbon group having 3 to 10 carbon atoms, a halogen atom, a nitro group, an amino group, a nitrile group, an alkoxycarbonyl group having 1 to 10 carbon atoms, or an alkanoyloxy group having 1 to 10 carbon atoms, n11 represents 0 to 2, n12 and n13 represent a number of substituents on the aromatic ring, n12 and n13 represent an integer of 0 to 7, and n12+n13 is 0 or more to 7 or less.

When such a compound is blended in a material for forming an organic film, an aromatic ring structure and a structure of a hydrocarbon terminal group are combined so that when the compound is used as a component in a material for forming an organic film, various physical properties such as heat resistance, etching resistance, high filling and planarizing properties, adhesiveness to a substrate, and control of an optical constant can be appropriately adjusted and improved according to the required performance.

Advantageous Effects of Invention

As described above, the present invention can provide: a compound useful as a component of a material for forming an organic film for forming an organic film having high filling and planarizing properties and adhesion to a substrate; and a material for forming an organic film containing the compound. Moreover, this material for forming an organic film has high filling and planarizing properties and adhesion to a substrate, and is also a material for forming an organic film provided with other characteristics such as heat resistance and etching resistance. Accordingly, the material for forming an organic film is extremely useful as a resist underlayer film material in a multilayer resist process such as a 2-layer resist process, a 3-layer resist process using a middle layer film containing a silicon atom, or a 4-layer resist process using a middle layer film containing a silicon atom and an organic antireflective coating, or as a planarizing material for manufacturing a semiconductor device, for example.

In addition, according to the inventive method for forming an organic film, a sufficiently cured and flat organic film can be formed on a substrate to be processed. Furthermore, according to the inventive patterning process, a fine pattern can be formed with high precision on a substrate to be processed in a multilayer resist process.

BRIEF DESCRIPTION OF DRAWINGS

FIG. 1 is an explanatory diagram of an example of an inventive patterning process according to a 3-layer resist process.

FIG. 2 is an explanatory diagram of a method for evaluating the filling property in Examples and Comparative Examples.

FIG. 3 is an explanatory diagram of a method for evaluating the planarizing property in Examples and Comparative Examples.

FIG. 4 is an explanatory diagram showing a method for measuring the adhesiveness in Examples.

DESCRIPTION OF EMBODIMENTS

As described above, a material for forming an organic film for forming an organic film having high filling and planarizing properties and adhesion to a substrate has been desired.

The present inventors have earnestly studied the above problems and found out that a material for forming an organic film containing a compound shown by the following general formula (1) can form an organic film having high filling and planarizing properties and excellent adhesion to a substrate, and thus completed the present invention.

That is, the present invention is a material for forming an organic film, containing: a compound shown by the following general formula (1); and an organic solvent,

where in the general formula (1), X represents an organic group with a valency of "n" having 2 to 50 carbon atoms or an oxygen atom, "n" represents an integer of 1 to 10, and $R_1$ independently represents any of the following general formulae (2),

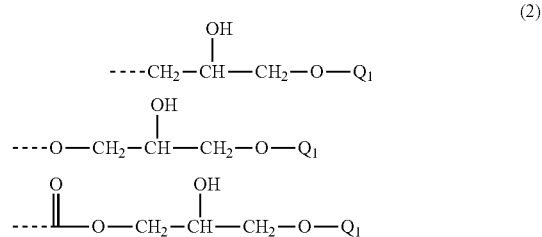

where in the general formulae (2), broken lines represent attachment points to X, and $Q_1$ represents a monovalent organic group containing a carbonyl group, at least a part of which is a group shown by the following general formulae (3),

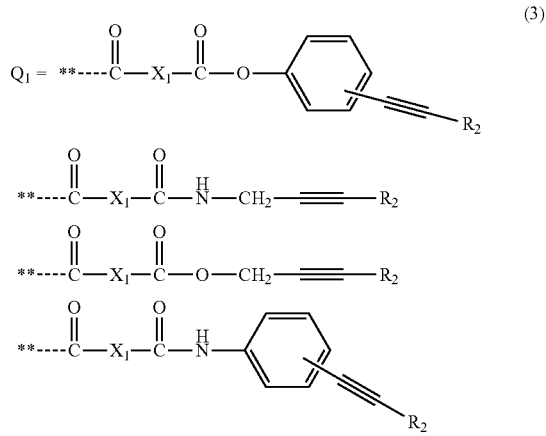

where in the general formulae (3), broken lines represent attachment points, $X_1$ represents a single bond or a divalent organic group having 1 to 20 carbon atoms optionally having a substituent when the organic group has an aromatic ring, $R_2$ represents a hydrogen atom, a methyl group, an ethyl group, or a phenyl group, and ** represents an attachment point.

Hereinafter, embodiments of the present invention will be described, but the present invention is not limited thereto. Note that the inventive material for forming an organic film is sometimes referred to as an organic film material or a composition for forming an organic film, hereinafter.

[Compound for Forming Organic Film]

The inventive compound is shown by the following general formula (1), $$X\text{---}(R_1)_n \quad (1)$$

where in the general formula (1), X represents an organic group with a valency of "n" having 2 to 50 carbon atoms or an oxygen atom, "n" represents an integer of 1 to 10, and $R_1$ independently represents any of the following general formulae (2),

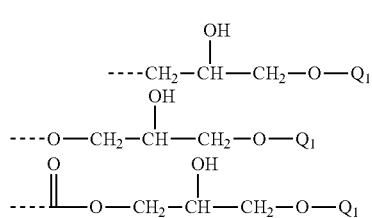

(2)

where in the general formulae (2), broken lines represent attachment points to X, and $Q_1$ represents a monovalent organic group containing a carbonyl group, at least a part of which is a group shown by the following general formulae (3),

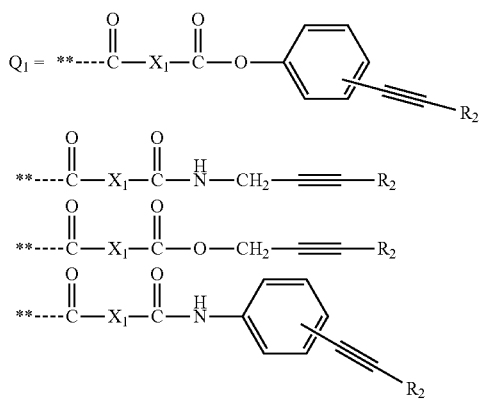

(3)

where in the general formulae (3), broken lines represent attachment points, $X_1$ represents a single bond or a divalent organic group having 1 to 20 carbon atoms optionally having a substituent when the organic group has an aromatic ring, $R_2$ represents a hydrogen atom, a methyl group, an ethyl group, or a phenyl group, and ** represents an attachment point.

Specific examples of the compound shown by the general formula (1) include the following (parts excluding $R_1$ are X). In the following formulae, $R_1$ has the same meaning as defined above. m1 and m2 each independently represent an integer of 0 to 4, and m1+m2 is 1 or more to 8 or less. n9 represents an integer of 0 to 3. Here, $R_1$ each independently represents any of the general formulae (2), and all the $R_1$s may be the same.

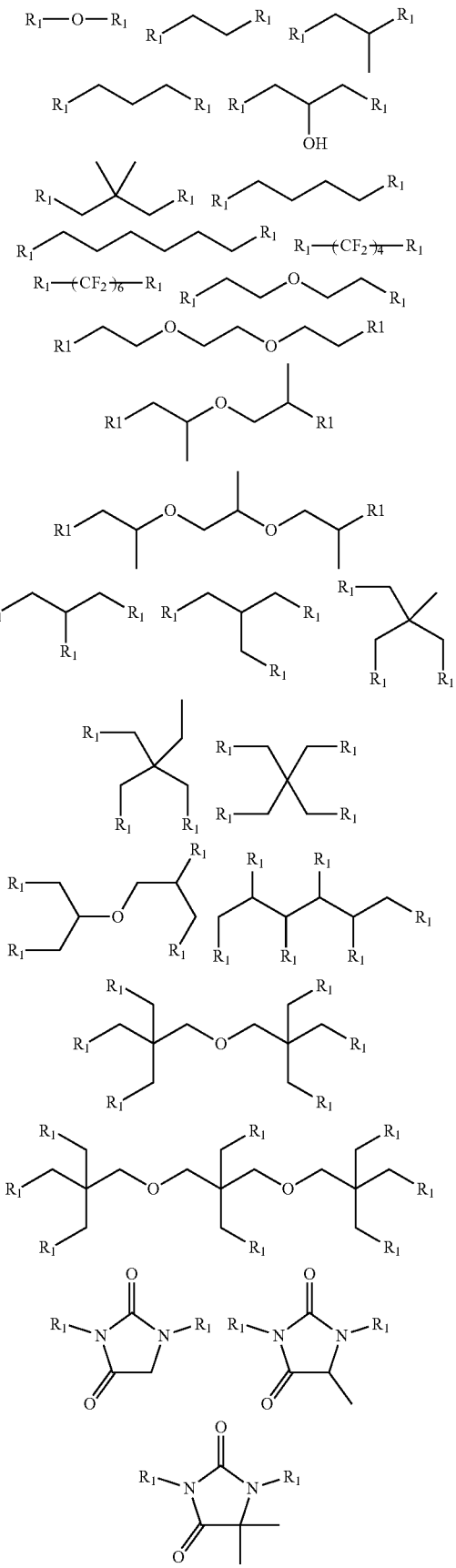

-continued
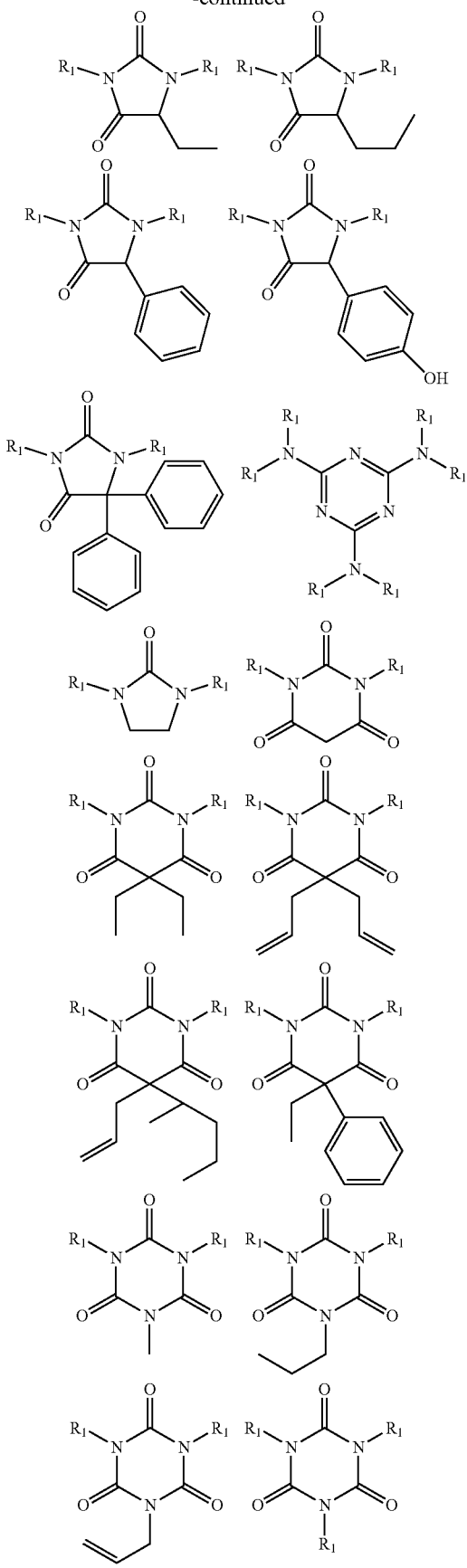
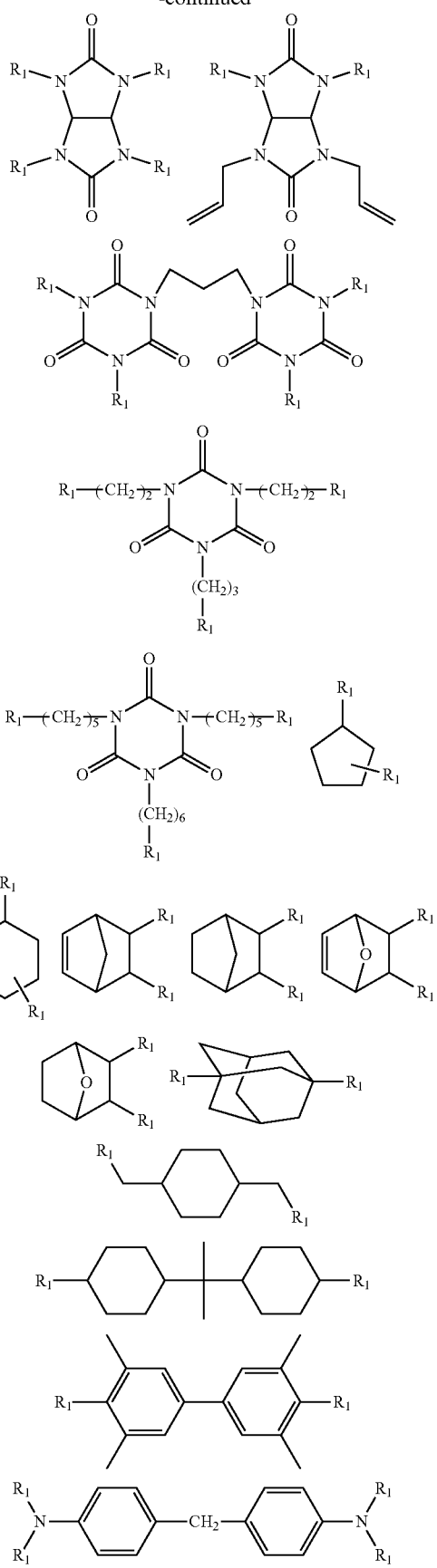

-continued
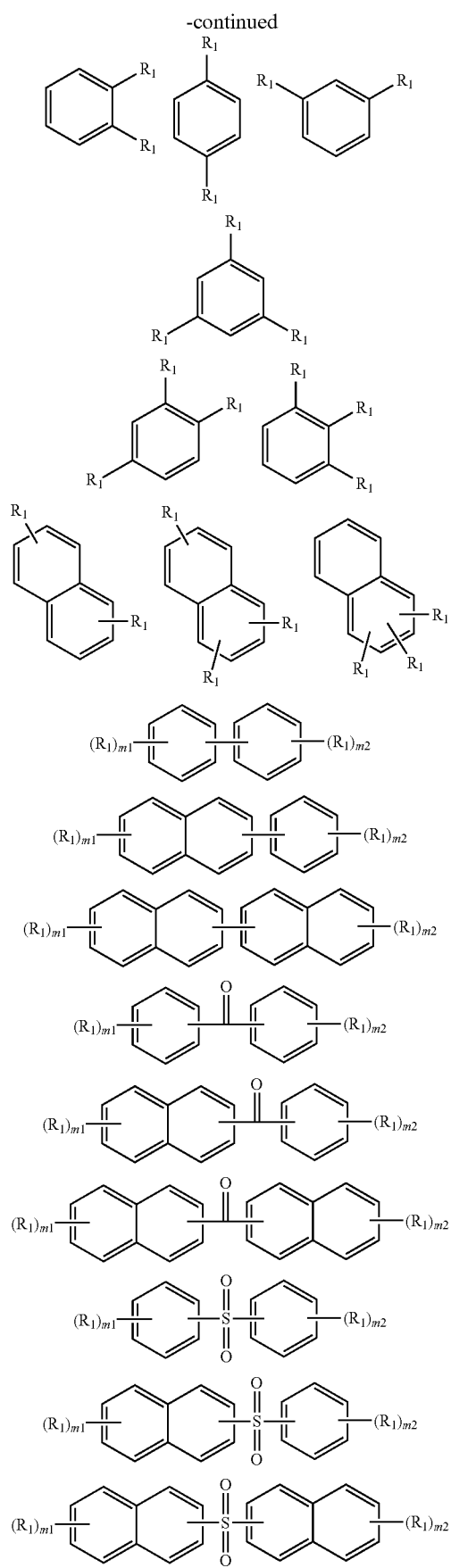
-continued
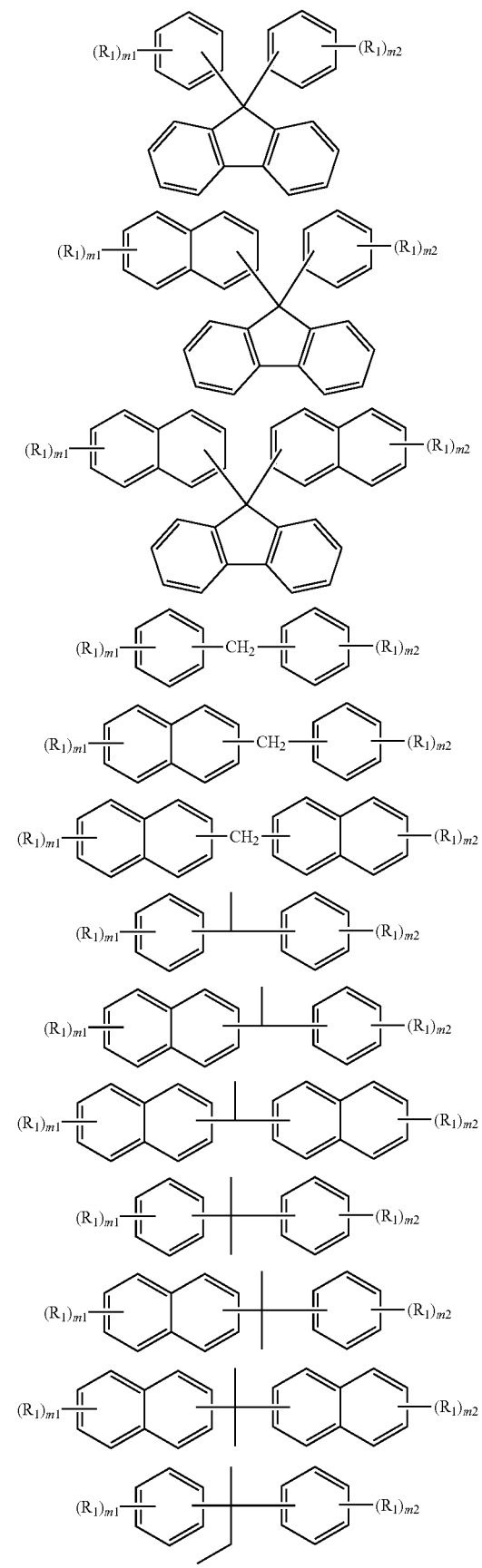

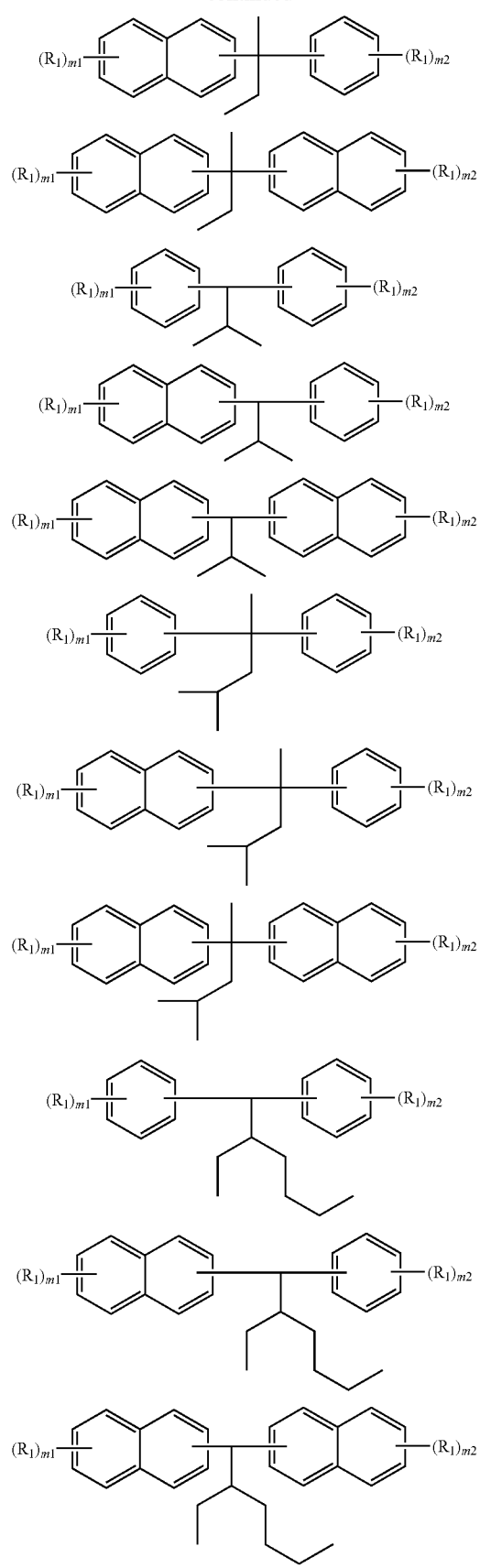
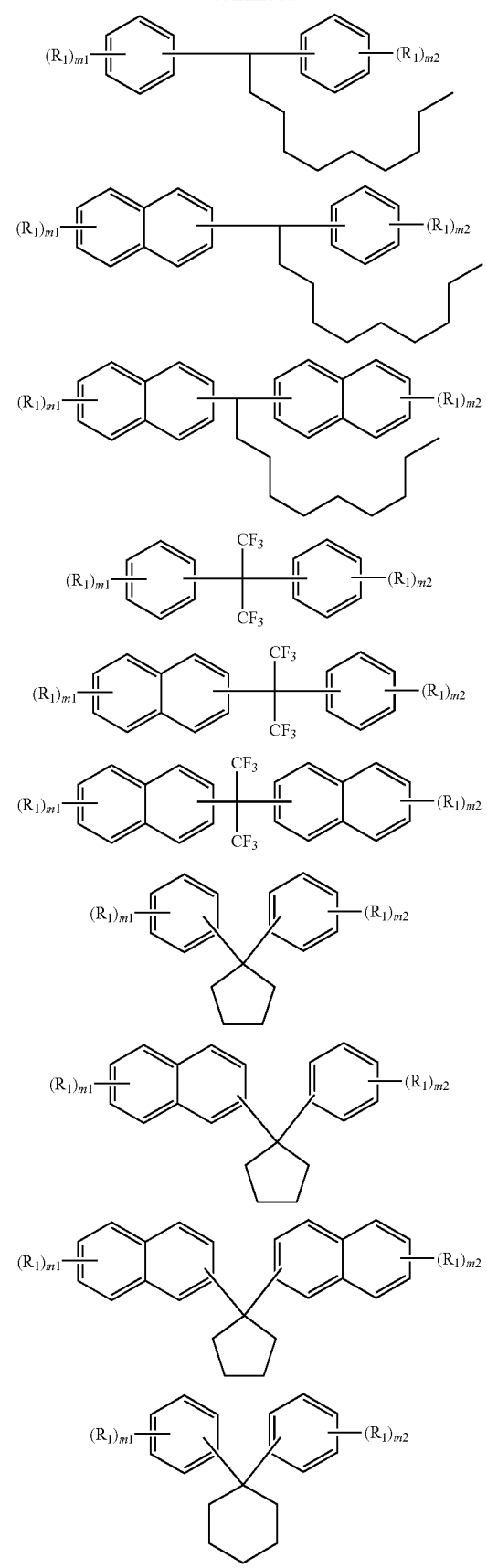

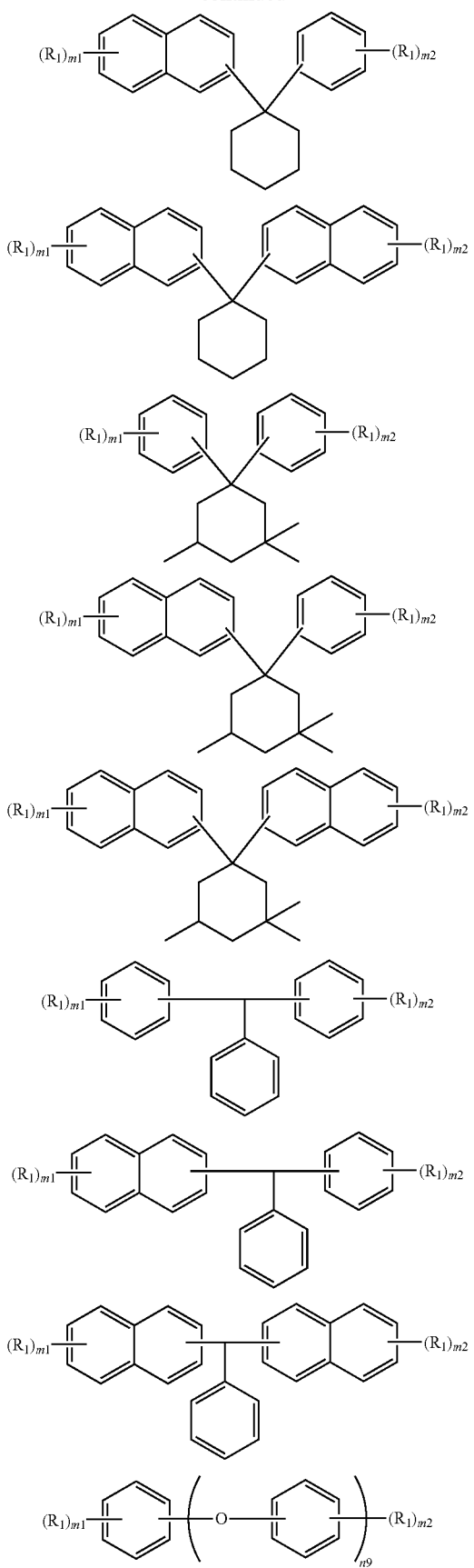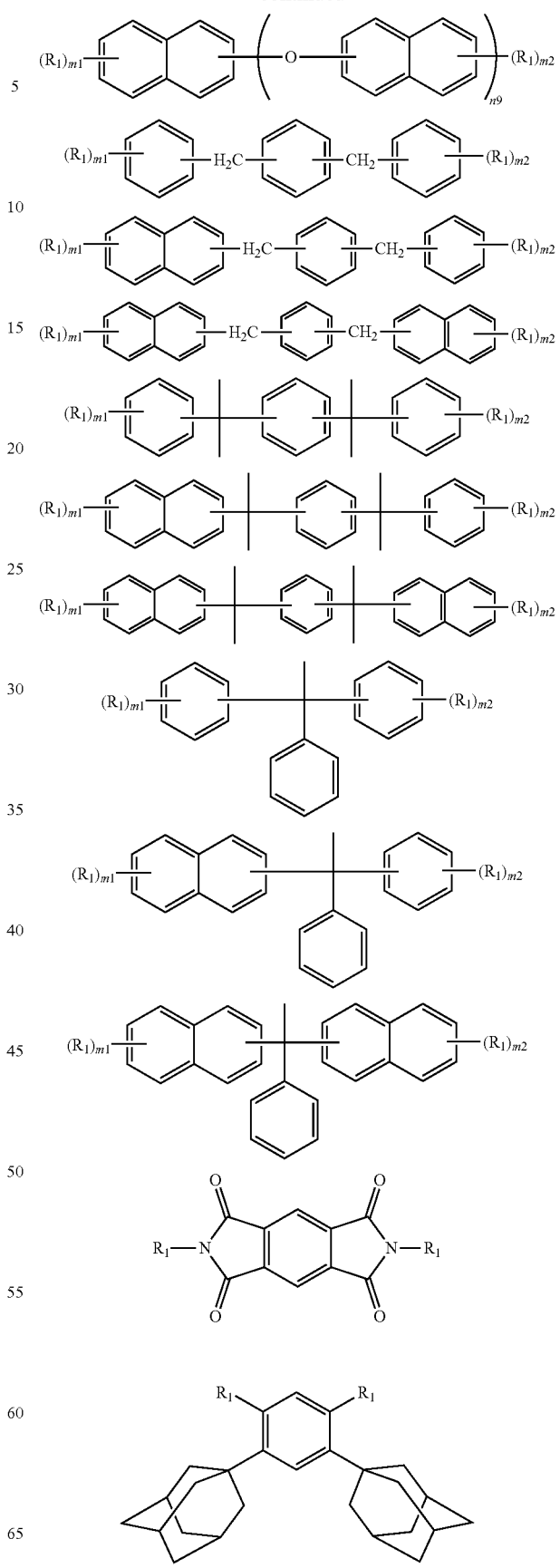

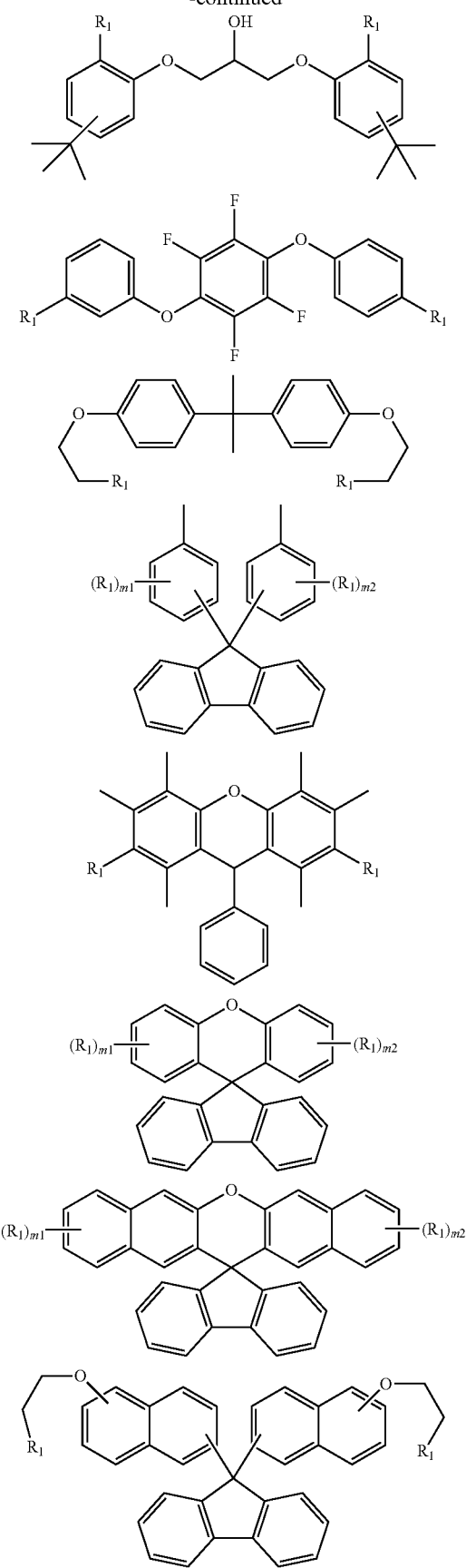
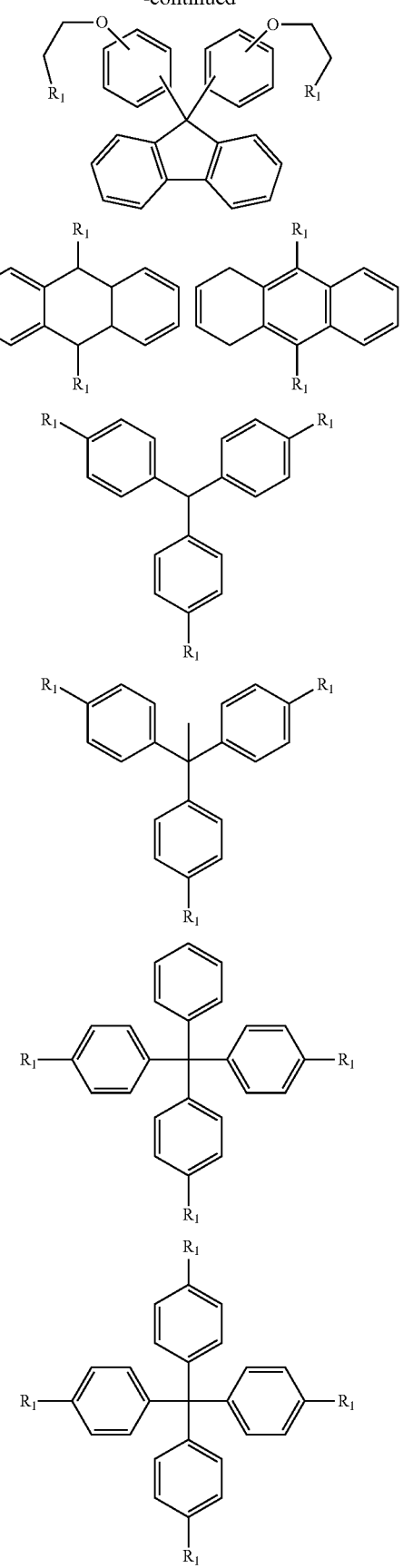

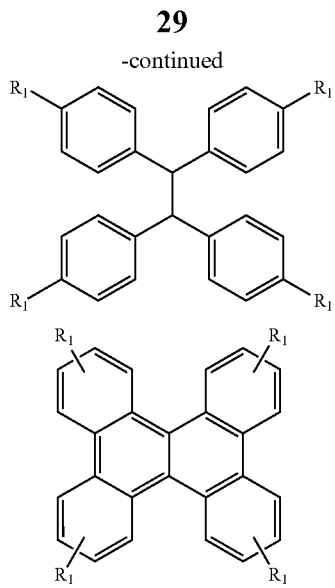

Furthermore, specific examples of $X_1$ in the general formulae (3) include the following.

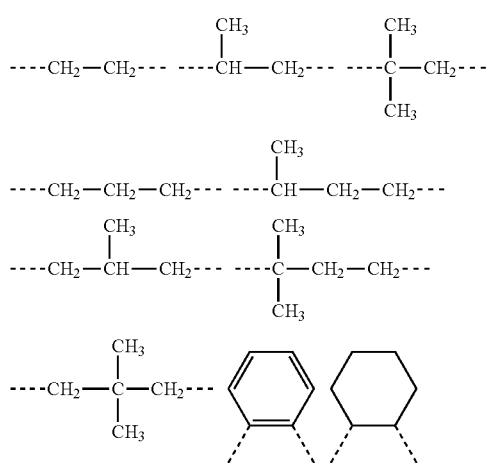

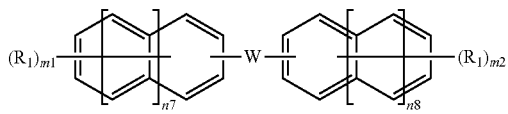

(The broken lines represent attachment points.)

In this event, the compound of the general formula (1) is preferably a compound shown by the following general formulae (4), (6), (7), (8), (9), (10), (11), (12), (13), and (14).

(4)

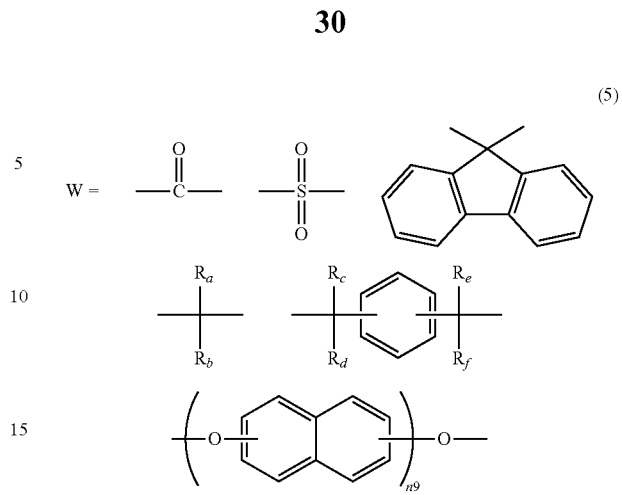

(In the general formula (4), n7 and n8 each independently represent 0 or 1, and W represents a single bond or any structure shown by the following (5). $R_1$ has the same meaning as defined above, m1 and m2 each independently represent an integer of 0 to 4, and m1+m2 is 1 or more to 8 or less.)

(5)

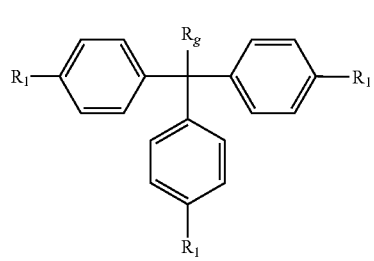

(In the general formulae (5), n9 represents an integer of 0 to 3, $R_a$ to $R_f$ each independently represent a hydrogen atom or an optionally fluorine-substituted alkyl group having 1 to 10 carbon atoms or phenyl group, and $R_a$ and $R_b$ are optionally bonded with each other to form a ring.)

(6)

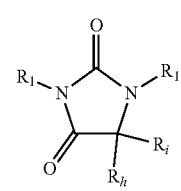

(In the general formula (6), $R_g$ represents a hydrogen atom, a methyl group, or a phenyl group.)

(7)

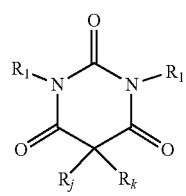

(8)

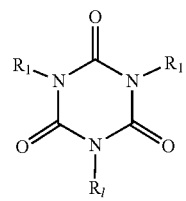

(9)

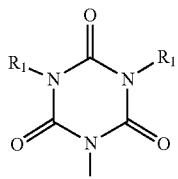 (10)

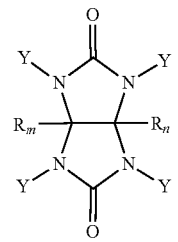 (11)

(In the general formulae (7) to (11), $R_1$ has the same meaning as defined above, $R_h$, $R_i$, $R_j$, $R_k$, $R_l$, $R_m$, and $R_n$ each represent a hydrogen atom, an alkyl group having 1 to 10 carbon atoms, an alkynyl group having 2 to 10 carbon atoms, an alkenyl group having 2 to 10 carbon atoms, or a benzyl group or a phenyl group optionally having a substituent on an aromatic ring. Y represents $R_1$, a hydrogen atom, an alkyl group having 1 to 10 carbon atoms, an alkynyl group having 2 to 10 carbon atoms, or an alkenyl group having 2 to 10 carbon atoms, and at least two of the four Ys in the general formula (11) represent $R_1$.)

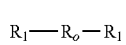 (12)

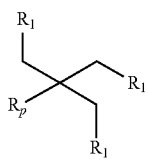 (13)

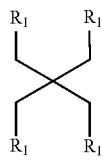 (14)

(In the general formulae (12) to (14), $R_1$ has the same meaning as defined above, $R_o$ in the general formula (12) represents a linear saturated or unsaturated divalent hydrocarbon group having 1 to 20 carbon atoms or a branched or cyclic saturated or unsaturated divalent hydrocarbon group having 3 to 20 carbon atoms, and $R_p$ in the general formula (13) represents a hydrogen atom or an alkyl group having 1 to 10 carbon atoms.)

As the compound shown by the general formula (4), the following are particularly favorable from the viewpoints of heat resistance and etching resistance.

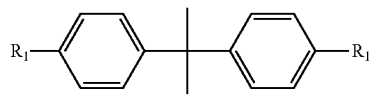

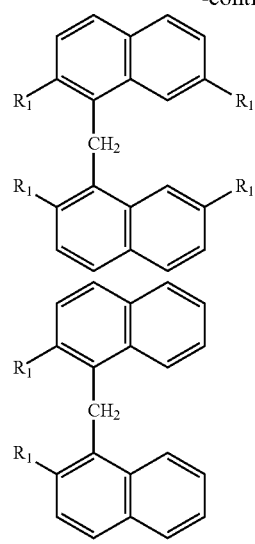

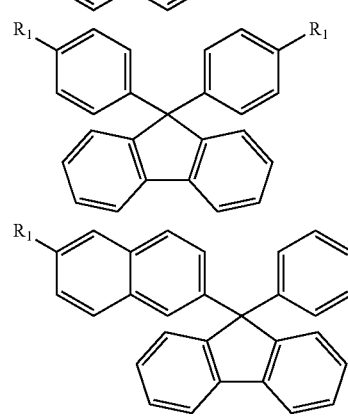

As the compound shown by the general formula (6), the following are particularly favorable from the viewpoints of heat resistance, etching resistance, and curability.

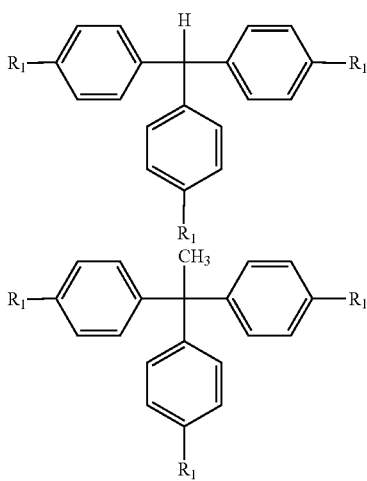

In the present invention, the following are particularly favorable among the compounds shown by the general formulae (7) to (11) from the viewpoints of etching resistance, optical characteristics, and adhesiveness.

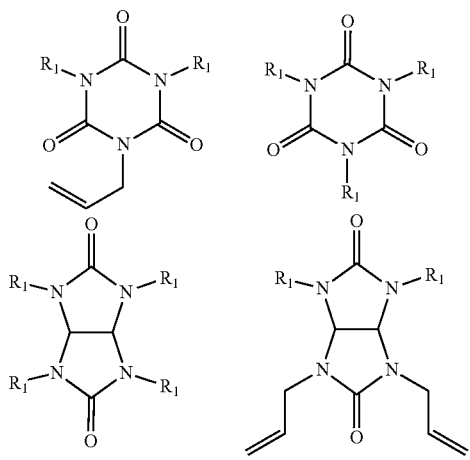

In the present invention, the following are particularly favorable among the compounds shown by the general formulae (12) to (14) from the viewpoints of high filling property, planarizing, and adhesiveness.

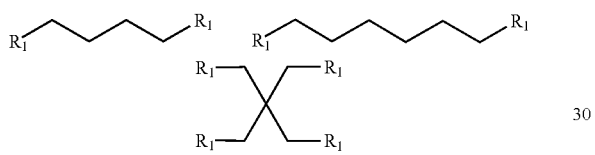

In addition, $Q_1$ in the general formula (2) can include any one or more shown by the general formulae (3) and any one or more shown by the following general formulae (15) and (16).

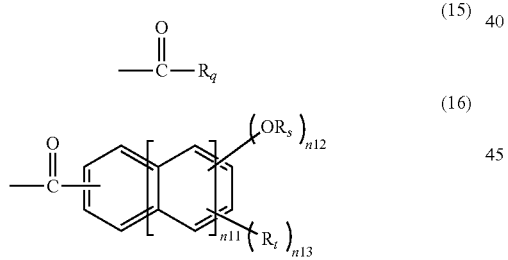

($R_q$ in the general formula (15) represents a linear saturated or unsaturated hydrocarbon group having 1 to 30 carbon atoms or a branched or cyclic saturated or unsaturated hydrocarbon group having 3 to 30 carbon atoms, and a methylene group included in $R_q$ is optionally substituted with an oxygen atom or a carbonyl group. In the general formula (16), $R_s$ represents a hydrogen atom, a linear hydrocarbon group having 1 to 10 carbon atoms, or a branched hydrocarbon group having 3 to 10 carbon atoms, and $R_t$ represents a linear hydrocarbon group having 1 to 10 carbon atoms, a branched hydrocarbon group having 3 to 10 carbon atoms, a halogen atom, a nitro group, an amino group, a nitrile group, an alkoxycarbonyl group having 1 to 10 carbon atoms, or an alkanoyloxy group having 1 to 10 carbon atoms. n11 represents 0 to 2, n12 and n13 represent a number of substituents on the aromatic ring, n12 and n13 represent an integer of 0 to 7, and n12+n13 is 0 or more to 7 or less.)

Examples of the terminal group structure shown by the general formula (15) include the following. In the following formulae, n14 represents an integer of 0 to 30, and n15 represents an integer of 0 to 20.

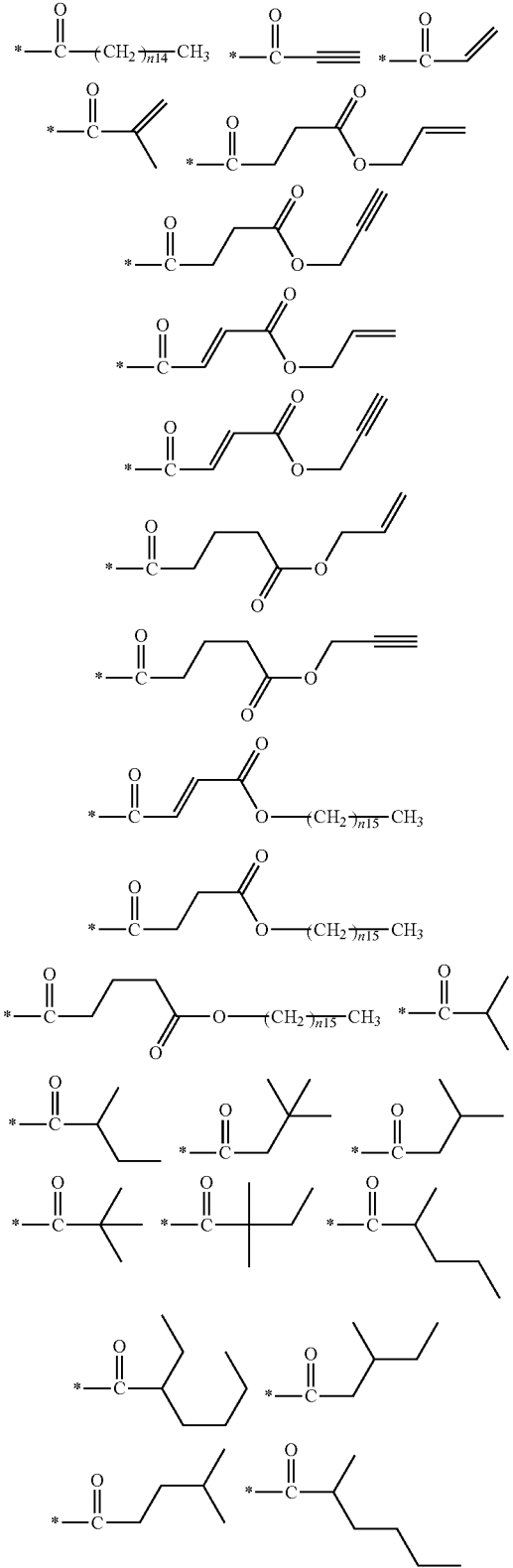

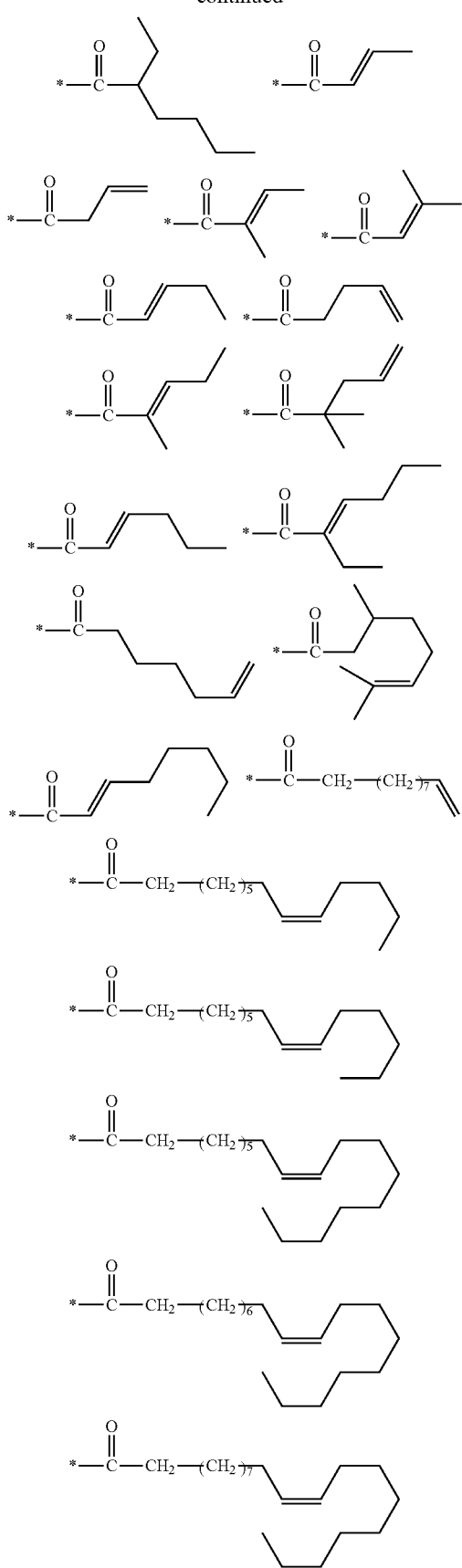
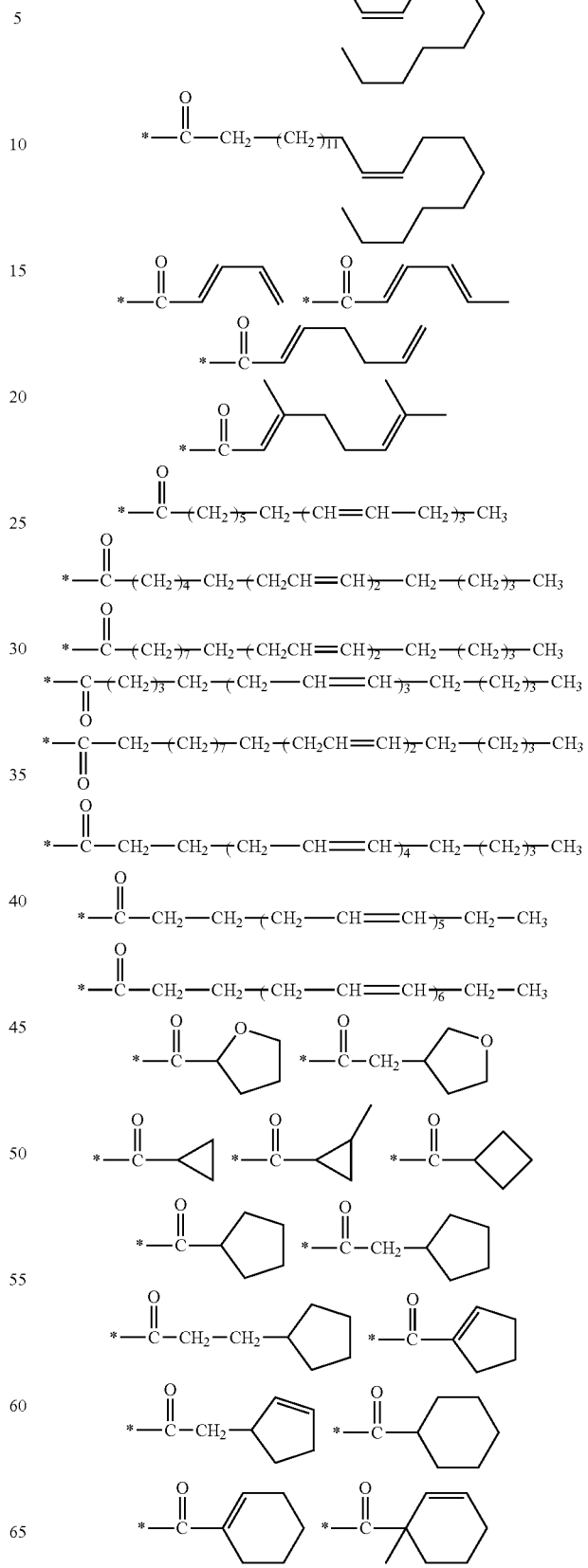

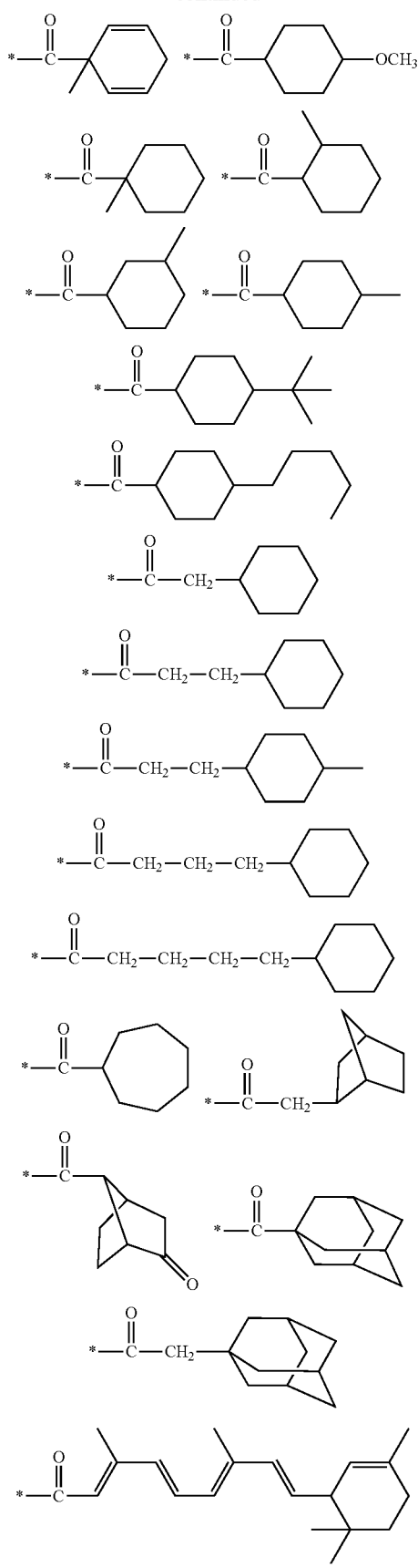
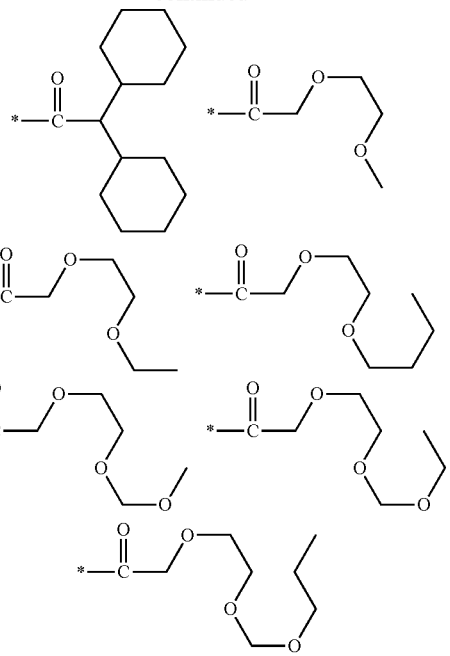
Examples of the terminal group structure shown by the general formula (16) include the following. n16 in the following formulae represent an integer of 0 to 9.
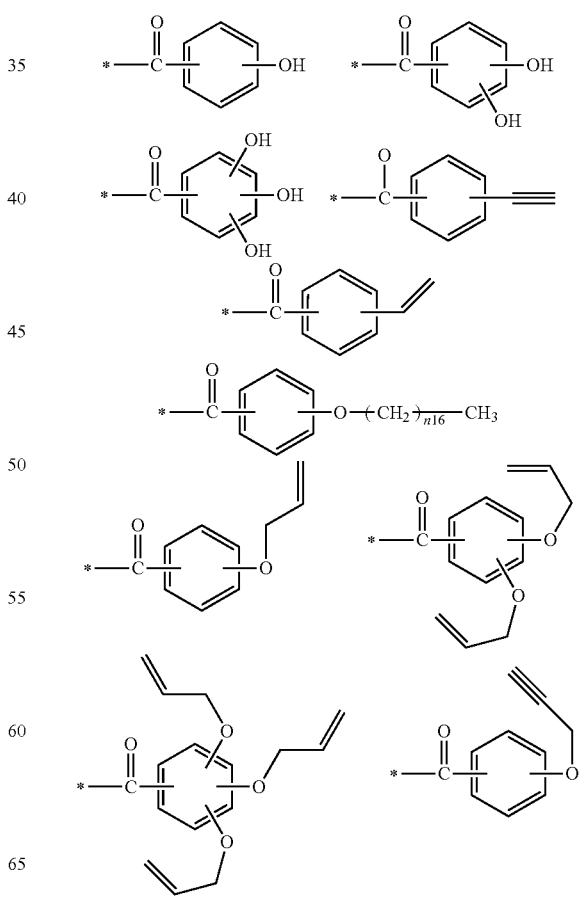

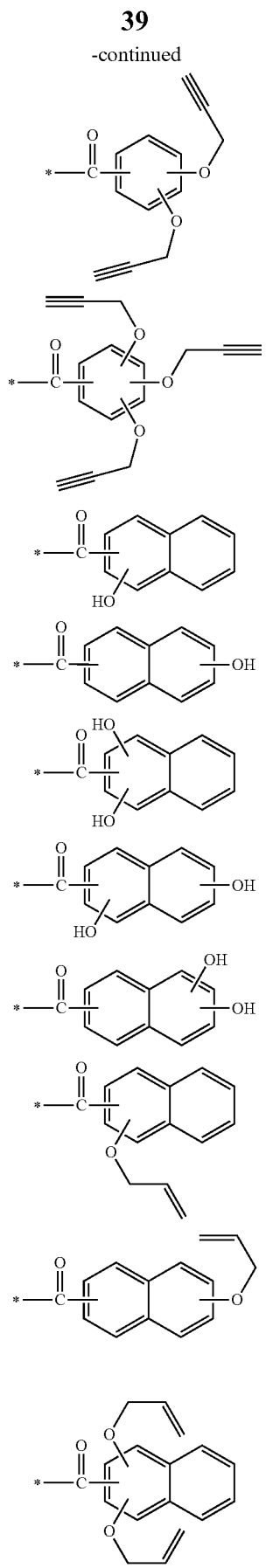
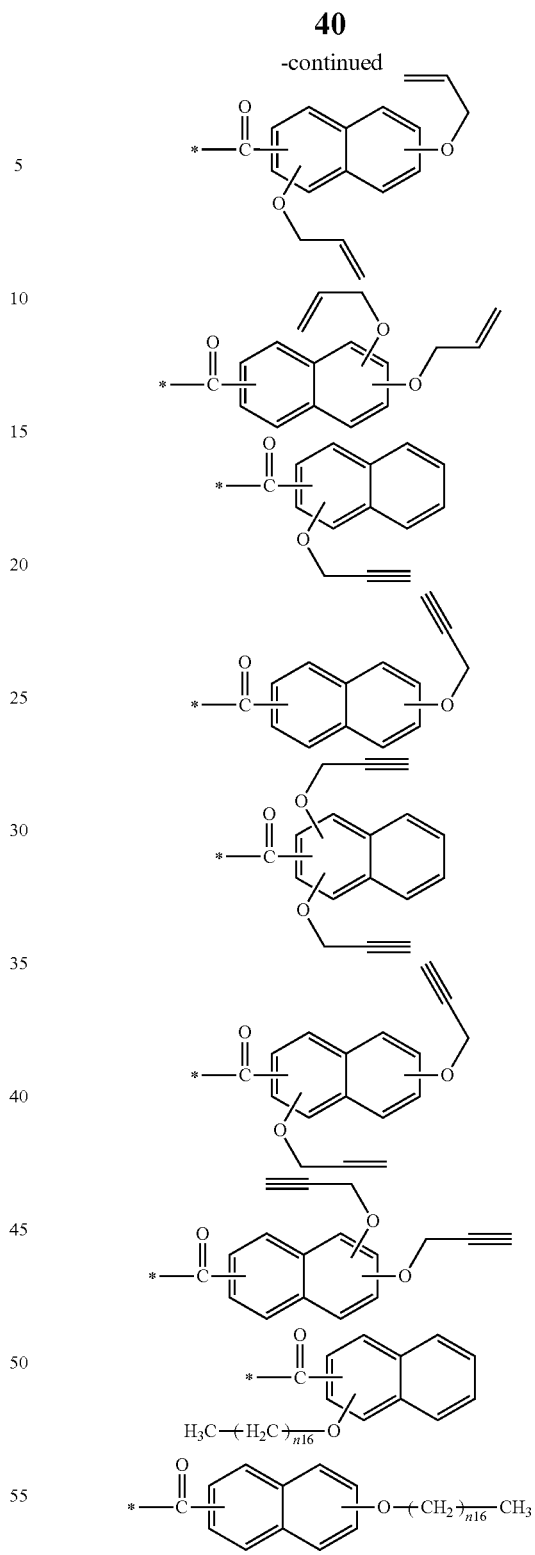

A material for forming an organic film containing these compounds makes it possible to adjust various physical properties such as heat resistance, etching resistance, high filling and planarizing properties, and adhesion to a substrate according to the required performance by combining the terminal group structures. In addition, since an optical constant can also be controlled, it becomes possible to provide an appropriate optical constant particularly at the time of exposure in multilayer ArF lithography, and reflected light can be suppressed so that an excellent resolution can be achieved.

In addition, when a material for forming an organic film containing such a compound is used as a resist underlayer film material used for forming a multilayer resist film applied in fine processing in a manufacturing process of a semiconductor device, etc., a resist underlayer film material for forming a resist underlayer film having high filling and planarizing properties and adhesion to a substrate, a method for forming a resist underlayer film, and a patterning process can be provided. In addition, in the present invention, a planarizing material for manufacturing a semiconductor device that can be applied for planarizing in a semiconductor device manufacturing process other than a multilayer resist process and that has high filling and planarizing properties and adhesion to a substrate can also be provided.

[Method for Manufacturing Compound]

The compound (compound for an organic film material) used in the inventive material for forming an organic film can be manufactured by selecting the optimum method according to the structure of the compound. Hereinafter, an example of a method for synthesizing the compound for an organic film material shown by the general formula (1) will be described in detail. Note that the method for manufacturing a compound for organic film material is not limited thereto.

Specific examples of the manufacturing method include a method including: a first step of obtaining a carboxylic acid compound shown by any of the following general formulae (17) by an addition reaction between a carboxylic acid anhydride shown by $(X_1CO)_2O$ and an alcohol or an amine; and

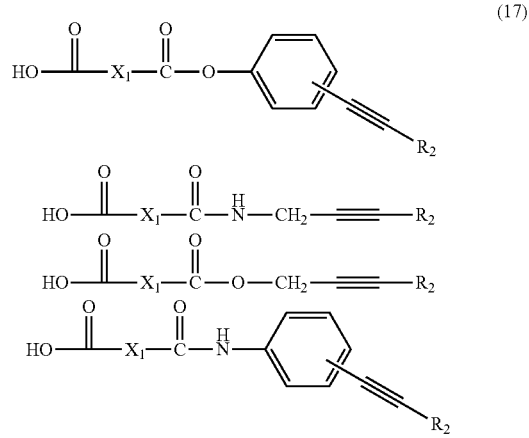

(in the general formulae (17), $X_1$ and $R_2$ have the same meanings as defined above)

a second step of obtaining a compound for an organic film material shown by the general formula (1) by an addition reaction between an epoxy compound shown by the following general formula (18) and a carboxylic acid compound (monocarboxylic acid) shown by the general formulae (17).

(In the general formula (18), X and "n" have the same meanings as defined above, and $R_3$ represents any of the following general formulae (19).)

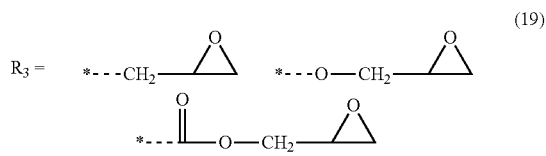

(In the general formulae (19), the broken lines represent attachment points to X.)

In the reaction between the carboxylic acid anhydride and the alcohol or the amine in the first step, the used amount of the alcohol or the amine is preferably 0.5 to 1.5 mol, more preferably 0.7 to 1.3 mol, and further preferably 0.8 to 1.2 mol per 1 mol of the carboxylic acid anhydride.

The first step can be performed by mixing the raw materials in a solvent or without a solvent by cooling or heating. When a solvent is used in the reaction, specific examples of the solvent include: alcohols such as methanol, ethanol, isopropyl alcohol, butanol, ethylene glycol, propylene glycol, diethylene glycol, glycerol, methyl cellosolve, ethyl cellosolve, butyl cellosolve, and propyleneglycolmonomethyl ether; ethers such as diethyl ether, dibutyl ether, diethyleneglycoldiethyl ether, diethyleneglycoldimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethylmethyl ketone, and isobutylmethyl ketone; esters such as ethyl acetate, n-butyl acetate, and propyleneglycolmethyl ether acetate; lactones such as γ-butyrolactone; and non-protic polar solvents such as dimethylsulfoxide, N,N-dimethylformamide, and hexamethylphosphoric triamide. These can be used alone or in mixture of two or more thereof. These solvents can be used within a range of 0 to 2,000 parts by mass based on 100 parts by mass of the starting material.

For these syntheses, a base catalyst can be used as necessary, and examples of the base catalyst include: inorganic base compounds such as sodium hydrogen carbonate, sodium carbonate, potassium carbonate, calcium carbonate, cesium carbonate, sodium hydroxide, potassium hydroxide, sodium hydride, and potassium phosphate; organic bases such as triethyl amine, diisopropyl ethyl amine, N,N-dimethylaniline, pyridine, and 4-dimethylaminopyridine; and the like. These can be used alone or in combination of two or more thereof. The amount of the catalyst used is preferably within the range of 0.001 to 100 mass % based on the total amount of the starting material, more preferably 0.005 to 50 mass %.

The reaction temperature is preferably −20° C. to 200° C., more preferably 0° C. to 150° C. When a solvent is used, it is preferable to set the upper limit of the reaction temperature to approximately the boiling point of the solvent. When the reaction temperature is −20° C. or higher, there is no risk of the reaction being slowed down, and when the reaction temperature is 200° C. or lower, side reactions such as a decomposition reaction of a product do not easily occur. The reaction time of the above reaction is usually about 0.5 to 200 hours, and it is preferable to determine the reaction time by tracing the progress of the reaction by thin-layer chromatography, liquid chromatography, gel filtration chromatography, or the like to improve the yield. After completion of the reaction, a usual aqueous post-treatment (aqueous work-up) can be performed as necessary to obtain the compound shown by the formulae (17). The compound shown by the formulae (17) can be refined by a usual method such as crystallization, liquid separation, chromatography, and adsorption treatment according to the properties of the compound if necessary. In some cases, it is also possible to proceed directly to the second step without any additional treatments after the reaction.

As methods for performing the reaction, for example, it is possible to adopt a method of charging the raw materials, reaction catalyst, and if necessary, a solvent at once, or a method of adding the raw materials or raw material solution dropwise alone or in mixture in the presence of a reaction catalyst.

In the reaction between the epoxy compound and the carboxylic acid compound in the second step, the used amount of the carboxylic acid is preferably 0.3 to 2.0 mol, more preferably 0.5 to 1.5 mol, and further preferably 0.75 to 1.25 mol per 1 mol of the epoxy in the epoxy compound. When the used amount of the carboxylic acid is appropriate relative to the epoxy unit as described, there is no risk of unreacted epoxy group remaining and degrading the storage stability of the organic film material, and it is possible to prevent unreacted carboxylic acid from remaining and causing outgassing.

Additionally, in the reaction between the epoxy compound and the carboxylic acid compound, a plurality of carboxylic acid compounds can also be used at the same time within the range of the used amount of the carboxylic acid to improve the required performance such as optical constant (n/k), thermal flowability, etching resistance, heat resistance, solvent solubility, and adhesion to a substrate. As such a combination of carboxylic acid compounds, the carboxylic acid compounds shown by any of the general formulae (17) can be combined, and it is particularly preferable to combine a carboxylic acid compound (carboxylic acid compound (20)) shown by the following general formula (20) and a carboxylic acid compound (carboxylic acid compound (21)) shown by the following general formula (21) at the same time. It is also possible to combine a plurality of carboxylic acid compounds (20) and carboxylic acid compounds (21) at the same time. The used amount of the carboxylic acid compound (20) and the carboxylic acid compound (21) when used at the same time can each be adjusted within the range of 1 to 99 mol % when the total amount of used carboxylic acid is set to 100 mol %. 20 mol % or more of the carboxylic acid compound (21) is preferably used, more preferably 30 mol % or more from the viewpoints of etching resistance and heat resistance.

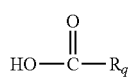
(20)

(In the formula, $R_q$ has the same meaning as defined above.)

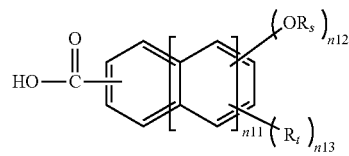
(21)

(In the formula, $R_s$, $R_t$, n11, n12, and n13 have the same meanings as defined above.)

The above-described compound can usually be obtained by allowing an epoxy compound and a carboxylic acid compound to react, without a solvent or in a solvent in the presence of a reaction catalyst in room temperature or under cooling or heating as necessary. When a solvent is used in the reaction, specific examples of the solvent to be used include: alcohols such as methanol, ethanol, isopropyl alcohol, butanol, ethylene glycol, propylene glycol, diethylene glycol, glycerol, methyl cellosolve, ethyl cellosolve, butyl cellosolve, and propyleneglycolmonomethyl ether; ethers such as diethyl ether, dibutyl ether, diethyleneglycoldiethyl ether, diethyleneglycoldimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethylmethyl ketone, and isobutylmethyl ketone; esters such as ethyl acetate, n-butyl acetate, and propyleneglycolmethyl ether acetate; lactones such as γ-butyrolactone; and non-protic polar solvents such as dimethylsulfoxide, N,N-dimethylformamide, and hexamethylphosphoric triamide. These can be used alone or in mixture of two or more thereof. These solvents can be used within a range of 0 to 2,000 parts by mass based on 100 parts by mass of the starting material.

Specific examples of the reaction catalyst include: quaternary ammonium salts such as benzyltriethylammonium chloride, benzyltriethylammonium bromide, benzyltrimethylammonium chloride, tetramethylammonium chloride, tetramethylammonium bromide, tetramethylammonium iodide, tetramethylammonium hydroxide, tetraethylammonium bromide, tetrabutylammonium chloride, tetrabutylammonium bromide, tetrabutylammonium iodide, tetrabutylammonium hydrogensulfate, tri octylmethylammonium chloride, tributylbenzylammonium chloride, trimethylbenzylammonium chloride, trimethylbenzylammonium hydroxide, N-laurylpyridinium chloride, N-lauryl-4-picolinium chloride, N-laurylpicolinium chloride, trimethylphenylammonium bromide, and N-benzylpicolinium chloride; quaternary phosphonium salts such as tetrabutylphosphonium chloride, tetrabutylphosphonium bromide, and tetraphenylphosphonium chloride; and tertiary amines such as tris[2-(2-methoxyethoxy)ethyl]amine, tris(3,6-dioxaheptyl)amine, and tris(3,6-dioxaoctyl)amine. The amount of the catalyst to be used is preferably in the range of 0.001 to 100 mass %, more preferably 0.005 to 50 mass % based on the total amount of the starting material.

The reaction temperature is preferably −50° C. to approximately the boiling point of the solvent, more preferably room temperature to 150° C. The reaction time can be appropriately selected from 0.1 to 100 hours.

The reaction method includes: a method where the epoxy compound, the carboxylic acid compound, and the catalyst are charged at once; a method of dispersing or dissolving the epoxy compound and the carboxylic acid compound, then adding the catalyst at once or diluting with a solvent and adding dropwise; and a method of dispersing or dissolving the catalyst, then adding the epoxy compound and the carboxylic acid compound at once or diluting with a solvent and adding dropwise.

After completion of the reaction in each step, the resultant may be used directly as an organic film material, but may also be diluted with an organic solvent, then subjected to liquid separation and washing to remove unreacted raw materials, the catalyst, and so on present in the system, and thus collected.

The organic solvent used in this event is not particularly limited, as long as the organic solvent is capable of dissolving the compounds and is separated into two layers when mixed with water. The organic solvent includes: hydrocarbons such as hexane, heptane, benzene, toluene, and xylene; esters such as ethyl acetate, n-butyl acetate, and propylene glycol methyl ether acetate; ketones such as methyl ethyl ketone, methyl amyl ketone, cyclohexanone, and methyl isobutyl ketone; ethers such as diethyl ether, diisopropyl ether, methyl-tert-butyl ether, and ethylcyclopentylmethyl ether; chlorinated solvents such as methylene chloride, chloroform, dichloroethane, and trichloroethylene; mixtures thereof; and the like. As washing water used in this event, generally, what is called deionized water or ultrapure water may be used. The washing may be performed once or more, preferably approximately once to five times because washing ten times or more does not always produce the full washing effects thereof.

In the liquid separation and washing, the washing may be performed with a basic aqueous solution to remove the unreacted carboxylic acid or acidic components in the system. The base specifically includes hydroxides of alkaline metals, carbonates of alkaline metals, hydroxides of alkali earth metals, carbonates of alkali earth metals, ammonia, organic ammonium, and the like.

Further, in the liquid separation and washing, the washing may be performed with an acidic aqueous solution to remove the metal impurities or basic components in the system. The acid specifically includes: inorganic acids such as hydrochloric acid, hydrobromic acid, sulfuric acid, nitric acid, phosphoric acid, and heteropoly acid; organic acids such as oxalic acid, trifluoroacetic acid, methanesulfonic acid, benzenesulfonic acid, p-toluenesulfonic acid, and trifluoromethanesulfonic acid; and the like.

The liquid separation and washing may be performed with any one of the basic aqueous solution and the acidic aqueous solution, or can be performed with a combination of the two. The liquid separation and washing is preferably performed with the basic aqueous solution and the acidic aqueous solution in this order from the viewpoint of removing the metal impurities.

After the liquid separation and washing with the basic aqueous solution and the acidic aqueous solution, washing with neutral water may be successively performed. The washing may be performed once or more, preferably approximately once to five times. As the neutral water, deionized water, ultrapure water, or the like as mentioned above may be used. The washing may be performed once or more, but if the washing is not performed sufficiently, the basic components and acidic components cannot be removed in some cases. The washing is preferably performed approximately once to five times because washing ten times or more does not always produce the full washing effects thereof.

Further, the reaction product after the liquid separation can also be collected as a powder by concentrating and drying the solvent or crystallizing the reaction product under reduced pressure or normal pressure. Alternatively, the reaction product can also be retained in the state of solution with an appropriate concentration to improve the workability in preparing the organic film material. The concentration in this event is preferably 0.1 to 50 mass %, more preferably 0.5 to 30 mass %. With such a concentration, the viscosity is hardly increased, making it possible to prevent deterioration of the workability; in addition, since the amount of the solvent is not excessive, it is economical.

The solvent in this event is not particularly limited, as long as the solvent is capable of dissolving the compound. Specific examples of the solvent include ketones such as cyclohexanone and methyl-2-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxy propionate, tert-butyl acetate, tert-butyl propionate, and propylene glycol mono-tert-butyl ether acetate. These can be used alone or in mixture of two or more thereof.

As described, the inventive compound for an organic film material can be manufactured easily, and can be used suitably for the above-described inventive material for forming an organic film.

[Material for Forming Organic Film]

The present invention provides a material for forming an organic film containing: (A) the above-described compound; and (B) an organic solvent. Note that in the inventive material for forming an organic film, the above-described compound (A) may be used alone or in combination of two or more thereof.

The organic solvent (component (B)) used in the inventive material for forming an organic film is not particularly limited, but solvents that dissolve the base polymer, acid generator, crosslinking agent, other additives and the like are preferable. Specifically, solvents with a boiling point of lower than 180° C. such as those disclosed in paragraphs (0091) to (0092) of JP 2007-199653 A can be used. Above all, propylene glycol monomethyl ether acetate, propylene glycol monomethyl ether, 2-heptanone, cyclopentanone, cyclohexanone, and a mixture of two or more thereof are preferably used. The solvent may also be the same as or different from the solvent used in manufacturing the above-described component (A).

Such a composition can be applied by spin-coating, and a material for forming an organic film (composition for forming an organic film) having favorable dry etching resistance as well as heat resistance and high filling and planarizing properties can be achieved because the inventive compound for forming an organic film as described above is incorporated.

Furthermore, the inventive material for forming an organic film may use the organic solvent with one or more high-boiling-point solvents having a boiling point of 180° C. or higher added to the above-described solvent having a boiling point of lower than 180° C. (a mixture of the solvent having a boiling point of lower than 180° C. with the solvent having a boiling point of 180° C. or higher). The high-boiling-point organic solvent is not particularly limited to hydrocarbons, alcohols, ketones, esters, ethers, chlorinated solvents, and so forth, as long as the high-boiling-point organic solvent is capable of dissolving the compound (A). Specific examples of the high-boiling-point organic solvent include 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, glycerin, ethylene glycol monohexyl ether, ethylene glycol mono-2-ethylhexyl ether, ethylene glycol monophenyl ether, ethylene glycol monobenzyl ether, diethylene glycol monoethyl ether, diethylene glycol monoisopropyl ether, diethylene glycol mono-n-butyl ether, diethylene glycol monoisobutyl ether, diethylene glycol monohexyl ether, diethylene glycol monophenyl ether, diethylene glycol monobenzyl ether, diethylene glycol diethyl ether, diethylene glycol dibutyl ether, diethylene glycol butylmethyl ether, triethylene glycol dimethyl ether, triethylene glycol monomethyl ether, triethylene glycol-n-butyl ether, triethylene glycol butylmethyl ether, triethylene glycol diacetate, tetraethylene glycol dimethyl ether, dipropylene glycol monomethyl ether, dipropylene glycol mono-n-propyl ether, dipropylene glycol methyl-n-propyl ether, dipropylene glycol mono-n-butyl ether, tripropylene glycol dimethyl ether, tripropylene glycol monomethyl ether, tripropylene glycol mono-n-propyl ether, tripropylene glycol mono-n-butyl ether, ethylene glycol monoethyl ether acetate, ethylene glycol monobutyl ether acetate, diethylene glycol monomethyl ether acetate, diethylene glycol monoethyl ether acetate, diethylene glycol monobutyl ether acetate, triacetin, propylene glycol diacetate, dipropylene glycol monomethyl ether acetate, dipropylene glycol methyl ether acetate, 1,4-butanediol diacetate, 1,3-butylene glycol diacetate, 1,6-hexanediol diacetate, triethylene glycol diacetate, γ-butyrolactone, methyl benzoate, ethyl benzoate, propyl benzoate, butyl benzoate, dihexyl malonate, diethyl succinate, dipropyl succinate, dibutyl succinate, dihexyl succinate, n-nonyl acetate, dimethyl adipate, diethyl adipate, dibutyl adipate, and the like. These may be used alone or in mixture thereof.

The boiling point of the high-boiling-point solvent may be appropriately selected according to the temperature at which the material for forming an organic film is heated. The boiling point of the high-boiling-point solvent to be added is preferably 180° C. to 300° C., more preferably 200° C. to 300° C. Such a boiling point prevents the evaporation rate at baking (heating) from becoming excessive, which would otherwise occur if the boiling point is too low. Thus, the boiling point of 180° C. or higher can provide sufficient thermal flowability. Meanwhile, with such a boiling point, the boiling point is not too high, so that the high-boiling-point solvent evaporates after baking and does not remain in the film; thus, the boiling point of 300° C. or lower does not adversely affect the film physical properties such as etching resistance.

When the high-boiling-point solvent is used, the formulation amount of the high-boiling-point solvent is preferably 1 to 30 parts by mass based on 100 parts by mass of the solvent having a boiling point of lower than 180° C. The formulation amount in this range prevents a failure in providing sufficient thermal flowability during baking, which would otherwise occur if the formulation amount is too small. In addition, deterioration of the film physical properties such as etching resistance is prevented, which would otherwise occur if the formulation amount is so large that the solvent remains in the film.

With such an organic film composition, the above-described compound for forming an organic film is provided with thermal flowability by adding the high-boiling-point solvent, so that the composition for forming an organic film also has high filling and planarizing properties.

Besides the components (A) and (B), the inventive material for forming an organic film may contain other components as necessary.

[Blend Compound, etc.]

The inventive material for forming an organic film may be further blended with a different compound or polymer. The blend compound or blend polymer mixed with the inventive material for forming an organic film serves to improve the film-formability with spin-coating and the filling property for a stepped substrate. Examples of such a material include novolak resins of phenol, o-cresol, m-cresol, p-cresol, 2,3-dimethylphenol, 2,5-dimethylphenol, 3,4-dimethylphenol, 3,5-dimethylphenol, 2,4-dimethylphenol, 2,6-dimethylphenol, 2,3,5-trimethylphenol, 3,4,5-trimethylphenol, 2-tert-butylphenol, 3-tert-butylphenol, 4-tert-butylphenol, 2-phenylphenol, 3-phenylphenol, 4-phenylphenol, 3,5-diphenylphenol, 2-naphthylphenol, 3-naphthylphenol, 4-naphthylphenol, 4-tritylphenol, resorcinol, 2-methylresorcinol, 4-methylresorcinol, 5-methylresorcinol, catechol, 4-tert-butylcatechol, 2-methoxyphenol, 3-methoxyphenol, 2-propylphenol, 3-propylphenol, 4-propylphenol, 2-isopropylphenol, 3-isopropylphenol, 4-isopropylphenol, 2-methoxy-5-methylphenol, 2-tert-butyl-5-methylphenol, pyrogallol, thymol, isothymol, 4,4'-(9H-fluorene-9-ylidene)bisphenol, 2,2'dimethyl-4,4'-(9H-fluorene-9-ylidene)bisphenol, 2,2'diallyl-4,4'-(9H-fluorene-9-ylidene)bisphenol, 2,2'difluoro-4,4'-(9H-fluorene-9-ylidene)bisphenol, 2,2'diphenyl-4,4'-(9H-fluorene-9-ylidene)bisphenol, 2,2'dimethoxy-4,4'-(9H-fluorene-9-ylidene)bisphenol, 2,3,2',3'-tetrahydro-(1,1')-spirobiindene-6,6'-diol, 3,3,3',3'-tetramethyl-2,3,2',3'-tetrahydro-(1,1')-spirobiindene-6,6'-diol, 3,3,3',3',4,4'-hexamethyl-2,3,2',3'-tetrahydro-(1,1')-spirobiindene-6,6'-diol, 2,3,2',3'-tetrahydro-(1,1')-spirobiindene-5,5'-diol, 5,5'-dimethyl-3,3,3',3'-tetramethyl-2,3,2',3'-tetrahydro-(1,1')-spirobiindene-6,6'-diol, 1-naphthol, 2-naphthol, 2-methyl-1-naphthol, 4-methoxy-1-naphthol, and 7-methoxy-2-naphthol, dihydroxynaphthalenes such as 1,5-dihydroxynaphthalene, 1,7-dihydroxynaphthalene, and 2,6-dihydroxynaphthalene, methyl 3-hydroxynaphthalene-2-carboxylate, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, limonene, etc.; and polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, poly(meth)acrylate, and copolymers thereof. It is also possible to blend a naphthol dicyclopentadiene copolymer disclosed in JP 2004-205685 A, a fluorene bisphenol novolak resin disclosed in JP 2005-128509 A, an acenaphthylene copolymer disclosed in JP 2005-250434 A, fullerene having a phenol group disclosed in JP 2006-227391 A, a bisphenol compound and a novolak resin thereof disclosed in JP 2006-293298 A, a novolak resin of an adamantane phenol compound disclosed in JP 2006-285095 A, a bisnaphthol compound and a novolak resin thereof disclosed in JP 2010-122656 A, a fullerene resin compound disclosed in JP 2008-158002 A, or the like. The blend compound or the blend polymer is blended in an amount of preferably 0 to 1,000 parts by mass, more preferably 0 to 500 parts by mass, based on 100 parts by mass of the inventive organic film material.

[Acid Generator]

In the inventive organic film material, an acid generator can be added so as to further promote the curing reaction. The acid generator includes a material that generates an acid by thermal decomposition, and a material that generates an acid by light irradiation. Any acid generator can be added. Specifically, materials disclosed in paragraphs (0061) to (0085) of JP 2007-199653 A can be added, but the present invention is not limited thereto.

The acid generators can be used alone or in combination of two or more thereof. When the acid generator is added, the added amount is preferably 0.05 to 50 parts, more preferably 0.1 to 10 parts, based on 100 parts of the compound.

[Surfactant]

To the inventive organic film material, a surfactant can be added so as to enhance the coating property in spin-coating. As examples of the surfactant, those disclosed in (0142) to (0147) of JP 2009-269953 A can be used.

[Crosslinking Agent]

Moreover, to the composition for forming an organic film of the present invention, a crosslinking agent can also be added so as to increase the curability and to further suppress intermixing with a resist upper layer film. The crosslinking agent is not particularly limited, and known various types of crosslinking agents can be widely used. Examples thereof include melamine-based crosslinking agents, methylol or methoxymethyl-type crosslinking agents of polynuclear phenols, glycoluril-based crosslinking agents, benzoguanamine-based crosslinking agents, urea-based crosslinking agents, β-hydroxyalkylamide-based crosslinking agents, isocyanurate-based crosslinking agents, aziridine-based crosslinking agents, oxazoline-based crosslinking agents, and epoxy-based crosslinking agents.

Specific examples of the melamine-based crosslinking agents include hexamethoxymethylated melamine, hexabutoxymethylated melamine, alkoxy- and/or hydroxy-substituted derivatives thereof, and partial self-condensates thereof.

Examples of the methoxymethyl type crosslinking agents of polynuclear phenols include tetramethylated and tetramethoxymethylated bisphenols such as bisphenol A and bisphenol F, hexamethoxymethylated trisphenols such as triphenolmethane, triphenolethane, 1,1,1-tris(4-hydroxyphenyl)ethane, tris(4-hydroxyphenyl)-1-ethyl-4-isopropylbenzene, and partial condensates thereof.

Specific examples of the glycoluril-based crosslinking agents include tetramethoxymethylated glycoluril, tetrabutoxymethylated glycoluril, alkoxy- and/or hydroxy-substituted derivatives thereof, and partial self-condensates thereof.

Specific examples of the benzoguanamine-based crosslinking agents include tetramethoxymethylated benzoguanamine, tetrabutoxymethylated benzoguanamine, alkoxy- and/or hydroxy-substituted derivatives thereof, and partial self-condensates thereof.

Specific examples of the urea-based crosslinking agents include dimethoxymethylated dimethoxyethyleneurea, alkoxy- and/or hydroxy-substituted derivatives thereof, and partial self-condensates thereof.

A specific example of the β-hydroxyalkylamide-based crosslinking agents includes N,N,N',N'-tetra(2-hydroxyethyl)adipic acid amide.

Specific examples of the isocyanurate-based crosslinking agents include triglycidyl isocyanurate and triallyl isocyanurate.

Specific examples of the aziridine-based crosslinking agents include 4,4'-bis(ethyleneiminocarbonylamino)diphenylmethane and 2,2-bishydroxymethylbutanol-tris[3-(1-aziridinyl)propionate].

Specific examples of the oxazoline-based crosslinking agents include 2,2'-isopropylidene bis(4-benzyl-2-oxazoline), 2,2'-isopropylidene bis(4-phenyl-2-oxazoline), 2,2'-methylenebis4,5-diphenyl-2-oxazoline, 2,2'-methylenebis-4-phenyl-2-oxazoline, 2,2'-methylenebis-4-tert-butyl-2-oxazoline, 2,2'-bis(2-oxazoline), 1,3-phenylenebis(2-oxazoline), 1,4-phenylenebis(2-oxazoline), and a 2-isopropenyloxazoline copolymer.

Specific examples of the epoxy-based crosslinking agents include diglycidyl ether, ethylene glycol diglycidyl ether, 1,4-butanediol diglycidyl ether, 1,4-cyclohexanedimethanol diglycidyl ether, poly(glycidyl methacrylate), trimethylolethane triglycidyl ether, trimethylolpropane triglycidyl ether, and pentaerythritol tetraglycidyl ether.

[Plasticizer]

Further, to the inventive organic film material, a plasticizer can be added so as to further enhance the high filling and planarizing properties. The plasticizer is not particularly limited, and known various types of plasticizers can be widely used. Examples thereof include low-molecular-weight compounds such as phthalic acid esters, adipic acid esters, phosphoric acid esters, trimellitic acid esters, and citric acid esters; and polymers such as polyethers, polyesters, and polyacetal-based polymers disclosed in JP 2013-253227 A.

[Other Additives]

Particularly, like the plasticizer, as an additive for providing the composition for forming an organic film of the present invention with filling and planarizing properties, it is preferable to use, for example, liquid additives having polyethylene glycol and polypropylene glycol structures, or thermo-decomposable polymers having a weight loss ratio between 30° C. and 250° C. of 40 mass % or more and a weight-average molecular weight of 300 to 200,000. The thermo-decomposable polymers preferably contain a repeating unit having an acetal structure shown by the following general formula (DP1) or (DP1a).

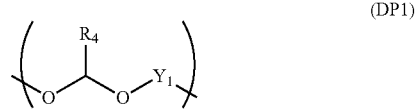

(DP1)

(In the formula, $R_4$ represents a hydrogen atom or a saturated or unsaturated monovalent organic group having 1 to 30 carbon atoms which may be substituted. $Y_1$ represents a saturated or unsaturated divalent organic group having 2 to 30 carbon atoms.)

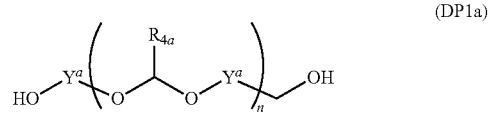

(DP1a)

(In the formula, $R_{4a}$ represents an alkyl group having 1 to 4 carbon atoms. $Y^a$ represents a saturated or unsaturated divalent hydrocarbon group having 4 to 10 carbon atoms which may have an ether bond. "n" represents an average repeating unit number of 3 to 500.)

Note that the inventive material for forming an organic film can be used alone or in combination of two or more thereof. In particular, the material for forming an organic film can be used for a resist underlayer film material or a planarizing material for manufacturing a semiconductor device.

In addition, the inventive material for forming an organic film is extremely useful as a resist underlayer film material in a multilayer resist process such as a 2-layer resist process, a 3-layer resist process using a middle layer film containing a silicon atom, or a 4-layer resist process using an inorganic hard mask middle layer film containing a silicon atom and an organic antireflective coating.

[Substrate for Manufacturing Semiconductor Device]

Additionally, the present invention can provide a substrate for manufacturing a semiconductor device, including an organic film on the substrate, the organic film being formed by curing the above-described material for forming an organic film.

A resist underlayer film obtained by curing the inventive material for forming an organic film has high filling and planarizing properties and adhesion to a substrate, and accordingly, the resist underlayer film does not have fine pores due to insufficient filling, asperity in the resist underlayer film surface due to insufficient planarizing property, or film delamination when forming the inorganic hard mask middle layer film directly on the resist underlayer film. A substrate for manufacturing a semiconductor device planarized by such a resist underlayer film has an increased process margin at patterning, making it possible to manufacture semiconductor devices with high yields.

[Method for Forming Organic Film]

The present invention provides a method for forming an organic film which serves as a resist underlayer film in a multilayer resist film used in lithography or a planarizing film for manufacturing a semiconductor by using the above-described organic film material.

In the inventive method for forming an organic film, a substrate to be processed is coated with the organic film material by a spin-coating method etc. By employing a method like spin-coating method, favorable filling property can be obtained. After the spin-coating, baking (heating) is performed to evaporate the solvent and to promote the crosslinking reaction, thereby preventing the mixing with a resist upper layer film or a resist middle layer film. The baking is preferably performed at 100° C. or higher to 600° C. or lower for 10 to 600 seconds, more preferably at 200° C. or higher to 500° C. or lower for 10 to 300 seconds. In considering the influences of device damage and wafer deformation, the upper limit of the heating temperature in lithographic wafer process is preferably 600° C. or lower, more preferably 500° C. or lower.

Moreover, in the inventive method for forming an organic film, after a substrate to be processed is coated with the inventive organic film material by the spin-coating method or the like as described above, an organic film can be formed by curing the organic film material by baking (heating) in an atmosphere with an oxygen concentration of 0.1% or more to 21% or less.

The organic film material of the present invention is baked in such an oxygen atmosphere, thereby enabling to obtain a fully cured film.

The atmosphere during the heating may be in air, or an inert gas such as $N_2$, Ar, and He may be introduced. In addition, the heating temperature, etc. can be the same as described above.

As the substrate to be processed, a substrate to be processed having a structure or a step with a height of 30 nm or more can be used.

Because of the high filling and planarizing properties, the inventive method for forming an organic film as described above can provide a flat cured film regardless of unevenness of a substrate to be processed. Accordingly, the inventive method is particularly useful in forming a flat cured film on a substrate to be processed having a structure or a step with a height of 30 nm or more.

[Patterning Process]

The present invention provides a patterning process according to a 3-layer resist process using the material for forming an organic film as described above. The patterning process is a method for forming a pattern in a body to be processed, and includes at least the following steps:

forming a resist underlayer film by using the inventive material for forming an organic film on the body to be processed;

forming a resist middle layer film (silicon-atom-containing resist middle layer film) by using a resist middle layer film material containing a silicon atom on the resist underlayer film;

forming a resist upper layer film by using a resist upper layer film material including a photoresist composition on the resist middle layer film so that a multilayer resist film is constructed;

forming a resist pattern (circuit pattern) in the resist upper layer film by exposing a pattern circuit region of the resist upper layer film, then developing with a developer;

transferring the pattern to the resist middle layer film by etching the resist middle layer film while using the resist upper layer film having the formed resist pattern as an etching mask;

transferring the pattern to the resist underlayer film by etching the resist underlayer film while using the obtained resist middle layer film pattern as an etching mask; and further forming the pattern on the substrate to be processed by etching the substrate to be processed while using the resist underlayer film pattern as an etching mask.

The silicon-atom-containing resist middle layer film in the 3-layer resist process exhibits resistance to etching by an oxygen gas or a hydrogen gas. Thus, when the resist underlayer film is etched while using the resist middle layer film as a mask in the 3-layer resist process, the etching is preferably performed using an etching gas mainly containing an oxygen gas or a hydrogen gas.

As the silicon-atom-containing resist middle layer film in the 3-layer resist process, a polysilsesquioxane-based middle layer film is also favorably used. The resist middle layer film having an antireflective effect can suppress the reflection. Particularly, for 193-nm light exposure, a material containing many aromatic groups and having high substrate etching resistance is used as a resist underlayer film, so that the k-value and thus the substrate reflection are increased. However, the reflection can be suppressed by the resist middle layer film, and so the substrate reflection can be reduced to 0.5% or less. As the resist middle layer film having the antireflective effect, a polysilsesquioxane is preferably used, the polysilsesquioxane having anthracene for 248-nm and 157-nm light exposure, or a phenyl group or a light-absorbing group having a silicon-silicon bond for 193-nm light exposure in a pendant structure, and being crosslinked by an acid or heat.

In this case, forming a silicon-containing resist middle layer film by a spin-coating method is simpler and more advantageous regarding cost than a CVD method.

In addition, a 4-layer resist process using an organic antireflective coating is also favorable, and in this case, a pattern can be formed on a body to be processed by performing at least the following steps:

forming a resist underlayer film by using the inventive material for forming an organic film on the body to be processed;

forming a resist middle layer film (silicon-atom-containing resist middle layer film) by using a resist middle layer film material containing a silicon atom on the resist underlayer film;

forming a BARC (organic antireflective coating) on the resist middle layer film;

forming a resist upper layer film by using a resist upper layer film material being a photoresist composition on the BARC so that a multilayer resist film is constructed;

forming a resist pattern (circuit pattern) in the resist upper layer film by exposing a pattern circuit region of the resist upper layer film, then developing with a developer;

transferring the pattern to the resist middle layer film by etching the BARC and the resist middle layer film while using the resist pattern as an etching mask;

transferring the pattern to the resist underlayer film by etching the resist underlayer film while using the resist middle layer film pattern as an etching mask; and further forming the pattern on the body to be processed by etching the body to be processed while using the resist underlayer film pattern as an etching mask.

In addition, an inorganic hard mask middle layer film can be formed as a middle layer film, and in this case, a pattern can be formed on a body to be processed by performing at least the following steps:

forming a resist underlayer film by using the inventive material for forming an organic film on a body to be processed;

forming an inorganic hard mask middle layer film selected from a silicon oxide film, a silicon nitride film, and a silicon oxynitride film on the resist underlayer film;

forming a resist upper layer film by using a resist upper layer film material including a photoresist composition on the inorganic hard mask middle layer film;

forming a resist pattern (circuit pattern) in the resist upper layer film by exposing a pattern circuit region of the resist upper layer film, then developing with a developer;

transferring the pattern to the inorganic hard mask middle layer film by etching the inorganic hard mask middle layer film while using the resist pattern as an etching mask;

transferring the pattern to the resist underlayer film by etching the resist underlayer film while using the inorganic hard mask middle layer film pattern as an etching mask; and further forming the pattern on the body to be processed by etching the body to be processed while using the resist underlayer film pattern as an etching mask.

In the case where an inorganic hard mask middle layer film is formed on the resist underlayer film as described above, a silicon oxide film, a silicon nitride film, and a silicon oxynitride film (SiON film) can be formed by a CVD method, an ALD method, or the like. The method for forming the silicon nitride film is disclosed in, for example, JP 2002-334869 A and WO 2004/066377 A1. The film thickness of the inorganic hard mask middle layer film is preferably 5 to 200 nm, more preferably 10 to 100 nm. As the inorganic hard mask middle layer film, a SiON film is most preferably used, being effective as an antireflective coating. When the SiON film is formed, the substrate temperature reaches 300 to 500° C. Hence, the underlayer film needs to withstand the temperature of 300 to 500° C. Since the materials for forming an organic film used in the present invention have high heat resistance and can withstand high temperatures of 300° C. to 500° C., the combination of the inorganic hard mask middle layer film formed by a CVD method or an ALD method with the resist underlayer film formed by a spin-coating method is possible.

Formation of an inorganic hard mask middle layer film is also suitable for a 4-layer resist process using an organic antireflective coating, and in this case, a pattern can be formed on a body to be processed by performing at least the following steps:

forming a resist underlayer film by using the inventive material for forming an organic film on the body to be processed;

forming an inorganic hard mask middle layer film selected from a silicon oxide film, a silicon nitride film, and a silicon oxynitride film on the resist underlayer film;

forming a BARC (organic antireflective coating) on the inorganic hard mask middle layer film;

forming a resist upper layer film by using a resist upper layer film material being a photoresist composition on the BARC so that a multilayer resist film is constructed;

forming a resist pattern (circuit pattern) in the resist upper layer film by exposing a pattern circuit region of the resist upper layer film, then developing with a developer;

transferring the pattern to the inorganic hard mask middle layer film by etching the BARC and the inorganic hard mask middle layer film while using the resist pattern as an etching mask;

transferring the pattern to the resist underlayer film by etching the resist underlayer film while using the inorganic hard mask middle layer film pattern as an etching mask; and further forming the pattern on the body to be processed by etching the body to be processed while using the resist underlayer film pattern as an etching mask.

The photoresist film may be formed directly on the inorganic hard mask middle layer film as a resist upper layer film as described above, or alternatively, it is also possible to form a BARC (organic antireflective coating) on the inorganic hard mask middle layer film by spin-coating, and then form a photoresist film thereon. In particular, when a SiON film is used as the inorganic hard mask middle layer film, two antireflective coatings including the SiON film and the BARC make it possible to suppress the reflection even in liquid immersion exposure at a high NA exceeding 1.0. Another advantage of the BARC formation is having an effect of reducing trailing of the photoresist pattern immediately above the SiON film.

The resist upper layer film in the 3-layer or 4-layer resist process may be a positive type or a negative type, and any generally-used photoresist composition can be employed. After spin-coating of the photoresist composition, pre-baking is preferably performed at 60 to 180° C. for 10 to 300 seconds. Then, light exposure, PEB (post-exposure bake), and development are performed according to conventional methods to obtain the resist pattern. Note that the thickness of the resist upper layer film is not particularly limited, but is preferably 30 to 500 nm, and 50 to 400 nm is particularly preferable.

A circuit pattern (resist upper layer film pattern) is formed in the resist upper layer film, and in the circuit pattern formation, the circuit pattern is preferably formed by a photolithography with a wavelength of 10 nm or more to 300 nm or less, a direct drawing by electron beam, a nanoimprinting, or a combination thereof.

Note that examples of exposure light include a high-energy beam with a wavelength of 300 nm or less, specifically, deep ultraviolet ray, KrF excimer laser beam (248 nm), ArF excimer laser beam (193 nm), $F_2$ laser beam (157 nm), Kr laser beam (146 nm), Ar laser beam (126 nm), soft X-ray of 3 to 20 nm (EUV), electron beam (EB), ion beam, X-ray, and the like.

Additionally, in forming the circuit pattern, the circuit pattern is preferably developed by alkaline development or development with an organic solvent.

Next, etching is performed while using the obtained resist upper layer film pattern as an etching mask. In the 3-layer resist process, the resist middle layer film and the inorganic hard mask middle layer film are etched using a fluorocarbon-based gas and using the resist upper layer film pattern as the etching mask. Thereby, a resist middle layer film pattern and an inorganic hard mask middle layer film pattern are formed.

Next, the resist underlayer film is etched while using the obtained resist middle layer film pattern and inorganic hard mask middle layer film pattern as etching masks.

Subsequently, the substrate to be processed can be etched according to a conventional method. For example, the substrate to be processed made of $SiO_2$, SiN, or silica-based low-dielectric insulating film is etched mainly with a fluorocarbon-based gas; and p-Si, Al, or W is etched mainly with a chlorine- or bromine-based gas. When the substrate is processed by etching with a fluorocarbon-based gas, the silicon-atom-containing middle layer film pattern in the 3-layer resist process is removed when the substrate is processed. When the substrate is etched with a chlorine- or bromine-based gas, the silicon-containing middle layer film pattern needs to be removed by additional dry etching with a fluorocarbon-based gas after the substrate processing.

Furthermore, the body to be processed can be a semiconductor device substrate or the semiconductor device substrate coated with any of a metal film, a metal carbide film, a metal oxide film, a metal nitride film, a metal oxycarbide film, or a metal oxynitride film.

Furthermore, the body to be processed can be metallic silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

A resist underlayer film obtained from the inventive material for forming an organic film has a characteristic of being excellent in etching resistance when etching these bodies to be processed.

Note that the body to be processed is not particularly limited, and examples of the semiconductor device substrate include: substrates made of Si, α-Si, p-Si, $SiO_2$, SiN, SiON, W, TiN, Al, or the like; the body to be processed coated with a layer to be processed; etc. Examples of the layer to be processed include: various Low-k films made of Si, $SiO_2$, SiON, SiN, p-Si, α-Si, W, W—Si, Al, Cu, Al—Si, or the like; and stopper films thereof. Generally, the layer can be formed to have a thickness of 50 to 10,000 nm, in particular, 100 to 5,000 nm. Note that when the layer to be processed is formed, the body to be processed and the layer to be processed are formed from different materials.

Hereinbelow, an example of the 3-layer resist process will be specifically described with reference to FIG. 1.

As shown in FIG. 1 (A), in the 3-layer resist process, a resist underlayer film 3 is formed by using the inventive material for forming an organic film on a layer 2 to be processed that has been stacked on a substrate 1 to be processed. Then, a silicon-atom-containing resist middle layer film 4 is formed, and a resist upper layer film 5 is formed thereon.

Next, as shown in FIG. 1 (B), a predetermined portion (exposed portion 6) of the resist upper layer film 5 is exposed to light, followed by PEB and development to form a resist upper layer film pattern 5a (FIG. 1 (C)). While using the obtained resist upper layer film pattern 5a as an etching mask, the silicon-atom-containing resist middle layer film 4 is etched with a CF-based gas. Thereby, a silicon-atom-containing resist middle layer film pattern 4a is formed (FIG. 1 (D)). After the resist upper layer film pattern 5a is removed, the resist underlayer film 3 is etched with oxygen plasma while using the obtained silicon-atom-containing resist middle layer film pattern 4a as an etching mask. Thereby, a resist underlayer film pattern 3a is formed (FIG. 1 (E)). Further, after the silicon-atom-containing resist middle layer film pattern 4a is removed, the layer 2 to be processed is etched while using the resist underlayer film pattern 3a as an etching mask. Thus, a pattern 2a is formed (FIG. 1 (F)).

When an inorganic hard mask middle layer film is used, the silicon-atom-containing resist middle layer film 4 is the inorganic hard mask middle layer film, and when a BARC is formed, the BARC is disposed between the silicon-atom-containing resist middle layer film 4 and the resist upper layer film 5. The etching of the BARC may be performed continuously before the etching of the silicon-atom-containing resist middle layer film 4. Alternatively, after the BARC is etched alone, the etching apparatus is changed, for example, and then the etching of the silicon-atom-containing resist middle layer film 4 may be performed.

As described above, the inventive patterning processes make it possible to precisely form a fine pattern in a substrate to be processed in the multilayer resist processes.

EXAMPLE

Hereinafter, the present invention will be more specifically described with reference to Synthesis Examples, Comparative Synthesis Examples, Examples, and Comparative Examples. However, the present invention is not limited thereto. Note that, specifically, the molecular weight was measured by the following method.

[Molecular Weight Measurement]

Weight-average molecular weight (Mw) and number-average molecular weight (Mn) were measured by GPC (gel permeation chromatography) using tetrahydrofuran as an eluent in terms of polystyrene, and dispersity (Mw/Mn) was calculated therefrom.

Synthesis Examples: Synthesis of Compounds Used in Organic Film Material

Polymers (A1) to (A28) for organic film materials were synthesized using epoxy compounds (Compounds B: (B1) to (B14)) and carboxylic acid compounds (Compounds C: (C1) to (C8)) shown below.

Compounds B:

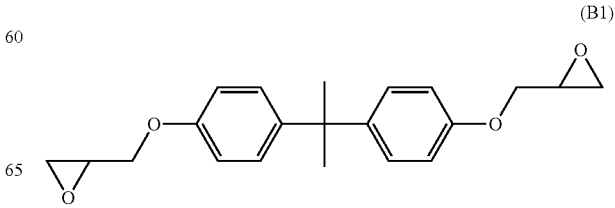

(B1)

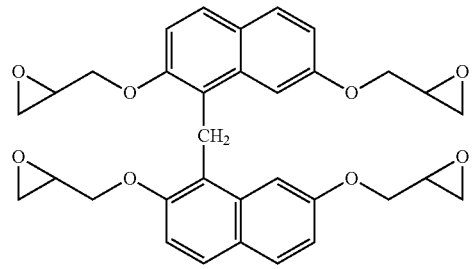
(B2)
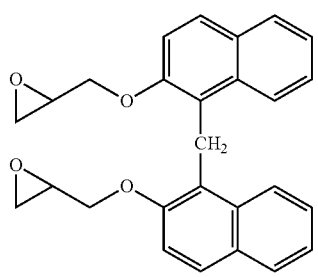
(B3)
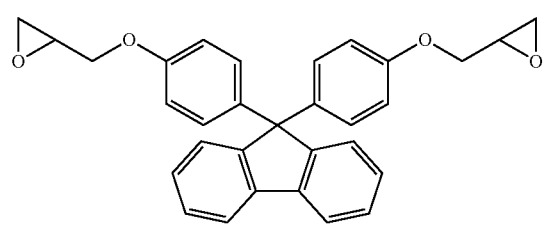
(B4)
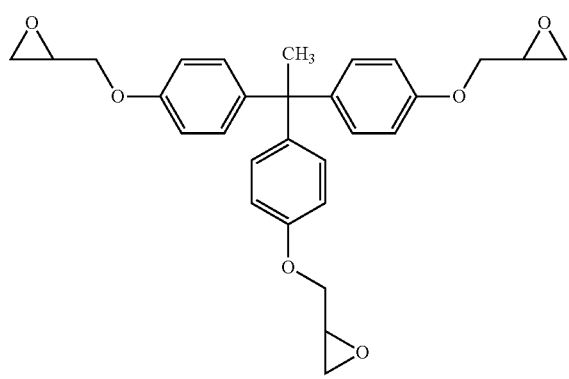
(B5)
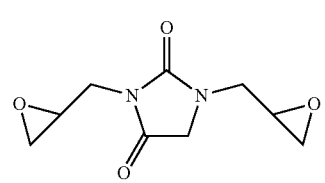
(B6)
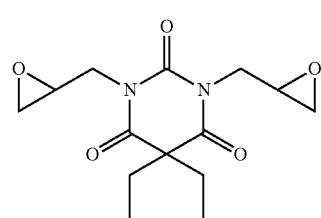
(B7)
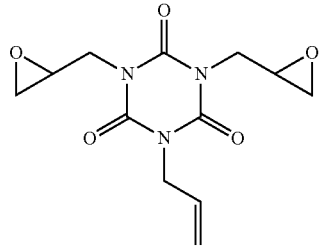
(B8)
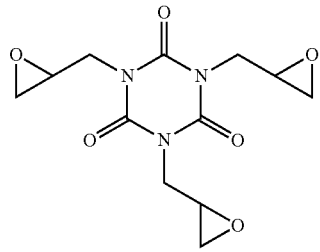
(B9)
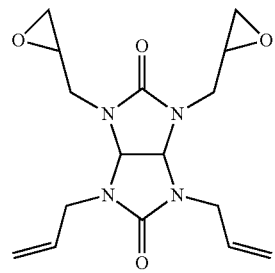
(B10)
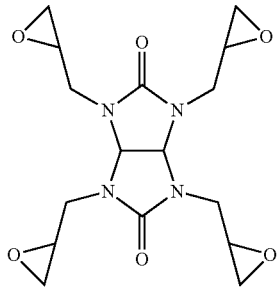
(B11)
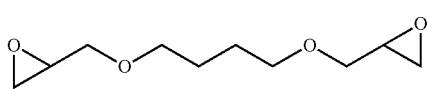
(B12)
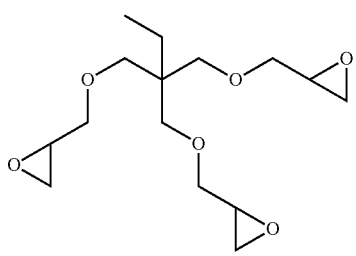
(B13)

(B14)

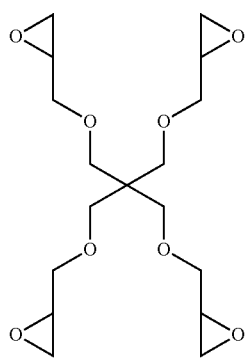

Except for the following, purchased reagents were used.
(B1) EXA-850CRP (manufactured by DIC Corporation) epoxy equivalent: 172
(B2) HP-4700 (manufactured by DIC Corporation) epoxy equivalent: 165
(B3) HP-4770 (manufactured by DIC Corporation) epoxy equivalent: 205
(B5) 1032H60 (manufactured by Mitsubishi Chemical Corporation) epoxy equivalent: 167
(B10) DAG-G (manufactured by Shikoku Chemical Corporation) epoxy equivalent: 168
(B11) TG-G (manufactured by Shikoku Chemical Corporation) epoxy equivalent: 92
(B13) Epolite MF (manufactured by Kyoei Kagaku Kogyo Co., Ltd) epoxy equivalent: 140
(B14) PETG (manufactured by Showa Denko K. K.) epoxy equivalent: 90

Compounds C:

(C1)

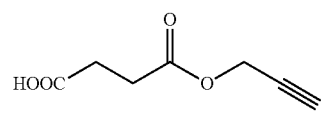

(C2)

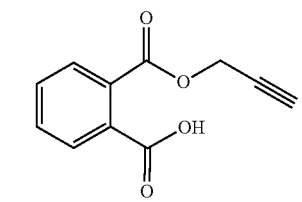

(C3)

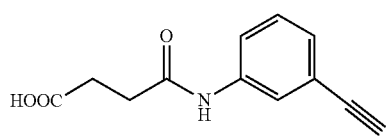

(C4)

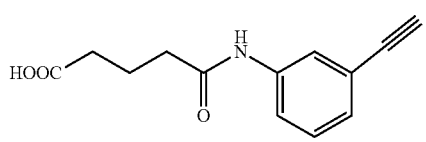

(C5)

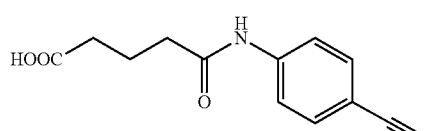

(C6)

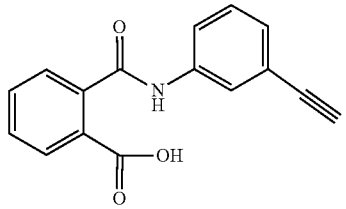

(C7)

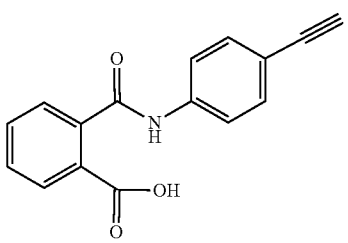

(C8)

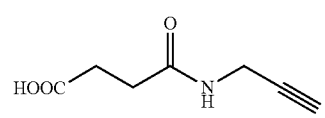

Synthesis of Carboxylic Acid Compound (C1)

To a mixture of 10.0 g of succinic anhydride and 50 g of N,N-dimethylformamide, 6.16 g of propargyl alcohol was slowly added dropwise. The solution was stirred under a nitrogen atmosphere at room temperature for 30 minutes, then the inner temperature was raised to 40° C., and the solution was stirred for 24 hours. After cooling by allowing to stand, 50 mL of a 20% aqueous hydrochloric acid was added, and the reaction was stopped. 100 g of ethyl acetate was added, the resultant was washed three times with 100 g pure water, and the organic layer was evaporated under reduced pressure to dryness. To the residue, 100 g of toluene was added to form a homogeneous solution, then a crystal was precipitated with 200 g of hexane. The precipitated crystal was separated by filtration, washed twice with 100 g of hexane, and collected. The collected crystal was vacuum dried at 70° C. Thus, carboxylic acid compound (C1) was obtained at a yield of 32%.

Synthesis of Carboxylic Acid Compound (C2)

Carboxylic acid compound (C2) was obtained under the same reaction conditions as carboxylic acid compound (C1) except for the used carboxylic acid anhydride.

Synthesis of Carboxylic Acid Compound (C3)

To a mixture of 10.0 g of succinic anhydride and 40 g of N,N-dimethylformamide, a solution of 12.06 g of 3-ethynylaniline dissolved in 10 g of N,N-dimethylformamide was slowly added dropwise. The resultant was stirred under a nitrogen atmosphere at room temperature for 24 hours. After cooling by allowing to stand, 100 g of ethyl acetate was added, the resultant was washed three times with 100 g of pure water, and the organic layer was evaporated under reduced pressure to dryness. To the residue, 100 g of toluene was added to form a homogeneous solution, then a crystal was precipitated in an ice bath. The precipitated crystal was separated by filtration, washed twice with 100 g of toluene, and collected. The collected crystal was vacuum dried at 70° C. Thus, carboxylic acid compound (C3) was obtained at a yield of 47%.

Synthesis of Carboxylic Acid Compounds (C4) to (C8)

Carboxylic acid compounds (C4) to (C8) were obtained under the same reaction conditions as carboxylic acid compound (C3) except for the used carboxylic acid anhydrides and amine compounds.

[Synthesis Example 1] Synthesis of Compound (A1)

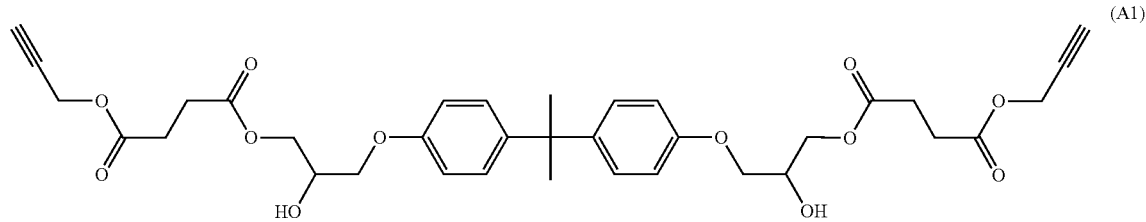 [SMILES: C#CCOC(=O)CCC(=O)OCC(O)COc1ccc(C(C)(C)c2ccc(OCC(O)COC(=O)CCC(=O)OCC#C)cc2)cc1]

A homogeneous solution of 10.0 g of an epoxy compound (B1), 9.08 g of a carboxylic acid compound (C1), and 100 g of 2-methoxy-1-propanol was formed under a nitrogen atmosphere at an inner temperature of 100° C. Then, 0.69 g of benzyltriethylammonium chloride was added, and was stirred at an inner temperature of 120° C. for 12 hours. After cooling to room temperature, 200 ml of methyl isobutyl ketone was added, and the resultant was washed twice with 100 g of a 2% NaHCO$_3$ aqueous solution and 100 g of a 3% nitric acid aqueous solution, and five times with 100 g of ultrapure water. The organic layer was evaporated under reduced pressure to dryness to obtain compound (A1). When the weight-average molecular weight (Mw) and dispersity (Mw/Mn) were measured by GPC, the results were: Mw=1030; Mw/Mn=1.04.

[Synthesis Examples 2 to 28] Synthesis of Compounds (A2) to (A28)

Except that the epoxy compounds and the carboxylic acid compounds shown in Table 1 to Table 4 were used, the compounds (A2) to (A28) shown in Table 1 to Table 4 were obtained as products under the same reaction conditions as Synthesis Example 1. The Mw (weight-average molecular weight) and the dispersity (Mw/Mn) of these compounds were determined and shown in Table 5.

TABLE 1
| Synthesis Example | Epoxy compound | Carboxylic acid compound | Product |
|---|---|---|---|
| A1 | B1 10.0 g | C1 9.1 g | 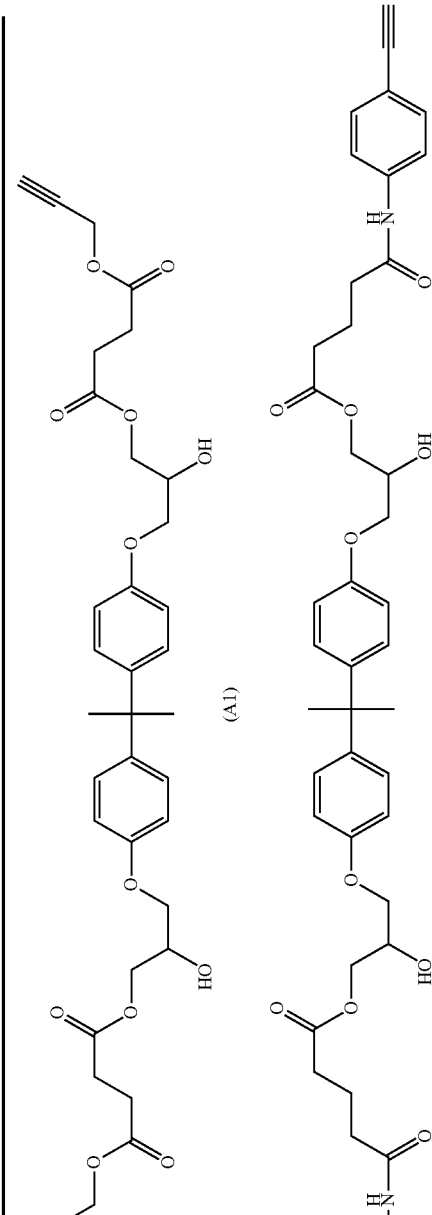 (A1) |
| A2 | B1 10.0 g | C5 13.4 g | 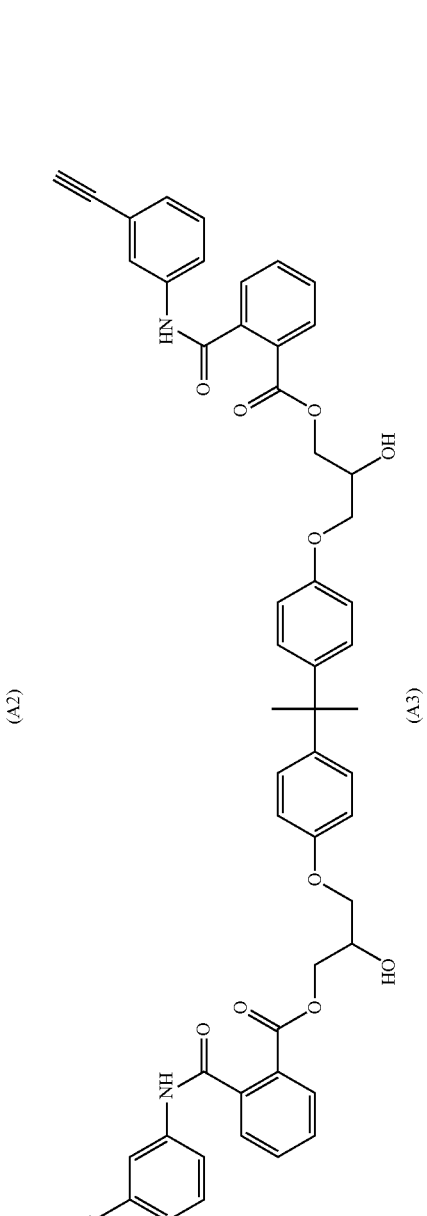 (A2) |
| A3 | B1 10.0 g | C6 15.4 g | 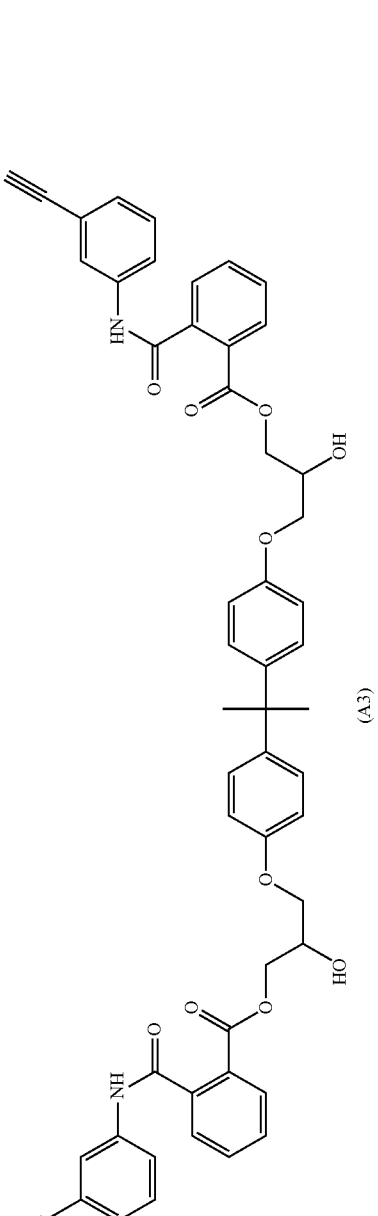 (A3) |

TABLE 1-continued
| Synthesis Example | Epoxy compound | Carboxylic acid compound | Product |
|---|---|---|---|
| A4 | B1 10.0 g | C7 15.4 g | 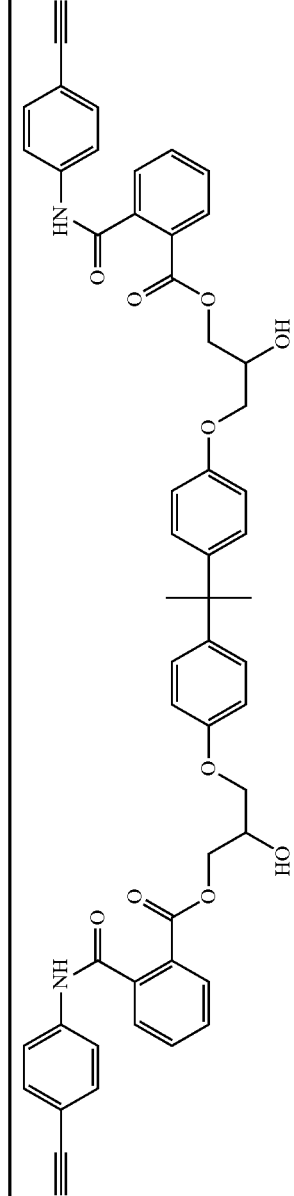 (A4) |
| A5 | B2 10.0 g | C1 9.5 g | 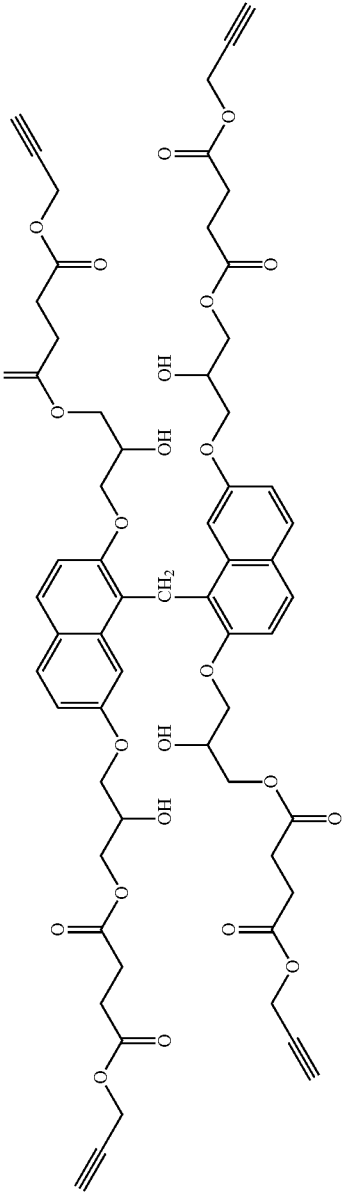 (A5) |

TABLE 1-continued
| Synthesis Example | Epoxy compound | Carboxylic acid compound | Product |
|---|---|---|---|
| A6 | B2 10.0 g | C3 13.2 g | 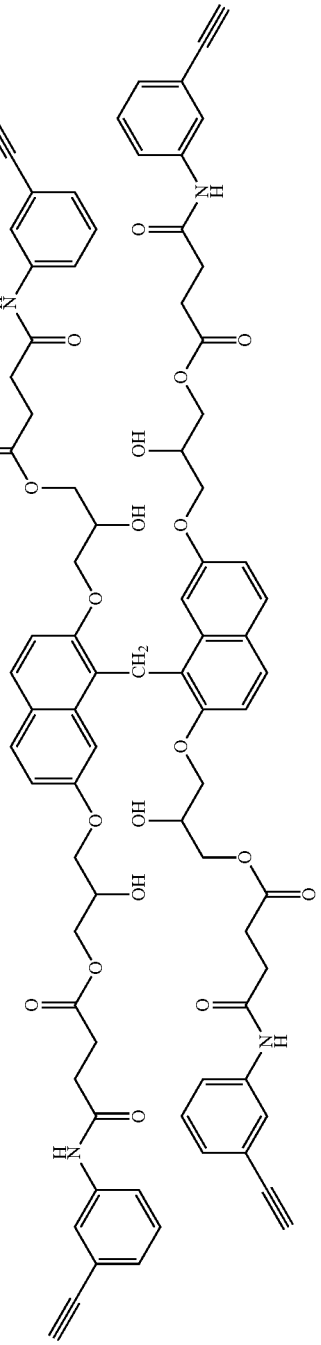 (A6) |
| A7 | B2 10.0 g | C5 14.0 g | 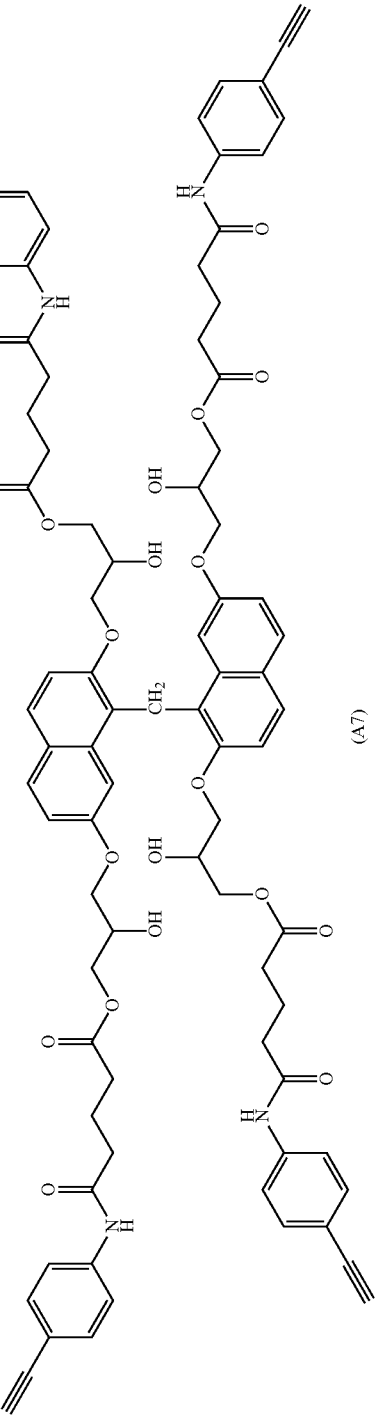 (A7) |

TABLE 1-continued

| Synthesis Example | Epoxy compound | Carboxylic acid compound | Product |
|---|---|---|---|
| A8 | B2 10.0 g | C6 16.1 g | (A8) |

TABLE 2
| Synthesis Example | Epoxy compound | Carboxylic acid compound | Product |
|---|---|---|---|
| A9 | B2 10.0 g | C7 16.1 g | 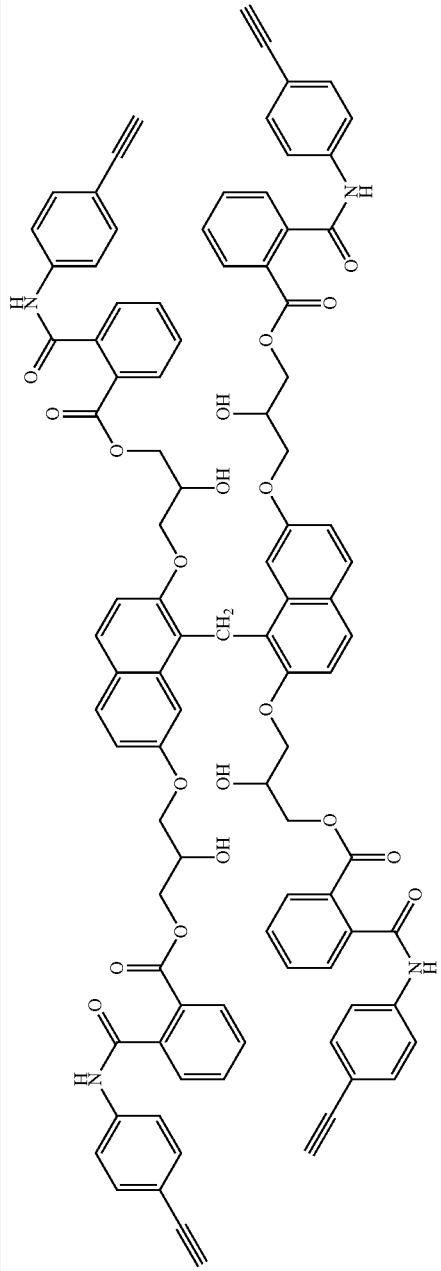 (A9) |
| A10 | B3 10.0 g | C2 10.0 g | 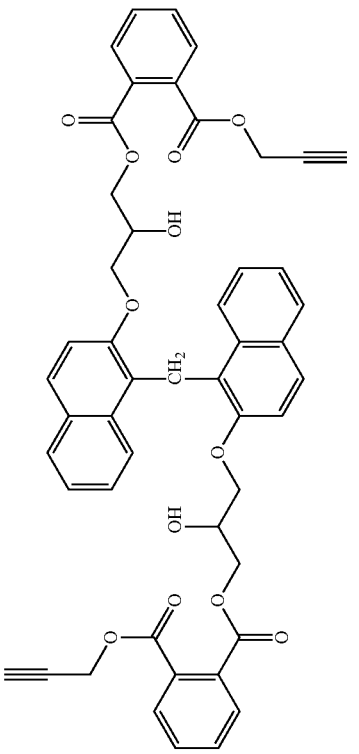 (A10) |

TABLE 2-continued

| Synthesis Example | Epoxy compound | Carboxylic acid compound | Product |
|---|---|---|---|
| A11 | B3 10.0 g | C6 12.9 g | (A11) |
| A12 | B4 10.0 g | C4 9.9 g | (A12) |
| A13 | B4 10.0 g | C5 9.9 g | (A13) |

TABLE 2-continued

| Synthesis Example | Epoxy compound | Carboxylic acid compound | Product |
|---|---|---|---|
| A14 | B5 10.0 g | C7 15.9 g | (structure shown) |
| A15 | B6 5.0 g | C7 12.5 g | (A14) |
| A16 | B7 10.0 g | C7 17.9 g | (A15) (A15) |

TABLE 3
| Synthesis Example | Epoxy compound | Carboxylic acid compound | Product |
|---|---|---|---|
| A17 | B8 10.0 g | C2 14.5 g | 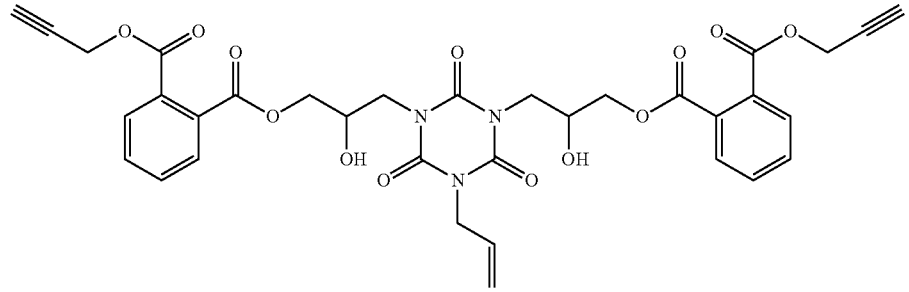 (A17) |
| A18 | B8 10.0 g | C5 16.4 g | 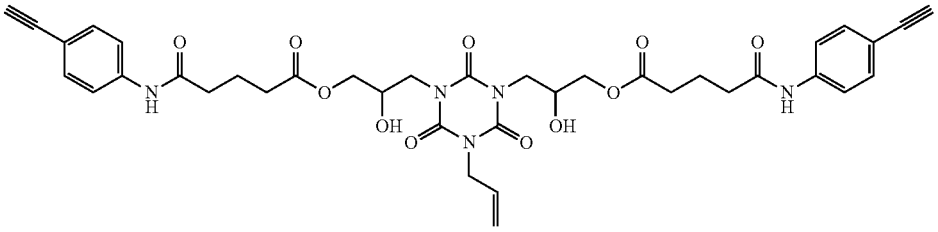 (A18) |
| A19 | B8 10.0 g | C6 18.9 g | 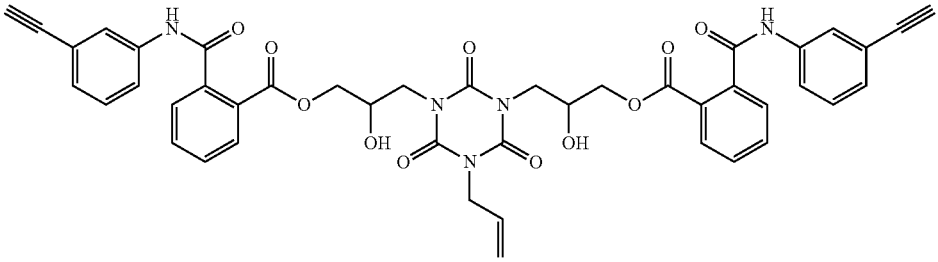 (A19) |
| A20 | B8 10.0 g | C8 11.0 g | 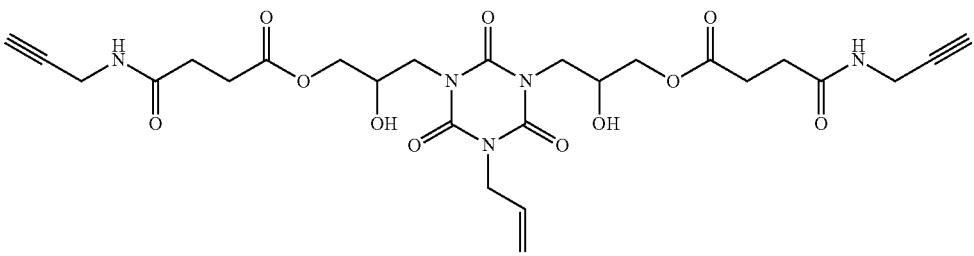 (A20) |

TABLE 3-continued
| Synthesis Example | Epoxy compound | Carboxylic acid compound | Product |
|---|---|---|---|
| A21 | B9 10.0 g | C2 20.6 g | 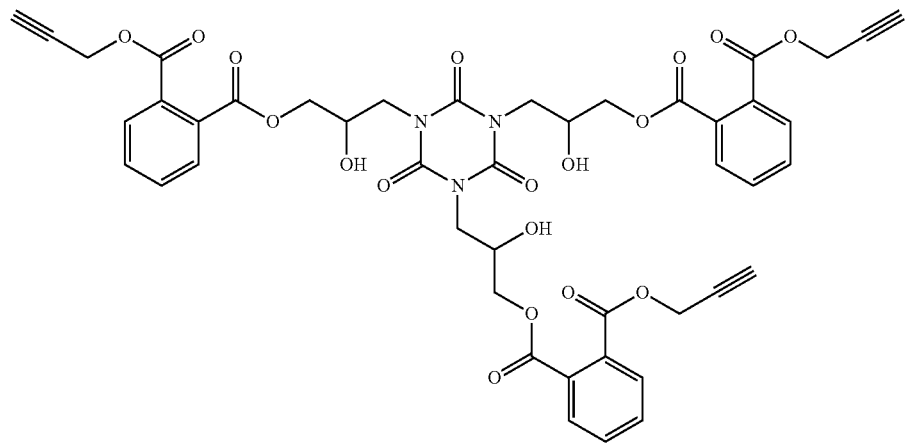 (A21) |
| A22 | B9 10.0 g | C5 23.3 g | 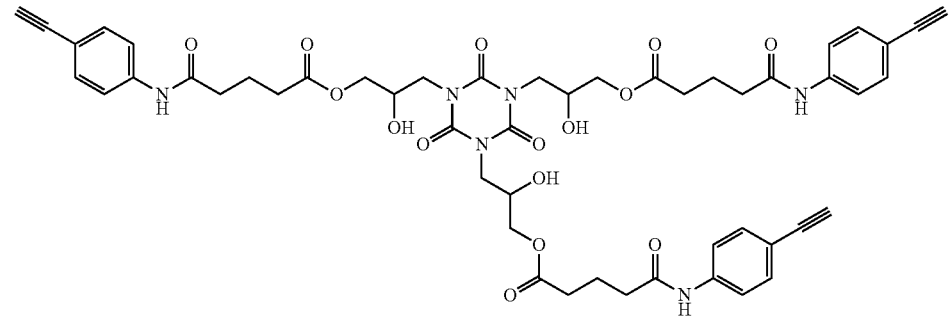 (A22) |
| A23 | B9 10.0 g | C6 26.8 g | 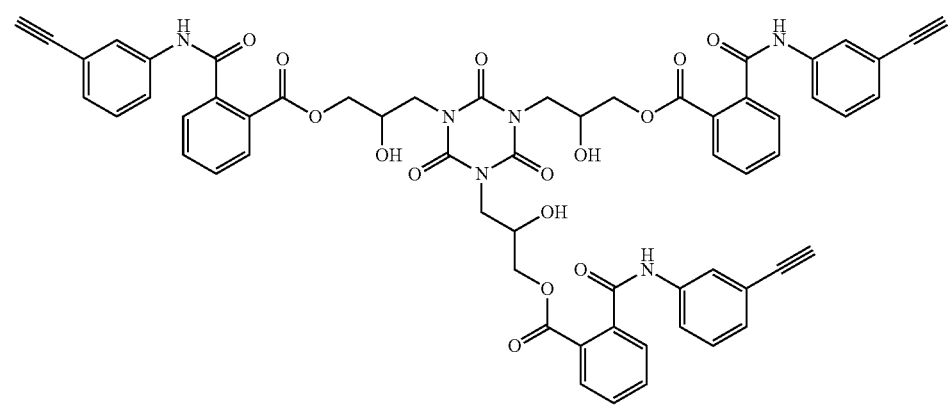 (A23) |

TABLE 4

| Synthesis Example | Epoxy compound | Carboxylic acid compound | Product |
|---|---|---|---|
| A24 | B10 10.0 g | C7 15.8 g | (A24) |
| A25 | B11 5.0 g | C7 14.4 g | (A25) |
| A26 | B12 5.0 g | C7 13.1 g | (A26) |

TABLE 4-continued

| Synthesis Example | Epoxy compound | Carboxylic acid compound | Product |
|---|---|---|---|
| A27 | B13 10.0 g | C7 18.9 g | 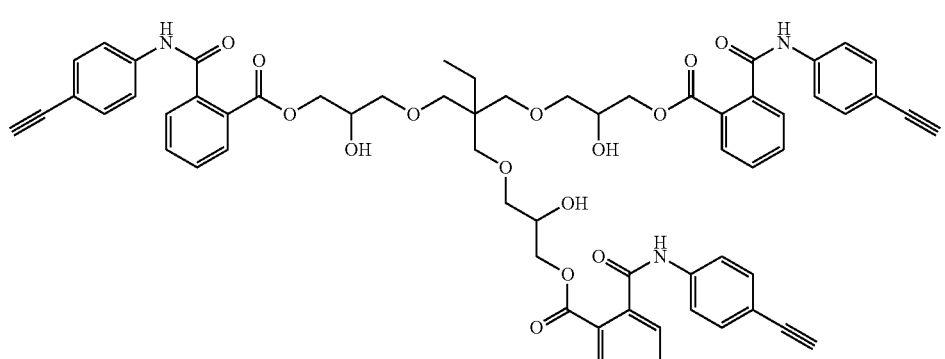 (A27) |
| A28 | B14 5.0 g | C7 14.7 g | 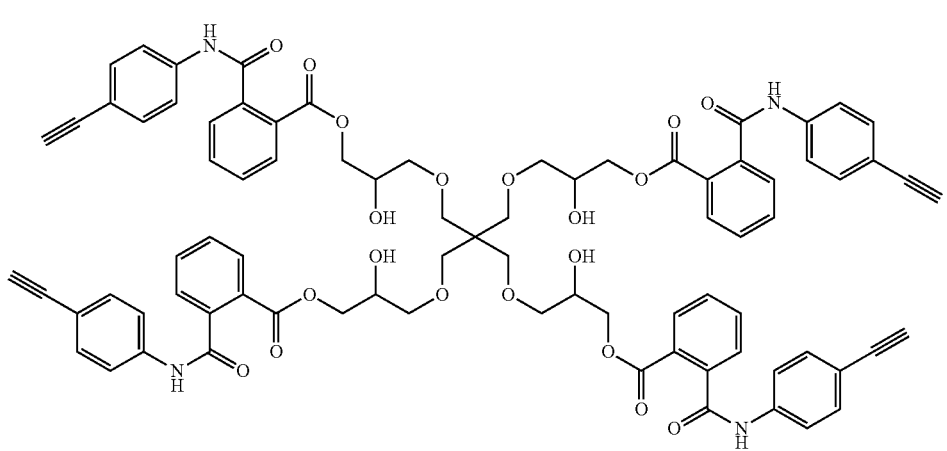 (A28) |

TABLE 5

| Synthesis Example | Compound | Mw (GPC) | Mw/Mn |
|---|---|---|---|
| 1 | (A1) | 1030 | 1.04 |
| 2 | (A2) | 1010 | 1.05 |
| 3 | (A3) | 1050 | 1.07 |
| 4 | (A4) | 1100 | 1.08 |
| 5 | (A5) | 1830 | 1.33 |
| 6 | (A6) | 1850 | 1.33 |
| 7 | (A7) | 1900 | 1.35 |
| 8 | (A8) | 2220 | 1.40 |
| 9 | (A9) | 2170 | 1.38 |
| 10 | (A10) | 1250 | 1.25 |
| 11 | (A11) | 1310 | 1.27 |
| 12 | (A12) | 1270 | 1.04 |
| 13 | (A13) | 1240 | 1.04 |
| 14 | (A14) | 1530 | 1.34 |
| 15 | (A15) | 830 | 1.03 |
| 16 | (A16) | 1180 | 1.07 |
| 17 | (A17) | 1020 | 1.03 |
| 18 | (A18) | 1080 | 1.02 |
| 19 | (A19) | 1100 | 1.04 |
| 20 | (A20) | 980 | 1.02 |
| 21 | (A21) | 1170 | 1.05 |
| 22 | (A22) | 1240 | 1.08 |
| 23 | (A23) | 1180 | 1.05 |
| 24 | (A24) | 1070 | 1.03 |
| 25 | (A25) | 1350 | 1.10 |
| 26 | (A26) | 890 | 1.03 |
| 27 | (A27) | 1200 | 1.05 |
| 28 | (A28) | 1530 | 1.09 |

[Comparative Synthesis Example 1] Synthesis of Compound (R1)

A homogeneous solution of 20.0 g of an epoxy compound (B2), 17.7 g of 4-ethynylbenzoic acid, and 200 g of 2-methoxy-1-propanol was formed under a nitrogen atmosphere at an inner temperature of 100° C. Then, 1.00 g of benzyltriethylammonium chloride was added, and was stirred at an inner temperature of 120° C. for 12 hours. After cooling to room temperature, 300 ml of methyl isobutyl ketone was added, and the resultant was washed twice with 100 g of a 2% NaHCO$_3$ aqueous solution and 100 g of a 3% nitric acid aqueous solution, and five times with 100 g ultrapure water. The organic layer was evaporated under reduced pressure to dryness to obtain compound (R1). When the weight-average molecular weight (Mw) and dispersity (Mw/Mn) were measured by GPC, the results were: Mw=1740; Mw/Mn=1.33.

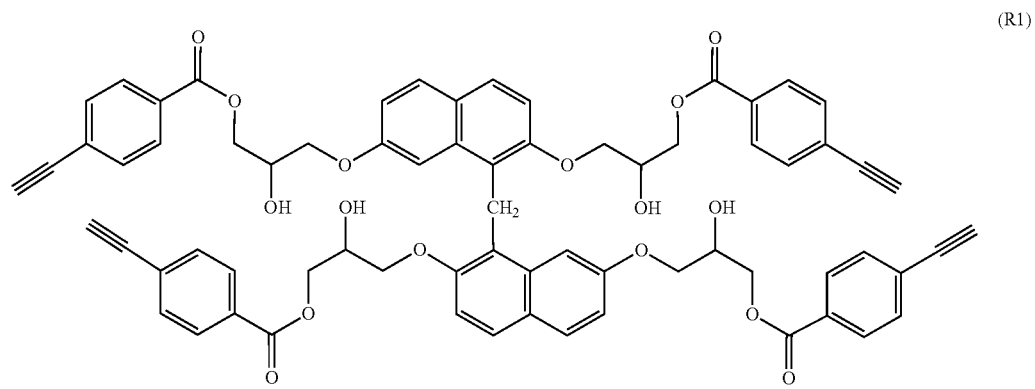 [SMILES: C#Cc1ccc(C(=O)OCC(O)COc2ccc3ccc(OCC(O)COC(=O)c4ccc(C#C)cc4)c(Cc4c(OCC(O)COC(=O)c5ccc(C#C)cc5)ccc5ccc(OCC(O)COC(=O)c6ccc(C#C)cc6)cc45)c3c2)cc1]

(R1)

[Comparative Synthesis Example 2] Synthesis of Compound (R2)

A homogeneous solution of 20.0 g of an epoxy compound (B2), 23.3 g of a 4-butoxybenzoic acid, and 200 g of 2-methoxy-1-propanol was formed under a nitrogen atmosphere at an inner temperature of 100° C. Then, 1.00 g of benzyltriethylammonium chloride was added, and was stirred at an inner temperature of 120° C. for 12 hours. After cooling to room temperature, 300 ml of methyl isobutyl ketone was added, and the resultant was washed twice with 100 g of a 2% NaHCO$_3$ aqueous solution and 100 g of a 3% nitric acid aqueous solution, and five times with 100 g of ultrapure water. The organic layer was evaporated under reduced pressure to dryness to obtain compound (R2). When the weight-average molecular weight (Mw) and dispersity (Mw/Mn) were measured by GPC, the results were: Mw=1930; Mw/Mn=1.32.

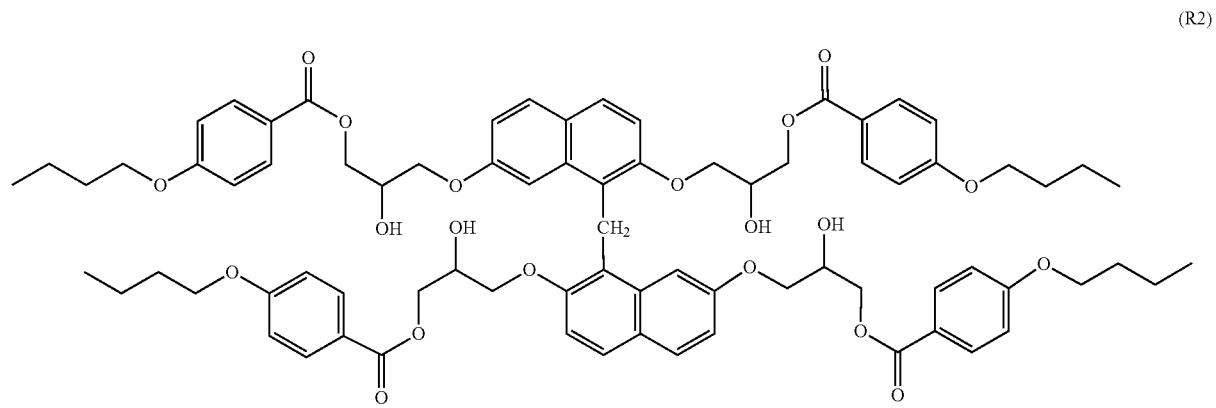 [SMILES: CCCCOc1ccc(C(=O)OCC(O)COc2ccc3ccc(OCC(O)COC(=O)c4ccc(OCCCC)cc4)c(Cc4c(OCC(O)COC(=O)c5ccc(OCCCC)cc5)ccc5ccc(OCC(O)COC(=O)c6ccc(OCCCC)cc6)cc45)c3c2)cc1]

(R2)

[Comparative Synthesis Example 3] Synthesis of Compound (R3)

A homogeneous solution of 20.0 g of an epoxy compound (B2), 16.7 g of a 4-hydroxybenzoic acid, and 200 g 2-methoxy-1-propanol was formed under a nitrogen atmosphere at an inner temperature of 100° C. Then, 1.00 g of benzyltriethylammonium chloride was added, and was stirred at an inner temperature of 120° C. for 12 hours. After cooling to room temperature, 300 ml of methyl isobutyl ketone was added, and the resultant was washed twice with 100 g of a 2% NaHCO$_3$ aqueous solution and 100 g of a 3% nitric acid aqueous solution, and five times with 100 g of ultrapure water. The organic layer was evaporated under reduced pressure to dryness to obtain compound (R3). When the weight-average molecular weight (Mw) and dispersity (Mw/Mn) were measured by GPC, the results were: Mw=1610; Mw/Mn=1.35.

weight (Mw) and dispersity (Mw/Mn) were measured by GPC, the results were: Mw=1,150; Mw/Mn=1.03.

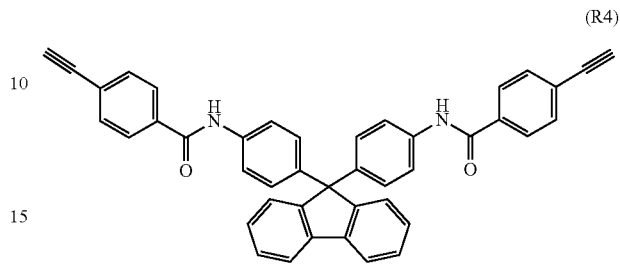

(R4)

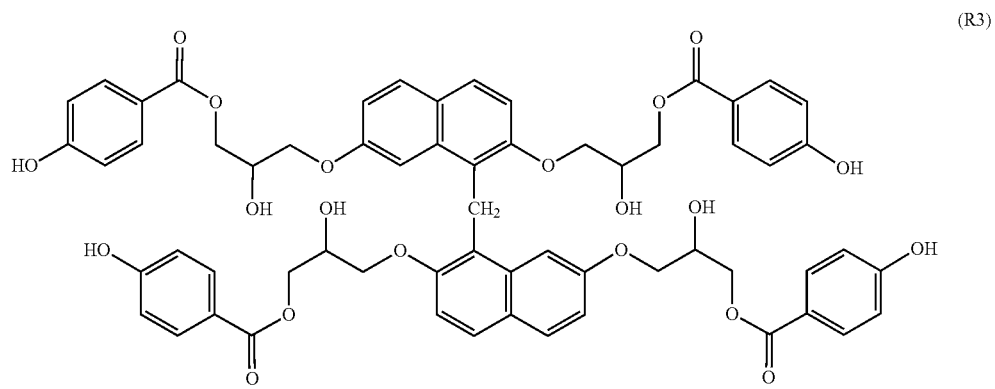 [SMILES: O=C(OCC(O)COc1ccc2ccc(OCC(O)COC(=O)c3ccc(O)cc3)c(Cc3c(OCC(O)COC(=O)c4ccc(O)cc4)ccc4ccc(OCC(O)COC(=O)c5ccc(O)cc5)cc34)c2c1)c1ccc(O)cc1]

(R3)

[Comparative Synthesis Example 4] Synthesis of Compound (R4)

17.4 g of 9,9-bis-(4-aminophenyl)fluorene, 16.5 g of 4-ethylbenzoyl chloride, 5.1 g of triethyl amine, and 150 g of N,N-dimethylacetamide were stirred under a nitrogen atmosphere at a liquid temperature of 0° C. for 1 hour. Then the temperature was raised to room temperature, and the resultant was stirred for 3 hours. After completion of the reaction, 500 g of methyl isobutyl ketone was added, the organic layer was washed five times with 200 g of pure water. Then, the organic layer was evaporated under reduced pressure to dryness. To the residue, 300 mL of THF was added, and the polymer was reprecipitated with 1,000 mL of hexane. The precipitated polymer was separated by filtration, and dried under reduced pressure. Thus, compound (R4) was obtained. When the weight-average molecular

[Comparative Synthesis Example 5] Synthesis of Compound (R5)

A homogeneous solution of 10.0 g of an epoxy compound (B9), 9.9 g of succinic anhydride, and 50 g of 2-methoxy-1-propanol was formed under a nitrogen atmosphere at an inner temperature of 100° C. Then, 0.50 g of benzyltriethylammonium chloride was added, and was stirred at an inner temperature of 120° C. for 12 hours. After cooling to room temperature, 200 ml of methyl isobutyl ketone was added, and the resultant was washed twice with 50 g of a 2% NaHCO$_3$ aqueous solution and 50 g of a 3% nitric acid aqueous solution, and five times with 50 g of ultrapure water. The organic layer was evaporated under reduced pressure to dryness to obtain compound (R5). When the weight-average molecular weight (Mw) and dispersity (Mw/Mn) were measured by GPC, the results were: Mw=1320; Mw/Mn=1.17.

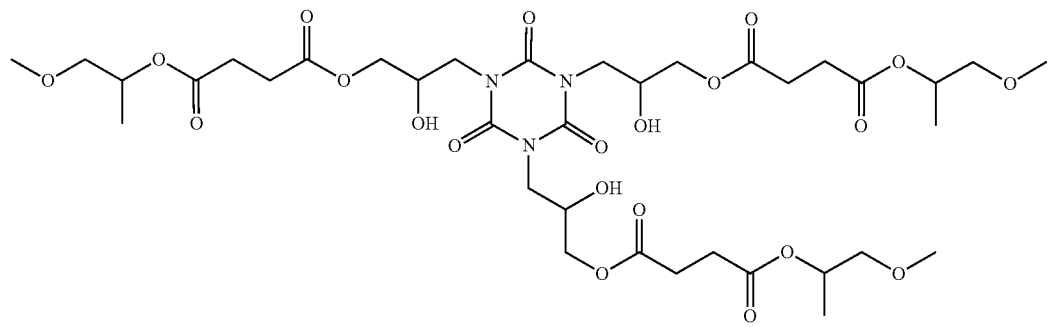

(R5)

None of the compounds (R1) to (R5) contains a group shown by the general formulae (3) of the present invention.

Preparation of (UDL-1 to -30, Comparative UDL-1 to -5)

The following were used: the compounds (A1) to (A28) and comparative compounds (R1) to (R5); (S1) 1,6-diacetoxyhexane having a boiling point of 260° C. and (S2) tripropylene glycol monomethyl ether having a boiling point of 242° C. as high-boiling-point solvents; XL1 as a crosslinking agent; and AG1 as a thermal acid generator. Using propylene glycol monomethyl ether acetate (PGMEA) containing 0.1 mass % of PF636 (manufactured by OMNOVA), being a surfactant, the compounds were dissolved in proportions shown in Table 6. The solution was then filtered through a 0.1-μm filter made of a fluorinated resin to prepare compositions (UDL-1 to -30, comparative UDL-1 to -5) for forming an organic film.

Incidentally, PGME and CyHO are solvents.

The structural formulae of the crosslinking agent (XL1) and the acid generator (AG1) used in Comparative Examples UDL are shown below.

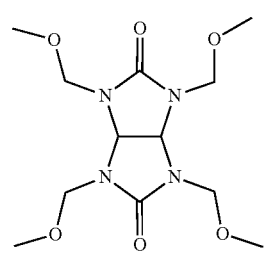

XL1

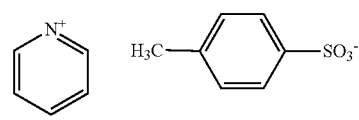

AG1

TABLE 6

| Organic Film Material | Compound (parts by mass) | Crosslinking agent (parts by mass) | Acid generator (parts by mass) | High-boiling-point solvent (parts by mass) | PGMEA (parts by mass) | PGME (parts by mass) | CyHO (parts by mass) |
|---|---|---|---|---|---|---|---|
| UDL-1  | A1 (10)  | — | — | — | 90 | — | — |
| UDL-2  | A2 (10)  | — | — | — | 90 | — | — |
| UDL-3  | A3 (10)  | — | — | — | 90 | — | — |
| UDL-4  | A4 (10)  | — | — | — | 90 | — | — |
| UDL-5  | A5 (10)  | — | — | — | 90 | — | — |
| UDL-6  | A6 (10)  | — | — | — | 90 | — | — |
| UDL-7  | A7 (10)  | — | — | — | 90 | — | — |
| UDL-8  | A8 (10)  | — | — | — | 90 | — | — |
| UDL-9  | A9 (10)  | — | — | — | 90 | — | — |
| UDL-10 | A10 (10) | — | — | — | 90 | — | — |
| UDL-11 | A11 (10) | — | — | — | 90 | — | — |
| UDL-12 | A12 (10) | — | — | — | 90 | — | — |
| UDL-13 | A13 (10) | — | — | — | 90 | — | — |
| UDL-14 | A14 (10) | — | — | — | 90 | — | — |
| UDL-15 | A15 (10) | — | — | — | 90 | — | — |
| UDL-16 | A16 (10) | — | — | — | 90 | — | — |
| UDL-17 | A17 (10) | — | — | — | 90 | — | — |
| UDL-18 | A18 (10) | — | — | — | 90 | — | — |
| UDL-19 | A19 (10) | — | — | — | 90 | — | — |
| UDL-20 | A20 (10) | — | — | — | 90 | — | — |
| UDL-21 | A21 (10) | — | — | — | 90 | — | — |
| UDL-22 | A22 (10) | — | — | — | 90 | — | — |
| UDL-23 | A23 (10) | — | — | — | 90 | — | — |
| UDL-24 | A24 (10) | — | — | — | 90 | — | — |
| UDL-25 | A25 (10) | — | — | — | 90 | — | — |
| UDL-26 | A26 (10) | — | — | — | 90 | — | — |

TABLE 6-continued

| Organic Film Material | Compound (parts by mass) | Crosslinking agent (parts by mass) | Acid generator (parts by mass) | High-boiling-point solvent (parts by mass) | PGMEA (parts by mass) | PGME (parts by mass) | CyHO (parts by mass) |
|---|---|---|---|---|---|---|---|
| UDL-27 | A27 (10) | — | — | — | 90 | — | — |
| UDL-28 | A28 (10) | — | — | — | 90 | — | — |
| UDL-29 | A9 (10) | — | — | S1 (10) | 80 | — | — |
| UDL-30 | A9 (10) | — | — | S2 (10) | 80 | — | — |
| Comparative UDL-1 | R1 (10) | — | — | — | 90 | — | — |
| Comparative UDL-2 | R2 (10) | XL1 (2) | AG1 (0.1) | — | 30 | 70 | — |
| Comparative UDL-3 | R3 (10) | XL1 (2) | AG1 (0.1) | — | 90 | — | — |
| Comparative UDL-4 | R4 (10) | — | — | — | — | — | 90 |
| Comparative UDL-5 | R5 (10) | XL1 (3) | AG1 (0.1) | — | 20 | 80 | — |

Filling Property Evaluation (Examples 1-1 to 1-30, Comparative Examples 1-1 to 1-5)

The compositions (UDL-1 to -30, comparative UDL-1 to -5) for forming an organic film were each applied onto a SiO$_2$ wafer substrate having a dense hole pattern (hole diameter: 0.16 μm, hole depth: 0.50 μm, distance between the centers of two adjacent holes: 0.32 μm) and baked using a hot plate in the atmosphere under the conditions shown in Table 7. Thus, a resist underlayer film 8 was formed as shown in FIG. 2 (I). The substrate used was a base substrate 7 (SiO$_2$ wafer substrate) having a dense hole pattern as shown in FIG. 2 (G) (top view) and FIG. 2 (H) (sectional view). The sectional shapes of the resulting wafer substrates were observed with a scanning electron microscope (SEM) to check whether or not the holes were filled with the organic film without voids (space). Table 7 shows the results. If an organic film material having poor filling property is used, voids occur inside the holes in this evaluation. When an organic film material having good filling property is used, the holes are filled with the organic film without voids in this evaluation as shown in FIG. 2 (I).

TABLE 7

| | Composition for forming organic film | Presence/absence of voids | Baking conditions |
|---|---|---|---|
| Example 1-1 | UDL-1 | Absent | 300° C. × 60 s |
| Example 1-2 | UDL-2 | Absent | 300° C. × 60 s |
| Example 1-3 | UDL-3 | Absent | 250° C. × 60 s |
| Example 1-4 | UDL-4 | Absent | 250° C. × 60 s |
| Example 1-5 | UDL-5 | Absent | 300° C. × 60 s |
| Example 1-6 | UDL-6 | Absent | 300° C. × 60 s |
| Example 1-7 | UDL-7 | Absent | 300° C. × 60 s |
| Example 1-8 | UDL-8 | Absent | 250° C. × 60 s |
| Example 1-9 | UDL-9 | Absent | 250° C. × 60 s |
| Example 1-10 | UDL-10 | Absent | 300° C. × 60 s |
| Example 1-11 | UDL-11 | Absent | 250° C. × 60 s |
| Example 1-12 | UDL-12 | Absent | 300° C. × 60 s |
| Example 1-13 | UDL-13 | Absent | 300° C. × 60 s |
| Example 1-14 | UDL-14 | Absent | 250° C. × 60 s |
| Example 1-15 | UDL-15 | Absent | 250° C. × 60 s |
| Example 1-16 | UDL-16 | Absent | 250° C. × 60 s |
| Example 1-17 | UDL-17 | Absent | 300° C. × 60 s |
| Example 1-18 | UDL-18 | Absent | 300° C. × 60 s |
| Example 1-19 | UDL-19 | Absent | 250° C. × 60 s |
| Example 1-20 | UDL-20 | Absent | 300° C. × 60 s |
| Example 1-21 | UDL-21 | Absent | 300° C. × 60 s |
| Example 1-22 | UDL-22 | Absent | 300° C. × 60 s |
| Example 1-23 | UDL-23 | Absent | 250° C. × 60 s |
| Example 1-24 | UDL-24 | Absent | 250° C. × 60 s |
| Example 1-25 | UDL-25 | Absent | 250° C. × 60 s |
| Example 1-26 | UDL-26 | Absent | 250° C. × 60 s |
| Example 1-27 | UDL-27 | Absent | 250° C. × 60 s |
| Example 1-28 | UDL-28 | Absent | 250° C. × 60 s |
| Example 1-29 | UDL-29 | Absent | 250° C. × 60 s |
| Example 1-30 | UDL-30 | Absent | 250° C. × 60 s |
| Comparative Example 1-1 | Comparative UDL-1 | Delamination | 250° C. × 60 s |
| Comparative Example 1-2 | Comparative UDL-2 | Delamination | 250° C. × 60 s |
| Comparative Example 1-3 | Comparative UDL-3 | Present | 250° C. × 60 s |
| Comparative Example 1-4 | Comparative UDL-4 | Present | 350° C. × 60 s |
| Comparative Example 1-5 | Comparative UDL-5 | Present | 250° C. × 60 s |

As shown in Table 7, in Examples 1-1 to 1-30 where the inventive compositions for forming an organic film (UDL-1 to -30) were used, it was possible to fill the hole patterns without voids, confirming that the filling property was high. Furthermore, since a structure having two carbonyl groups has high adhesiveness to a substrate, delamination was not observed. On the other hand, in Comparative Examples 1-1 and 1-2, adhesiveness was insufficient, and delamination was observed on the patterned substrates. Meanwhile, in Comparative Examples 1-3, 1-4, and 1-5, delamination due to insufficient adhesiveness was not observed, but voids were observed due to insufficient filling property.

Planarizing Property Evaluation (Examples 2-1 to 2-30, Comparative Examples 2-1 to 2-5)

The compositions (UDL-1 to -30, comparative UDL-1 to -5) for forming an organic film were each applied onto a base substrate 9 (SiO$_2$ wafer substrate) having a giant isolated trench pattern (FIG. 3 (J), trench width: 10 μm, trench depth: 0.10 μm) and baked in the atmosphere using a hot plate under the conditions shown in Table 8. Then, a step (delta 10 in FIG. 3 (K)) between the trench portion and the non-trench portion of a resist underlayer film 10 was observed with an atomic force microscope (AFM) NX10 manufactured by Park systems Corp. Table 8 shows the results. In this evaluation, the smaller the step, the better the planarizing property. Note that, in this evaluation, a trench pattern having a depth of 0.10 μm was generally planarized using an organic film material having a film thickness of approximately 0.2 μm. This is a severe evaluation condition to evaluate the planarizing property.

TABLE 8

|  | Composition For Forming Organic Film | Step (nm) | Baking conditions |
|---|---|---|---|
| Example 2-1 | UDL-1 | 30 | 300° C. × 60 s |
| Example 2-2 | UDL-2 | 25 | 300° C. × 60 s |
| Example 2-3 | UDL-3 | 15 | 250° C. × 60 s |
| Example 2-4 | UDL-4 | 15 | 250° C. × 60 s |
| Example 2-5 | UDL-5 | 35 | 300° C. × 60 s |
| Example 2-6 | UDL-6 | 30 | 300° C. × 60 s |
| Example 2-7 | UDL-7 | 30 | 300° C. × 60 s |
| Example 2-8 | UDL-8 | 20 | 250° C. × 60 s |
| Example 2-9 | UDL-9 | 20 | 250° C. × 60 s |
| Example 2-10 | UDL-10 | 25 | 300° C. × 60 s |
| Example 2-11 | UDL-11 | 20 | 250° C. × 60 s |
| Example 2-12 | UDL-12 | 30 | 300° C. × 60 s |
| Example 2-13 | UDL-13 | 30 | 300° C. × 60 s |
| Example 2-14 | UDL-14 | 25 | 250° C. × 60 s |
| Example 2-15 | UDL-15 | 15 | 250° C. × 60 s |
| Example 2-16 | UDL-16 | 15 | 250° C. × 60 s |
| Example 2-17 | UDL-17 | 20 | 300° C. × 60 s |
| Example 2-18 | UDL-18 | 20 | 300° C. × 60 s |
| Example 2-19 | UDL-19 | 10 | 250° C. × 60 s |
| Example 2-20 | UDL-20 | 20 | 300° C. × 60 s |
| Example 2-21 | UDL-21 | 25 | 300° C. × 60 s |
| Example 2-22 | UDL-22 | 25 | 300° C. × 60 s |
| Example 2-23 | UDL-23 | 15 | 250° C. × 60 s |
| Example 2-24 | UDL-24 | 15 | 250° C. × 60 s |
| Example 2-25 | UDL-25 | 20 | 250° C. × 60 s |
| Example 2-26 | UDL-26 | 10 | 250° C. × 60 s |
| Example 2-27 | UDL-27 | 10 | 250° C. × 60 s |
| Example 2-28 | UDL-28 | 15 | 250° C. × 60 s |
| Example 2-29 | UDL-29 | 10 | 250° C. × 60 s |
| Example 2-30 | UDL-30 | 10 | 250° C. × 60 s |
| Comparative Example 2-1 | Comparative UDL-1 | 50 | 250° C. × 60 s |
| Comparative Example 2-2 | Comparative UDL-2 | 90 | 250° C. × 60 s |
| Comparative Example 2-3 | Comparative UDL-3 | 95 | 250° C. × 60 s |
| Comparative Example 2-4 | Comparative UDL-4 | 80 | 350° C. × 60 s |
| Comparative Example 2-5 | Comparative UDL-5 | 90 | 250° C. × 60 s |

As shown in Table 8, in Examples 2-1 to 2-30 where the inventive compositions (UDL-1 to -30) for forming an organic film were used, the resist underlayer films had smaller steps between the trench portion and the non-trench portion compared with Comparative Examples 2-1 to 2-5 where comparative compositions (comparative UDL-1 to -5) for forming an organic film were used, confirming that the planarizing property was excellent. Furthermore, comparing Examples 2-29 and 2-30 where compound (A9) was used and a high-boiling-point solvent was added with Example 2-9 where compound (A9) was used and a high-boiling-point solvent was not added, it was confirmed that planarizing property was further improved by adding the high-boiling-point solvent. On the other hand, in Comparative Examples 2-2, 2-3, and 2-5 where a crosslinking agent was needed, it was confirmed that the steps in the resist underlayer film between the trench portion and the non-trench portion was large, since film shrinking during baking was great.

Adhesiveness Test (Examples 3-1 to 3-30, Comparative Examples 3-1 to 3-5)

The compositions (UDL-1 to -30, comparative UDL-1 to -5) for forming an organic film were each applied onto a SiO$_2$ wafer substrate and baked using a hot plate in the atmosphere under the conditions shown in Table 9. Thus, an organic film with a film thickness of 200 nm was formed. This wafer with an organic film was cut into a 1×1 cm square, and an aluminum pin with epoxy adhesive was fastened to the cut wafer with a dedicated jig. Thereafter, the assembly was heated with an oven at 150° C. for 1 hour to bond the aluminum pin to the substrate. After cooling to room temperature, initial adhesiveness was evaluated based on the resistance force by a thin-film adhesion strength measurement apparatus (Sebastian Five-A).

FIG. 4 shows an explanatory diagram showing an adhesiveness measurement method. In FIG. 4, reference number 11 denotes a silicon wafer (substrate), 12 denotes a cured film, 13 denotes an aluminum pin with adhesive, 14 denotes a support, 15 denotes a grip, and 16 denotes a tensile direction. The adhesion is an average of 12 measurement points, and a larger value indicates that the organic film has higher adhesiveness with respect to the substrate. The adhesiveness was evaluated by comparing the obtained values. Table 9 shows the results.

TABLE 9

|  | Composition for forming organic film | Adhesion (mN) | Baking conditions |
|---|---|---|---|
| Example 3-1 | UDL-1 | 370 | 300° C. × 60 s |
| Example 3-2 | UDL-2 | 400 | 300° C. × 60 s |
| Example 3-3 | UDL-3 | 420 | 250° C. × 60 s |
| Example 3-4 | UDL-4 | 430 | 250° C. × 60 s |
| Example 3-5 | UDL-5 | 390 | 300° C. × 60 s |
| Example 3-6 | UDL-6 | 390 | 300° C. × 60 s |
| Example 3-7 | UDL-7 | 400 | 300° C. × 60 s |
| Example 3-8 | UDL-8 | 440 | 250° C. × 60 s |
| Example 3-9 | UDL-9 | 460 | 250° C. × 60 s |
| Example 3-10 | UDL-10 | 360 | 300° C. × 60 s |
| Example 3-11 | UDL-11 | 390 | 250° C. × 60 s |
| Example 3-12 | UDL-12 | 440 | 300° C. × 60 s |
| Example 3-13 | UDL-13 | 450 | 300° C. × 60 s |
| Example 3-14 | UDL-14 | 390 | 250° C. × 60 s |
| Example 3-15 | UDL-15 | 430 | 250° C. × 60 s |
| Example 3-16 | UDL-16 | 420 | 250° C. × 60 s |
| Example 3-17 | UDL-17 | 400 | 300° C. × 60 s |
| Example 3-18 | UDL-18 | 420 | 300° C. × 60 s |
| Example 3-19 | UDL-19 | 470 | 250° C. × 60 s |
| Example 3-20 | UDL-20 | 410 | 300° C. × 60 s |
| Example 3-21 | UDL-21 | 440 | 300° C. × 60 s |
| Example 3-22 | UDL-22 | 450 | 300° C. × 60 s |
| Example 3-23 | UDL-23 | 490 | 250° C. × 60 s |
| Example 3-24 | UDL-24 | 410 | 250° C. × 60 s |
| Example 3-25 | UDL-25 | 430 | 250° C. × 60 s |
| Example 3-26 | UDL-26 | 360 | 250° C. × 60 s |
| Example 3-27 | UDL-27 | 380 | 250° C. × 60 s |
| Example 3-28 | UDL-28 | 380 | 250° C. × 60 s |
| Example 3-29 | UDL-29 | 390 | 250° C. × 60 s |
| Example 3-30 | UDL-30 | 400 | 250° C. × 60 s |
| Comparative Example 3-1 | Comparative UDL-1 | 200 | 250° C. × 60 s |
| Comparative Example 3-2 | Comparative UDL-2 | 240 | 250° C. × 60 s |
| Comparative Example 3-3 | Comparative UDL-3 | 300 | 250° C. × 60 s |
| Comparative Example 3-4 | Comparative UDL-4 | 320 | 350° C. × 60 s |
| Comparative Example 3-5 | Comparative UDL-5 | 360 | 250° C. × 60 s |

As shown in Table 9, it was confirmed that Examples 3-1 to 3-30 where the inventive compositions (UDL-1 to -30) for forming an organic film were used, adhesion was more excellent compared with Comparative Examples 3-1 to 3-5 where comparative compositions (comparative UDL-1 to -5) for forming an organic film were used. It can be seen that, compared to comparative UDL-1 and -2 where delamination occurred in the filling property evaluation, Examples 3-1 to 3-30 where the inventive composition for forming an organic film was used had approximately twice as much adhesion. Moreover, in Example 3-13, having two carbonyl groups and an amide group, the adhesion was approximately 1.4 times the adhesion in Comparative Example 3-4, having only an amide group. This reveals that having both a structure having two carbonyl groups and an amide group contributes to exhibition of high adhesiveness. Furthermore, Examples 3-21 to 3-23 having a triple bond terminal group have approximately 1.2 to 1.3 times the adhesion of Comparative Example 3-5, not having a triple bond terminal group. Thus, it is revealed that the reduction of film shrinking attributable to a triple bond terminal group contributes to adhesiveness.

Film Shrinking Test (Examples 4-1 to 4-30, Comparative Examples 4-1 to 4-5)

UDL-1 to -30, and comparative UDL-1 to -5 prepared above were each applied onto a Bare-Si substrate, baked using a hot plate in the atmosphere at 100° C. for 60 seconds, and the film thickness was measured. Next, additional baking was performed under the baking conditions described in Table 10 in the atmosphere, and the film thickness was measured again. The film shrinking rate was evaluated by calculating the ratio of the film thicknesses before and after the additional baking. That is, film shrinking rate (%)=100×{(film thickness before additional baking)−(film thickness after additional baking)}/(film thickness before additional baking). Table 10 shows the results.

TABLE 10

|  | Composition for forming organic film | Film shrinking rate (%) | Baking conditions |
| --- | --- | --- | --- |
| Example 4-1 | UDL-1 | 3.1 | 300° C. × 60 s |
| Example 4-2 | UDL-2 | 2.7 | 300° C. × 60 s |
| Example 4-3 | UDL-3 | 1.6 | 250° C. × 60 s |
| Example 4-4 | UDL-4 | 1.4 | 250° C. × 60 s |
| Example 4-5 | UDL-5 | 2.8 | 300° C. × 60 s |
| Example 4-6 | UDL-6 | 2.5 | 300° C. × 60 s |
| Example 4-7 | UDL-7 | 2.6 | 300° C. × 60 s |
| Example 4-8 | UDL-8 | 2.2 | 250° C. × 60 s |
| Example 4-9 | UDL-9 | 2.5 | 250° C. × 60 s |
| Example 4-10 | UDL-10 | 3.1 | 300° C. × 60 s |
| Example 4-11 | UDL-11 | 1.7 | 250° C. × 60 s |
| Example 4-12 | UDL-12 | 2.6 | 300° C. × 60 s |
| Example 4-13 | UDL-13 | 2.5 | 300° C. × 60 s |
| Example 4-14 | UDL-14 | 1.9 | 250° C. × 60 s |
| Example 4-15 | UDL-15 | 1.6 | 250° C. × 60 s |
| Example 4-16 | UDL-16 | 1.8 | 250° C. × 60 s |
| Example 4-17 | UDL-17 | 2.9 | 300° C. × 60 s |
| Example 4-18 | UDL-18 | 2.3 | 300° C. × 60 s |
| Example 4-19 | UDL-19 | 1.8 | 250° C. × 60 s |
| Example 4-20 | UDL-20 | 2.0 | 300° C. × 60 s |
| Example 4-21 | UDL-21 | 2.3 | 300° C. × 60 s |
| Example 4-22 | UDL-22 | 2.5 | 300° C. × 60 s |
| Example 4-23 | UDL-23 | 1.2 | 250° C. × 60 s |
| Example 4-24 | UDL-24 | 1.5 | 250° C. × 60 s |
| Example 4-25 | UDL-25 | 1.7 | 250° C. × 60 s |
| Example 4-26 | UDL-26 | 2.9 | 250° C. × 60 s |
| Example 4-27 | UDL-27 | 2.7 | 250° C. × 60 s |
| Example 4-28 | UDL-28 | 2.8 | 250° C. × 60 s |
| Example 4-29 | UDL-29 | 6.2 | 250° C. × 60 s |
| Example 4-30 | UDL-30 | 5.8 | 250° C. × 60 s |
| Comparative Example 4-1 | Comparative UDL-1 | 2.4 | 250° C. × 60 s |
| Comparative Example 4-2 | Comparative UDL-2 | 15.3 | 250° C. × 60 s |
| Comparative Example 4-3 | Comparative UDL-3 | 13.8 | 250° C. × 60 s |
| Comparative Example 4-4 | Comparative UDL-4 | 2.8 | 350° C. × 60 s |
| Comparative Example 4-5 | Comparative UDL-5 | 12.4 | 250° C. × 60 s |

As shown in Table 10, it was confirmed that the shrinking rate after the additional baking was low in Examples 4-1 to 4-28 where the inventive compositions (UDL-1 to -28) for forming an organic film were used. On the other hand, in Comparative Examples 4-2, 4-3, and 4-5 where compositions (comparative UDL-2, -3, -5) for forming an organic film for the Comparative Examples were used, the shrinking rate after the additional baking was high since a crosslinking agent was contained, and fluctuation in the film thickness was large compared to Examples 4-1 to 4-28. Meanwhile, in Examples 4-29 and 4-30 where the inventive compositions (UDL-29, -30) for forming an organic film were used, the film shrinking rate after the additional baking was high compared with Example 4-9 where the same compound was used since a high-boiling-point solvent is contained and the solvent remains in the film after the baking at 100° C. However, this was half the film shrinking rate of Comparative Examples 4-2, 4-3, and 4-5 or less. Note that in Comparative Examples 4-1 and 4-4 where comparative compositions (comparative UDL-1, -4) for forming an organic film were used, the shrinking rate was low because a triple-bond-containing terminal group was contained.

Pattern Etching Test (Examples 5-1 to 5-30, Comparative Examples 5-1 to 5-5)

UDL-1 to -30 prepared above and comparative UDL-1 to -5 were each applied onto a SiO$_2$ substrate having a trench pattern (trench width: 10 μm, trench depth: 0.10 μm) with a SiO$_2$ film formed, the SiO$_2$ film having a film thickness of 200 nm treated with HMDS. Then, a resist underlayer film was formed by baking under the conditions shown in Table 14 in the atmosphere so that the film thickness on the Bare-Si substrate was 200 nm. A silicon-atom-containing resist middle layer material (SOG-1) was applied onto the resist underlayer film and baked at 220° C. for 60 seconds to form a resist middle layer film having a film thickness of 35 nm. A resist upper layer film material (SL resist for ArF) was applied thereon and baked at 105° C. for 60 seconds to form a resist upper layer film having a film thickness of 100 nm. A liquid immersion top coat (TC-1) was applied onto the resist upper layer film and baked at 90° C. for 60 seconds to form a top coat having a film thickness of 50 nm.

The resist upper layer film material (monolayer resist for ArF) was prepared by: dissolving a polymer (RP1), an acid generator (PAG1), and a basic compound (Amine1) into a solvent containing 0.1 mass % FC-430 (manufactured by Sumitomo 3M Ltd.) in proportions shown in Table 11; and filtering the solution through a 0.1-μm filter made of a fluorinated resin.

TABLE 11

| | Polymer (parts by mass) | Acid generator (parts by mass) | Basic compound (parts by mass) | Solvent (parts by mass) |
|---|---|---|---|---|
| SL resist for ArF | RP1 (100) | PAG1 (6.6) | Amine1 (0.8) | PGMEA (2500) |

The structural formulae of the polymer (RP1), acid generator (PAG1), and basic compound (Amine1) used are shown below.

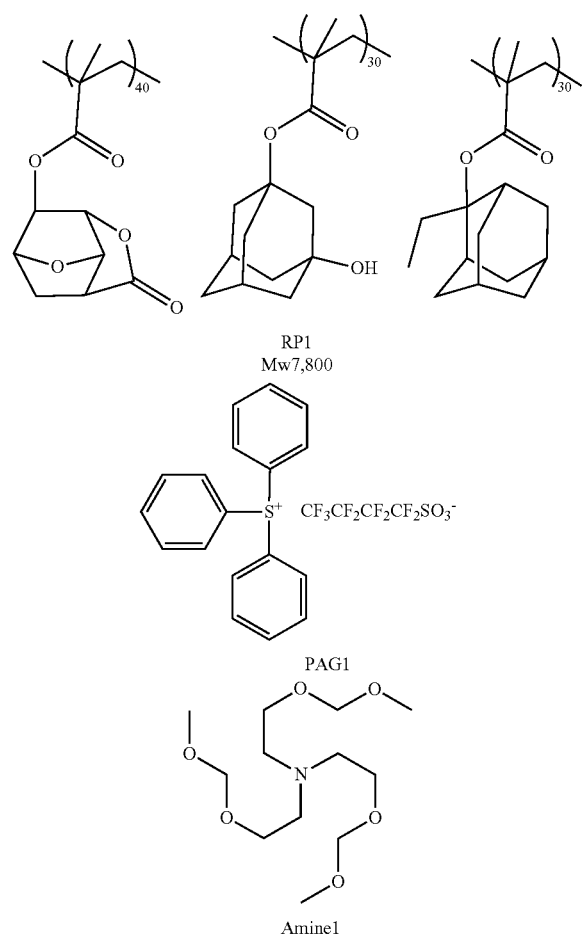

RP1
Mw7,800

PAG1

Amine1

The liquid immersion top coat material (TC-1) was prepared by: dissolving a top coat polymer (PP1) into organic solvents in proportions shown in Table 12; and filtering the solution through a 0.1-μm filter made of a fluorinated resin.

TABLE 12

| | Polymer (parts by mass) | Organic solvent (parts by mass) |
|---|---|---|
| TC-1 | PP1 (100) | Diisoamyl ether (2700) 2-methyl-1-butanol (270) |

The structural formula of the used polymer (PP1) is shown below.

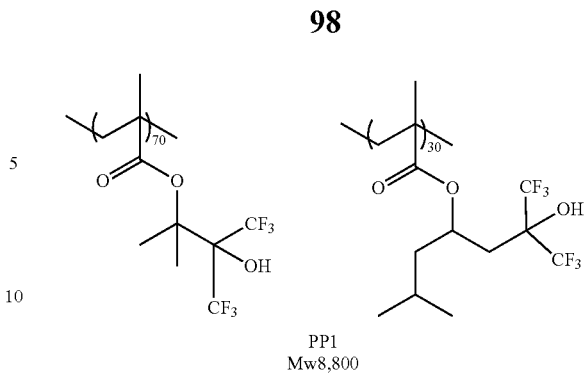

PP1
Mw8,800

The silicon-atom-containing resist middle layer material (SOG-1) was prepared by: dissolving a polymer shown by an ArF silicon-containing middle layer film polymer (SiP1) and a crosslinking catalyst (CAT1) into an organic solvent containing 0.1 mass % FC-4430 (manufactured by Sumitomo 3M Ltd.) in proportions shown in Table 13; and filtering the solution through a filter made of a fluorinated resin with a pore size of 0.1 μm.

TABLE 13

| | Polymer (parts by mass) | Thermally crosslinking catalyst (parts by mass) | Organic solvent (parts by mass) |
|---|---|---|---|
| SOG-1 | SiP1 (100) | CAT1 (1) | Propylene glycol monoethyl ether (4000) |

The structural formulae of the used ArF silicon-containing middle layer film polymer (SiP1) and crosslinking catalyst (CAT1) are shown below.

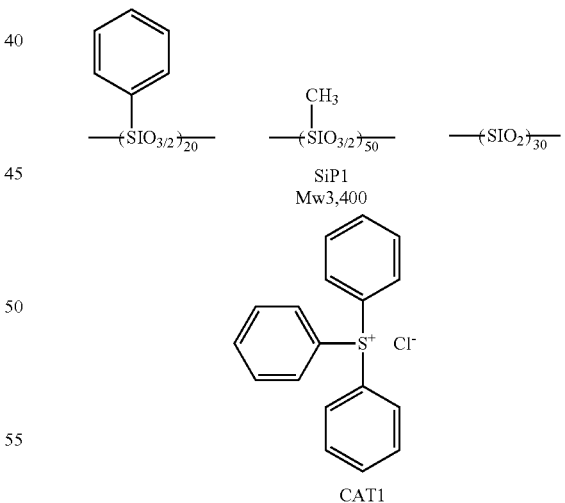

SiP1
Mw3,400

CAT1

Next, the resulting substrate was exposed to light with an ArF liquid immersion exposure apparatus (NSR-S610C manufactured by Nikon Corporation, NA: 1.30, σ: 0.98/0.65, 35° s-polarized dipole illumination, 6% halftone phase shift mask), baked (PEB) at 100° C. for 60 seconds, and developed with a 2.38 mass % tetramethylammonium hydroxide (TMAH) aqueous solution for 30 seconds. Thus, a 55 nm 1:1 positive line and space pattern was obtained.

Next, using an etching apparatus Telius manufactured by Tokyo Electron Limited, the SOG-1 film was processed by dry etching while using the resist upper layer film pattern as an etching mask; the resist underlayer film was processed while using the SOG-1 film pattern as an etching mask; and the SiO₂ film was processed while using the resist underlayer film pattern as an etching mask. The etching conditions were as follows.

Conditions for transferring the resist upper layer film pattern to the SOG-1 film.
  Chamber pressure: 10.0 Pa
  RF power: 1,500 W
  CF₄ gas flow rate: 15 sccm
  O₂ gas flow rate: 75 sccm
  Time: 15 sec Conditions for transferring the SOG-1 film pattern to the resist underlayer film.
  Chamber pressure: 2.0 Pa
  RF power: 500 W
  Ar gas flow rate: 75 sccm
  O₂ gas flow rate: 45 sccm
  Time: 120 sec Conditions for transferring the resist underlayer film pattern to the SiO₂ film.
  Chamber pressure: 2.0 Pa
  RF power: 2,200 W
  C₅F₁₂ gas flow rate: 20 sccm
  C₂F₆ gas flow rate: 10 sccm
  Ar gas flow rate: 300 sccm
  O₂ gas flow rate: 60 sccm
  Time: 90 sec The pattern cross sections were observed with an electron microscope (S-4700) manufactured by Hitachi, Ltd. Table 14 shows the results.

TABLE 14

| | Composition for forming organic film | Pattern profile after etching for transferring to substrate | Baking conditions |
|---|---|---|---|
| Example 5-1 | UDL-1 | Vertical profile | 300° C. × 60 s |
| Example 5-2 | UDL-2 | Vertical profile | 300° C. × 60 s |
| Example 5-3 | UDL-3 | Vertical profile | 250° C. × 60 s |
| Example 5-4 | UDL-4 | Vertical profile | 250° C. × 60 s |
| Example 5-5 | UDL-5 | Vertical profile | 300° C. × 60 s |
| Example 5-6 | UDL-6 | Vertical profile | 300° C. × 60 s |
| Example 5-7 | UDL-7 | Vertical profile | 300° C. × 60 s |
| Example 5-8 | UDL-8 | Vertical profile | 250° C. × 60 s |
| Example 5-9 | UDL-9 | Vertical profile | 250° C. × 60 s |
| Example 5-10 | UDL-10 | Vertical profile | 300° C. × 60 s |
| Example 5-11 | UDL-11 | Vertical profile | 250° C. × 60 s |
| Example 5-12 | UDL-12 | Vertical profile | 300° C. × 60 s |
| Example 5-13 | UDL-13 | Vertical profile | 300° C. × 60 s |
| Example 5-14 | UDL-14 | Vertical profile | 250° C. × 60 s |
| Example 5-15 | UDL-15 | Vertical profile | 250° C. × 60 s |
| Example 5-16 | UDL-16 | Vertical profile | 250° C. × 60 s |
| Example 5-17 | UDL-17 | Vertical profile | 300° C. × 60 s |
| Example 5-18 | UDL-18 | Vertical profile | 300° C. × 60 s |
| Example 5-19 | UDL-19 | Vertical profile | 250° C. × 60 s |
| Example 5-20 | UDL-20 | Vertical profile | 300° C. × 60 s |
| Example 5-21 | UDL-21 | Vertical profile | 300° C. × 60 s |
| Example 5-22 | UDL-22 | Vertical profile | 300° C. × 60 s |
| Example 5-23 | UDL-23 | Vertical profile | 250° C. × 60 s |
| Example 5-24 | UDL-24 | Vertical profile | 250° C. × 60 s |
| Example 5-25 | UDL-25 | Vertical profile | 250° C. × 60 s |
| Example 5-26 | UDL-26 | Vertical profile | 250° C. × 60 s |
| Example 5-27 | UDL-27 | Vertical profile | 250° C. × 60 s |
| Example 5-28 | UDL-28 | Vertical profile | 250° C. × 60 s |
| Example 5-29 | UDL-29 | Vertical profile | 250° C. × 60 s |
| Example 5-30 | UDL-30 | Vertical profile | 250° C. × 60 s |
| Comparative Example 5-1 | Comparative UDL-1 | Pattern collapse | 250° C. × 60 s |
| Comparative Example 5-2 | Comparative UDL-2 | Pattern collapse | 250° C. × 60 s |
| Comparative Example 5-3 | Comparative UDL-3 | Pattern collapse | 250° C. × 60 s |
| Comparative Example 5-4 | Comparative UDL-4 | Pattern collapse | 350° C. × 60 s |
| Comparative Example 5-5 | Comparative UDL-5 | Pattern collapse | 250° C. × 60 s |

As shown in Table 14, it was confirmed from the results of the inventive materials (Examples 5-1 to 5-30) for forming an organic film that the resist upper layer film pattern was favorably transferred to the final substrate in each case, and that the inventive materials for forming an organic film are suitably used in fine processing according to the multi-layer resist method. On the other hand, in Comparative Examples 5-1 to 5-5, filling property and adhesiveness were insufficient, as demonstrated in the filling property evaluation and the adhesiveness test. Therefore, pattern collapse occurred at patterning, and it was not possible to form a pattern.

Patterning Test (Examples 6-1 to 6-30, Comparative Examples 6-1 to 6-5)

UDL-1 to -30 prepared above and comparative UDL-1 to -5 were each applied onto a SiO₂ substrate having a trench pattern (trench width: 10 μm, trench depth: 0.10 μm) with a SiO₂ film formed, the SiO₂ film having a film thickness of 200 nm treated with HMDS. A coating film was formed by the same method as the pattern etching test except that the baking was performed under the conditions shown in Table 15 under such a nitrogen stream that the oxygen concentration was controlled to 0.2% or less. Then, patterning and dry etching were performed, and the obtained pattern profile was observed.

TABLE 15

| | Composition for forming organic film | Pattern profile after etching for transferring to substrate | Baking conditions |
|---|---|---|---|
| Example 6-1 | UDL-1 | Vertical profile | 300° C. × 60 s |
| Example 6-2 | UDL-2 | Vertical profile | 300° C. × 60 s |
| Example 6-3 | UDL-3 | Vertical profile | 250° C. × 60 s |
| Example 6-4 | UDL-4 | Vertical profile | 250° C. × 60 s |
| Example 6-5 | UDL-5 | Vertical profile | 300° C. × 60 s |
| Example 6-6 | UDL-6 | Vertical profile | 300° C. × 60 s |
| Example 6-7 | UDL-7 | Vertical profile | 300° C. × 60 s |
| Example 6-8 | UDL-8 | Vertical profile | 250° C. × 60 s |
| Example 6-9 | UDL-9 | Vertical profile | 250° C. × 60 s |
| Example 6-10 | UDL-10 | Vertical profile | 300° C. × 60 s |
| Example 6-11 | UDL-11 | Vertical profile | 250° C. × 60 s |
| Example 6-12 | UDL-12 | Vertical profile | 300° C. × 60 s |
| Example 6-13 | UDL-13 | Vertical profile | 300° C. × 60 s |
| Example 6-14 | UDL-14 | Vertical profile | 250° C. × 60 s |
| Example 6-15 | UDL-15 | Vertical profile | 250° C. × 60 s |
| Example 6-16 | UDL-16 | Vertical profile | 250° C. × 60 s |
| Example 6-17 | UDL-17 | Vertical profile | 300° C. × 60 s |
| Example 6-18 | UDL-18 | Vertical profile | 300° C. × 60 s |
| Example 6-19 | UDL-19 | Vertical profile | 250° C. × 60 s |
| Example 6-20 | UDL-20 | Vertical profile | 300° C. × 60 s |
| Example 6-21 | UDL-21 | Vertical profile | 300° C. × 60 s |
| Example 6-22 | UDL-22 | Vertical profile | 300° C. × 60 s |
| Example 6-23 | UDL-23 | Vertical profile | 250° C. × 60 s |
| Example 6-24 | UDL-24 | Vertical profile | 250° C. × 60 s |

TABLE 15-continued

| | Composition for forming organic film | Pattern profile after etching for transferring to substrate | Baking conditions |
|---|---|---|---|
| Example 6-25 | UDL-25 | Vertical profile | 250° C. × 60 s |
| Example 6-26 | UDL-26 | Vertical profile | 250° C. × 60 s |
| Example 6-27 | UDL-27 | Vertical profile | 250° C. × 60 s |
| Example 6-28 | UDL-28 | Vertical profile | 250° C. × 60 s |
| Example 6-29 | UDL-29 | Vertical profile | 250° C. × 60 s |
| Example 6-30 | UDL-30 | Vertical profile | 250° C. × 60 s |
| Comparative Example 6-1 | Comparative UDL-1 | Pattern collapse | 250° C. × 60 s |
| Comparative Example 6-2 | Comparative UDL-2 | Pattern collapse | 250° C. × 60 s |
| Comparative Example 6-3 | Comparative UDL-3 | Pattern collapse | 250° C. × 60 s |
| Comparative Example 6-4 | Comparative UDL-4 | Pattern collapse | 350° C. × 60 s |
| Comparative Example 6-5 | Comparative UDL-5 | Pattern collapse | 250° C. × 60 s |

As shown in Table 15, it was confirmed from the results of the inventive materials (Examples 6-1 to 6-30) for forming an organic film that the resist upper layer film pattern was favorably transferred to the final substrate, in each case, and that the inventive materials for forming an organic film are suitably used in fine processing according to the multilayer resist method even when the film is formed in an inert gas. On the other hand, in Comparative Examples 6-1 to 6-5, pattern collapse occurred as in the case where the film was formed in the atmosphere, and it was not possible to form a pattern.

From the above, it was revealed that the inventive materials for forming an organic film have high filling and planarizing properties and adhesion to a substrate. Thus, the inventive materials for forming an organic film are extremely useful as materials for forming an organic film used in multilayer resist methods. Moreover, the inventive patterning process using these materials can form a fine pattern with high precision even when the body to be processed is a stepped substrate.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:

1. A material for forming an organic film, comprising: a compound shown by the following general formula (1); and an organic solvent,

$$X-(R_1)_n \quad (1)$$

wherein in the general formula (1), X represents an organic group with a valency of "n" having 2 to 50 carbon atoms or an oxygen atom, "n" represents an integer of 1 to 10, and $R_1$ independently represents any of the following general formulae (2),

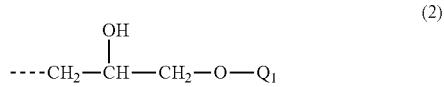

(2)

$$----CH_2-\overset{OH}{\underset{|}{CH}}-CH_2-O-Q_1$$

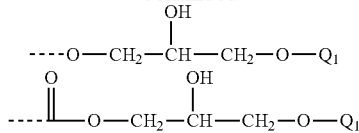

wherein in the general formulae (2), broken lines represent attachment points to X, and $Q_1$ represents a monovalent organic group containing a carbonyl group, at least a part of which is a group shown by the following general formulae (3),

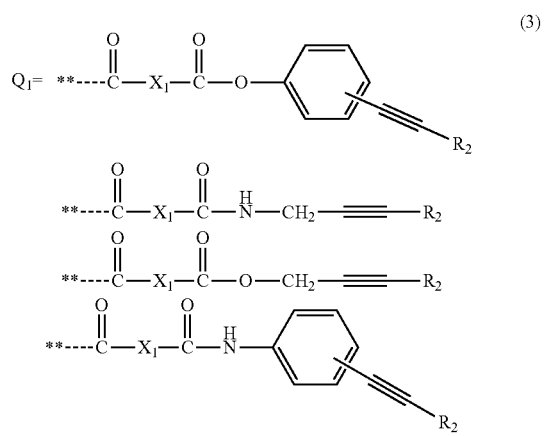

wherein in the general formulae (3), broken lines represent attachment points, $X_1$ represents a single bond or a divalent organic group having 1 to 20 carbon atoms optionally having a substituent when the organic group has an aromatic ring, $R_2$ represents a hydrogen atom, a methyl group, an ethyl group, or a phenyl group, and ** represents an attachment point.

2. The material for forming an organic film according to claim 1, wherein the compound of the general formula (1) is any of the following general formulae (4), (6), (7), (8), (9), (10), (11), (12), (13), and (14),

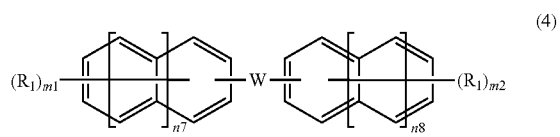

wherein in the general formula (4), n7 and n8 each independently represent 0 or 1, W represents a single bond or any structure shown by the following general formulae (5), $R_1$ has the same meaning as defined above, m1 and m2 each independently represent an integer of 0 to 4, and m1+m2 is 1 or more to 8 or less,

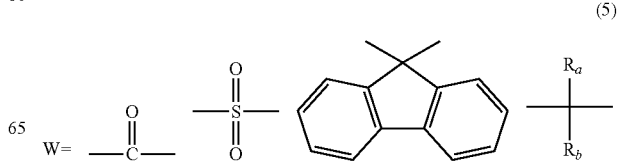

-continued

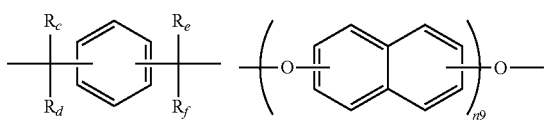

wherein in the general formulae (5), n9 represents an integer of 0 to 3, $R_a$ to $R_f$ each independently represent a hydrogen atom or an optionally fluorine-substituted alkyl group having 1 to 10 carbon atoms or phenyl group, and $R_a$ and $R_b$ are optionally bonded with each other to form a ring, (6)

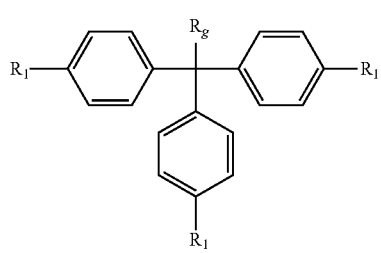

wherein in the general formula (6), $R_g$ represents a hydrogen atom, a methyl group, or a phenyl group, (7)

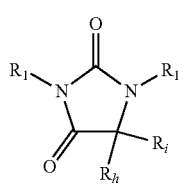

(8)

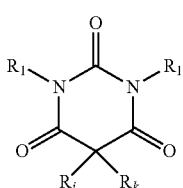

(9)

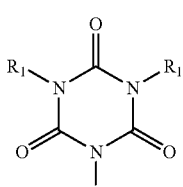

(10)

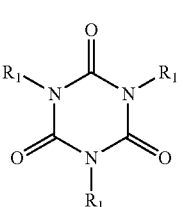

(11)

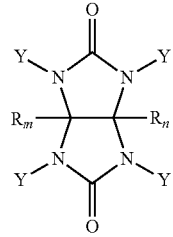

wherein in the general formulae (7) to (11), $R_1$ has the same meaning as defined above, $R_h$, $R_i$, $R_j$, $R_k$, $R_l$, $R_m$, and $R_n$ each represent a hydrogen atom, an alkyl group having 1 to 10 carbon atoms, an alkynyl group having 2 to 10 carbon atoms, an alkenyl group having 2 to 10 carbon atoms, or a benzyl group or a phenyl group optionally having a substituent on an aromatic ring, Y represents $R_1$, a hydrogen atom, an alkyl group having 1 to 10 carbon atoms, an alkynyl group having 2 to 10 carbon atoms, or an alkenyl group having 2 to 10 carbon atoms, and at least two of the four Ys in the general formula (11) represent $R_1$, (12)

$R_1$—$R_o$—$R_1$ (13)

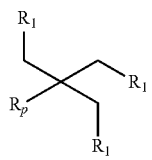

(14)

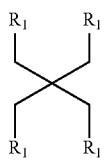

wherein in the general formulae (12) to (14), $R_1$ has the same meaning as defined above, $R_o$ in the general formula (12) represents a linear saturated or unsaturated divalent hydrocarbon group having 1 to 20 carbon atoms or a branched or cyclic saturated or unsaturated divalent hydrocarbon group having 3 to 20 carbon atoms, and $R_p$ in the general formula (13) represents a hydrogen atom or an alkyl group having 1 to 10 carbon atoms.

3. The material for forming an organic film according to claim 1, wherein $Q_1$ in the general formula (2) comprises any one or more shown by the general formulae (3) and any one or more shown by the following general formulae (15) and (16), (15)

-continued

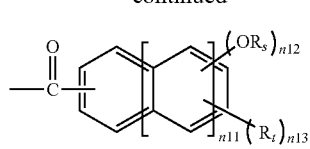

(16)

wherein $R_q$ in the general formula (15) represents a linear saturated or unsaturated hydrocarbon group having 1 to 30 carbon atoms or a branched or cyclic saturated or unsaturated hydrocarbon group having 3 to 30 carbon atoms, a methylene group comprised in $R_q$ is optionally substituted with an oxygen atom or a carbonyl group, and in the general formula (16), $R_s$ represents a hydrogen atom, a linear hydrocarbon group having 1 to 10 carbon atoms, or a branched hydrocarbon group having 3 to 10 carbon atoms, $R_t$ represents a linear hydrocarbon group having 1 to 10 carbon atoms, a branched hydrocarbon group having 3 to 10 carbon atoms, a halogen atom, a nitro group, an amino group, a nitrile group, an alkoxycarbonyl group having 1 to 10 carbon atoms, or an alkanoyloxy group having 1 to 10 carbon atoms, n11 represents 0 to 2, n12 and n13 represent a number of substituents on the aromatic ring, n12 and n13 represent an integer of 0 to 7, and n12+n13 is 0 or more to 7 or less.

4. The material for forming an organic film according to claim 1, wherein the organic solvent is a mixture of one or more organic solvents each having a boiling point of lower than 180° C. and one or more organic solvents each having a boiling point of 180° C. or higher.

5. A method for forming an organic film that functions as an organic flat film employed in a semiconductor device manufacturing process, the method comprising:
spin-coating a substrate to be processed with the material for forming an organic film according to claim 1; and
heating the substrate to be processed at a temperature of 100° C. or higher to 600° C. or lower for 10 to 600 seconds to form a cured film.

6. The method for forming an organic film according to claim 5, wherein the substrate to be processed has a structure or a step with a height of 30 nm or more.

7. A method for forming an organic film that functions as an organic flat film employed in a semiconductor device manufacturing process, the method comprising:
spin-coating a substrate to be processed with the material for forming an organic film according to claim 1; and
heating the substrate to be processed in an atmosphere having an oxygen concentration of 0.1% or more to 21% or less to form a cured film.

8. The method for forming an organic film according to claim 7, wherein the substrate to be processed has a structure or a step with a height of 30 nm or more.

9. A patterning process comprising:
forming a resist underlayer film by using the material for forming an organic film according to claim 1 on a body to be processed;
forming a resist middle layer film by using a resist middle layer film material containing a silicon atom on the resist underlayer film;
forming a resist upper layer film by using a resist upper layer film material being a photoresist composition on the resist middle layer film;
forming a circuit pattern in the resist upper layer film;
transferring the pattern to the resist middle layer film by etching while using the resist upper layer film having the formed circuit pattern as an etching mask;
transferring the pattern to the resist underlayer film by etching while using the resist middle layer film having the transferred circuit pattern as an etching mask; and
further forming the circuit pattern on the body to be processed by etching while using the resist underlayer film having the transferred circuit pattern as an etching mask.

10. The patterning process according to claim 9, wherein the pattern formation on the resist upper layer film is performed by a photolithography with a wavelength of 10 nm or more to 300 nm or less, a direct drawing by electron beam, a nanoimprinting, or a combination thereof.

11. The patterning process according to claim 9, wherein development in the patterning process is alkaline development or development with an organic solvent.

12. The patterning process according to claim 9, wherein the body to be processed is a semiconductor device substrate or the semiconductor device substrate coated with any of a metal film, a metal carbide film, a metal oxide film, a metal nitride film, a metal oxycarbide film, or a metal oxynitride film.

13. The patterning process according to claim 9, wherein the body to be processed is metallic silicon, titanium, tungsten, hafnium, zirconium, chromium, germanium, copper, silver, gold, aluminum, indium, gallium, arsenic, palladium, iron, tantalum, iridium, cobalt, manganese, molybdenum, or an alloy thereof.

14. A patterning process comprising:
forming a resist underlayer film by using the material for forming an organic film according to claim 1 on a body to be processed;
forming a resist middle layer film by using a resist middle layer film material containing a silicon atom on the resist underlayer film;
forming a BARC (organic antireflective coating) on the resist middle layer film;
forming a resist upper layer film by using a resist upper layer film material being a photoresist composition on the BARC so that a 4-layered film structure is constructed;
forming a circuit pattern in the resist upper layer film;
transferring the pattern to the BARC and the resist middle layer film by etching while using the resist upper layer film having the formed circuit pattern as an etching mask;
transferring the pattern to the resist underlayer film by etching while using the resist middle layer film having the transferred circuit pattern as an etching mask; and
further forming the circuit pattern on the body to be processed by etching while using the resist underlayer film having the transferred circuit pattern as an etching mask.

15. A patterning process comprising:
forming a resist underlayer film by using the material for forming an organic film according to claim 1 on a body to be processed;
forming an inorganic hard mask middle layer film selected from a silicon oxide film, a silicon nitride film, and a silicon oxynitride film on the resist underlayer film;
forming a resist upper layer film by using a resist upper layer film material being a photoresist composition on the inorganic hard mask middle layer film;

forming a circuit pattern in the resist upper layer film;
transferring the pattern to the inorganic hard mask middle layer film by etching while using the resist upper layer film having the formed circuit pattern as an etching mask;
transferring the pattern to the resist underlayer film by etching while using the inorganic hard mask middle layer film having the transferred circuit pattern as an etching mask; and
further forming the circuit pattern on the body to be processed by etching while using the resist underlayer film having the transferred circuit pattern as an etching mask.

16. The patterning process according to claim 15, wherein the inorganic hard mask middle layer film is formed by a CVD method or an ALD method.

17. A patterning process comprising:
forming a resist underlayer film by using the material for forming an organic film according to claim 1 on a body to be processed;
forming an inorganic hard mask middle layer film selected from a silicon oxide film, a silicon nitride film, and a silicon oxynitride film on the resist underlayer film;
forming a BARC (organic antireflective coating) on the inorganic hard mask middle layer film;
forming a resist upper layer film by using a resist upper layer film material being a photoresist composition on the BARC, so that a 4-layered film structure is constructed;
forming a circuit pattern in the resist upper layer film;
transferring the pattern to the BARC and the inorganic hard mask middle layer film by etching while using the resist upper layer film having the formed circuit pattern as an etching mask;
transferring the pattern to the resist underlayer film by etching while using the inorganic hard mask middle layer film having the transferred circuit pattern as an etching mask; and
further forming the circuit pattern on the body to be processed by etching while using the resist underlayer film having the transferred circuit pattern as an etching mask.

18. The patterning process according to claim 17, wherein the inorganic hard mask middle layer film is formed by a CVD method or an ALD method.

19. A compound shown by the following general formula (1),

(1)

wherein in the general formula (1), X represents an organic group with a valency of "n" having 2 to 50 carbon atoms or an oxygen atom, "n" represents an integer of 1 to 10, and $R_1$ independently represents any of the following general formulae (2),

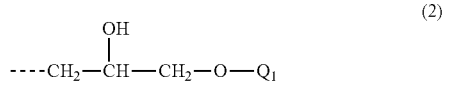

(2)

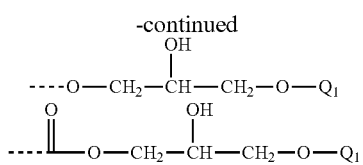

wherein in the general formulae (2), broken lines represent attachment points to X, and $Q_1$ represents a monovalent organic group containing a carbonyl group, at least a part of which is a group shown by the following general formulae (3),

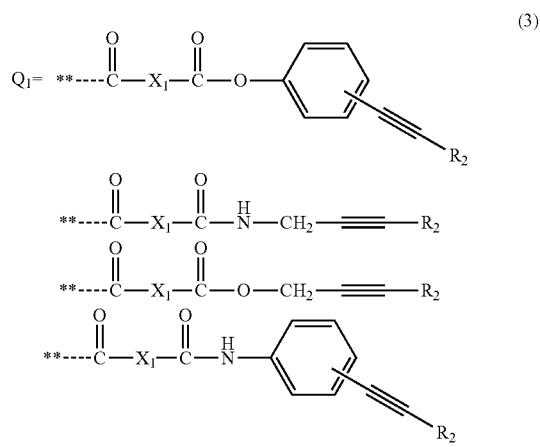

(3)

wherein in the general formulae (3), broken lines represent attachment points, $X_1$ represents a single bond or a divalent organic group having 1 to 20 carbon atoms optionally having a substituent when the organic group has an aromatic ring, $R_2$ represents a hydrogen atom, a methyl group, an ethyl group, or a phenyl group, and ** represents an attachment point.

20. The compound according to claim 19, wherein the compound of the general formula (1) is any of the following general formulae (4), (6), (7), (8), (9), (10), (11), (12), (13), and (14),

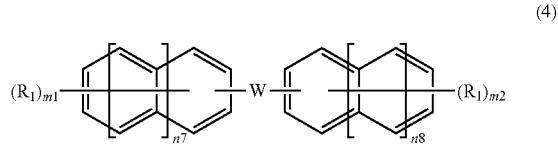

(4)

wherein in the general formula (4), n7 and n8 each independently represent 0 or 1, W represents a single bond or any structure shown by the following general formulae (5), $R_1$ has the same meaning as defined above, m1 and m2 each independently represent an integer of 0 to 4, and m1+m2 is 1 or more to 8 or less,

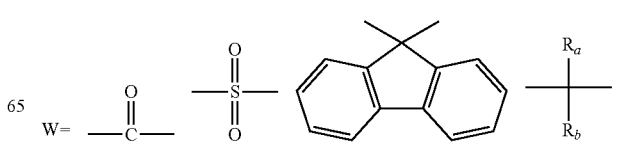

(5)

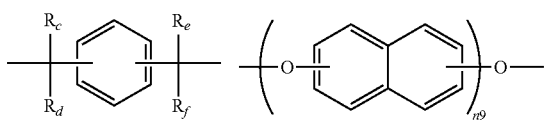

wherein in the general formulae (5), n9 represents an integer of 0 to 3, $R_a$ to $R_f$ each independently represent a hydrogen atom or an optionally fluorine-substituted alkyl group having 1 to 10 carbon atoms or phenyl group, and $R_a$ and $R_b$ are optionally bonded with each other to form a ring, (6)

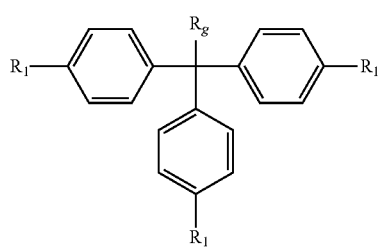

wherein in the general formula (6), $R_g$ represents a hydrogen atom, a methyl group, or a phenyl group, (7)

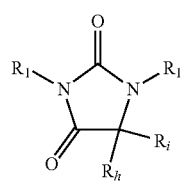

(8)

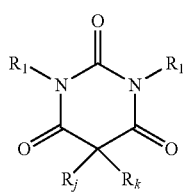

(9)

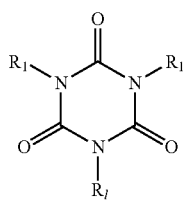

(10)

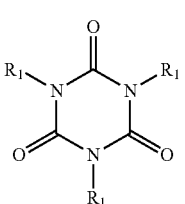

(11)

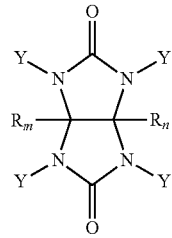

wherein in the general formulae (7) to (11), $R_1$ has the same meaning as defined above, $R_h$, $R_i$, $R_j$, $R_k$, $R_l$, $R_m$, and $R_n$ each represent a hydrogen atom, an alkyl group having 1 to 10 carbon atoms, an alkynyl group having 2 to 10 carbon atoms, an alkenyl group having 2 to 10 carbon atoms, or a benzyl group or a phenyl group optionally having a substituent on an aromatic ring, Y represents $R_1$, a hydrogen atom, an alkyl group having 1 to 10 carbon atoms, an alkynyl group having 2 to 10 carbon atoms, or an alkenyl group having 2 to 10 carbon atoms, and at least two of the four Ys in the general formula (11) represent $R_1$, (12)

$$R_1\text{—}R_o\text{—}R_1$$

(13)

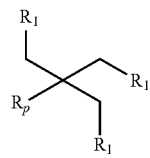

(14)

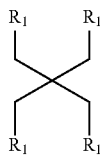

wherein in the general formulae (12) to (14), $R_1$ has the same meaning as defined above, $R_o$ in the general formula (12) represents a linear saturated or unsaturated divalent hydrocarbon group having 1 to 20 carbon atoms or a branched or cyclic saturated or unsaturated divalent hydrocarbon group having 3 to 20 carbon atoms, and $R_p$ in the general formula (13) represents a hydrogen atom or an alkyl group having 1 to 10 carbon atoms.

21. The compound according to claim 19, wherein $Q_1$ in the general formula (2) comprises any one or more shown by the general formulae (3) and any one or more shown by the following general formulae (15) and (16), (15)

-continued

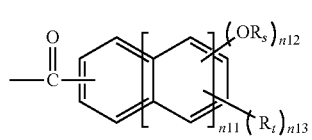

(16)

wherein $R_q$ in the general formula (15) represents a linear saturated or unsaturated hydrocarbon group having 1 to 30 carbon atoms or a branched or cyclic saturated or unsaturated hydrocarbon group having 3 to 30 carbon atoms, a methylene group comprised in $R_q$ is optionally substituted with an oxygen atom or a carbonyl group, and in the general formula (16), $R_s$ represents a hydrogen atom, a linear hydrocarbon group having 1 to 10 carbon atoms, or a branched hydrocarbon group having 3 to 10 carbon atoms, $R_t$ represents a linear hydrocarbon group having 1 to 10 carbon atoms, a branched hydrocarbon group having 3 to 10 carbon atoms, a halogen atom, a nitro group, an amino group, a nitrile group, an alkoxycarbonyl group having 1 to 10 carbon atoms, or an alkanoyloxy group having 1 to 10 carbon atoms, n11 represents 0 to 2, n12 and n13 represent a number of substituents on the aromatic ring, n12 and n13 represent an integer of 0 to 7, and n12+n13 is 0 or more to 7 or less.

* * * * *